(12) United States Patent
Gillies et al.

(10) Patent No.: US 10,214,609 B2
(45) Date of Patent: Feb. 26, 2019

(54) POLYGLYOXYLATES, MANUFACTURE AND USE THEREOF

(71) Applicant: THE UNIVERSITY OF WESTERN ONTARIO, London (CA)

(72) Inventors: Elizabeth R. Gillies, London (CA); Bo Fan, London (CA); Andrew D. Wong, London (CA); John F. Trant, LaSalle (CA)

(73) Assignee: THE UNIVERSITY OF WESTERN ONTARIO, London, ON (CA)

(*) Notice: Subject to any disclaimer, the term of this patent is extended or adjusted under 35 U.S.C. 154(b) by 0 days.

(21) Appl. No.: 15/309,112

(22) PCT Filed: May 6, 2015

(86) PCT No.: PCT/CA2015/050469
§ 371 (c)(1),
(2) Date: Nov. 4, 2016

(87) PCT Pub. No.: WO2015/168809
PCT Pub. Date: Nov. 12, 2015

(65) Prior Publication Data
US 2017/0073452 A1 Mar. 16, 2017

Related U.S. Application Data

(60) Provisional application No. 61/989,086, filed on May 6, 2014.

(51) Int. Cl.
| | |
|---|---|
| *C08G 2/30* | (2006.01) |
| *C07C 67/333* | (2006.01) |
| *C07C 69/716* | (2006.01) |
| *C07C 69/86* | (2006.01) |
| *C07C 231/12* | (2006.01) |
| *C07C 67/30* | (2006.01) |
| *C07F 7/18* | (2006.01) |
| *C08G 2/14* | (2006.01) |
| *C08G 81/00* | (2006.01) |

(52) U.S. Cl.
CPC ............... *C08G 2/30* (2013.01); *C07C 67/30* (2013.01); *C07C 67/333* (2013.01); *C07C 69/716* (2013.01); *C07C 69/86* (2013.01); *C07C 231/12* (2013.01); *C07F 7/1804* (2013.01); *C07F 7/1872* (2013.01); *C08G 2/14* (2013.01); *C08G 81/00* (2013.01)

(58) Field of Classification Search
None
See application file for complete search history.

(56) References Cited

U.S. PATENT DOCUMENTS

| | | |
|---|---|---|
| 4,144,226 A | 3/1979 | Crutchfield et al. |
| 4,146,495 A * | 3/1979 | Crutchfield .............. C08G 2/14 252/180 |
| 4,204,052 A | 5/1980 | Crutchfield et al. |
| 4,233,423 A | 11/1980 | Dyroff et al. |
| 4,600,750 A * | 7/1986 | Dyroff ..................... C08G 2/14 525/398 |

OTHER PUBLICATIONS

Kim, International Journal of Pharmaceutics, 401 (2010) p. 79-86 (Year: 2010).*
Belloncle, Polymer Degradation and Stability, 93 (2008) 1151-1157 (Year: 2008).*
Kuck, The Journal of Physical Chemistry, vol. 76, No. 24, (1972), p. 3570-3571 (Year: 1972).*
Belloncle, B. et al., Study of the Degradation of Poly(ethyl glyoxylate): Biodegradation, Toxicity and Ecotoxicity Assays. Journal of Polymers and the Environment 2012, 20 (3), 726-731.
Brachais, C. H. et al., Synthesis, characterization and stabilization of poly(methyl glyoxylate). Polymer 1997, 38 (19), 4959-4964.
Brachais, C. H. et al., In vitro degradation of poly(methyl glyoxylate) in water. Polymer 1998, 39 (04), 7.
Burel, F. et al., Synthesis and characterization of poly(ethyl glyoxylate)—a new potentially biodegradable polymer. e-Polymers, 2003, 3, 407.
Chen, E. K. Y. et al., Self-Immolative Polymers Containing Rapidly Cyclizing Spacers: Toward Rapid Depolymerization Rates. Macromolecules 2012, 45, 7364-7374.
Cohen Stuart, M. et al., Emerging applications of stimuli-responsive polymer materials. Nature Materials 2010, 9, 101.
Liu, F. et al., Recent advances and challenges in designing stimuli-responsive polymers. Progress in Polymer Science 2010, 35, 3.
Peterson, G. I. et al., Controlled Depolymerization: Stimuli-Responsive Self-Immolative Polymers, Macromolecules 2012, 45, 7317-7328.
Phillips, S. T. et al., Continuous head-to-tail depolymerization: An emerging concept for imparting amplified responses to stimuli-responsive materials. ACS Macro Letters 2014, 3, 298-304.
Schattling, P.; Jochum, F. D.; Theato, P., Multi-stimuli responsive polymers—the all-in-one talents. Polymer Chemistry 2014, 5, 25.
Wong, A. D. et al, Amplified release through the stimulus triggered degradation of self-immolative oligomers, dendrimers, and linear polymers. Advanced Drug Delivery Reviews 2012, 64 (11), 1031-1045.
Wong, A. D. et al., Multi-responsive Azobenzene End-cap for Self-immolative Polymers. ACS Macro Letters 2014, 3, 1191-1195.
Kim, J -K, et al., "Novel pH-sensitive polyacetal-based block copolymers for controlled drug delivery" Int. J. Pharm., vol. 401(1-2), 2010, pp. 79-86.
Belloncle, B. et al., "Synthesis and Degradation of Poly(ethyl glyoxylate)"ACS Symposium Series, Polymer Degradation and Performance, 2009, pp. 41-51.

(Continued)

Primary Examiner — Robert C Boyle
(74) Attorney, Agent, or Firm — Hill & Schumacher

(57) ABSTRACT

Self-immolative polymers degrade by an end-to-end depolymerization mechanism in response to the cleavage of a stabilizing end-cap from the polymer terminus. Examples include homopolymers, mixed polymers including block copolymers, suitable for a variety of applications. A polyglyoxylate can be end-capped or capped with a linker as in a block copolymer.

18 Claims, 17 Drawing Sheets

(56) References Cited

OTHER PUBLICATIONS

Ritson, D. J. et al., "Indium mediated allylation of glyoxylate oxime ethers, esters and cyanoformates" Org. Biomol. Chem., vol. 2, 2004, pp. 1921-1933.
CAS Registry No. ®: 925-61-1 (see attached document A).
CAS Registry No. ®:924-53-8 (see attached document A).
CAS Registry No. ®:6295-06-3 (see attached document A).
CAS Registry No. ®:1480470-37-8 (see attached document A).
CAS Registry No. ®:1449764-22-0 (see attached document A).
CAS Registry No. ®:1447729-71-6 (see attached document A).
CAS Registry No. ®:1149340-23-7 (see attached document A).
CAS Registry No. ®:1071661-77-2 (see attached document A).
CAS Registry No. ®:477884-85-8 (see attached document A).
CAS Registry No. ®:133017-22-8 (see attached document A).
CAS Registry No. ®:99440-80-9 (see attached document A).
CAS Registry No. ®:91538-23-7 (see attached document A).
CAS Registry No. ®:57130-87-7 (see attached document A).
Fan, B et al.: "Polyglyoxylats: A versatile Class of Troggerable Self-Immolative Polymers from Readily Accessible Monomers" JAC, vol. 136, Jun. 23, 2014 pp. 10116-10123.
International Search Report in PCT/CA2015/050469, dated Sep. 15, 2015.
Written Opinion in PCT/CA2015/050469, dated Sep. 15, 2015.

\* cited by examiner a)

b)

POLYGLYOXYLATES, MANUFACTURE AND USE THEREOF

FIELD

This invention relates to polyglyoxylates, their synthesis and use.

BACKGROUND

With increasing concerns about the environmental impact of the chemical and polymer industries, there has been a steadily growing interest in the introduction of biodegradable polymers for a variety of applications, from fertilizer and seed-coating in agri-science, to biodegradable sutures, stitches and supports in medicine, to biodegradable plastic bags for the consumer market.[1,2] Furthermore, due to the increasing costs and public concerns associated with petroleum feed stocks, alternative chemical sources, especially plant-derived materials are of increasing interest to industry for cost, resource security, and public relations purposes.[3,4] With these factors in mind, polyglyoxylates, a class of degradable polymers, are of considerable interest. The properties of the materials can be modified not only by controlling the molecular weight of the resulting polymers, but also by modifying the identity of the ester side-chain and by incorporating them into block copolymers.[5] Short polymers or oligomers are readily formed through the acid or base catalyzed polymerization of their parent glyoxylates in the presence of adventitious water. This has often made them difficult substrates for use in synthetic methodology,[6] and the reversibility and instability of the resulting polymers has also limited their applications in materials science. However, they are particularly attractive as they ultimately degrade to corresponding alcohols and glyoxylic acid hydrate, an intermediate in the glyoxylate cycle, making them excellent biocompatible candidates for biomedical and agricultural applications.[7]

Poly(methyl glyoxylate) (PMG) was first prepared by Monsanto for use as biodegradable detergent builder and complexing agent in 1979.[8,9,10] However, because of the low ceiling temperature of this polymer, it has a very short half-life at room temperature, greatly limiting possible applications. The stability of PMG can, however, be improved greatly when it is properly end-capped,[11] and investigations into the thermal stability and degradation kinetics of PMG were all completed two decades ago.[12,13] Poly(ethyl glyoxylate) (PEtG) was successfully synthesized by the Burel group through anionic polymerization in 2003.[14] Similar to PMG, PEtG is readily degradable, but the reduced toxicity of ethanol relative to methanol suggests that PEtG has increased potential in medical, pharmaceutical, and environmental applications.[15,16,17]

As both methyl glyoxylate and ethyl glyoxylate can easily be polymerized, and both polymers show different physical properties (the former being a glassy solid up to 25° C., while the latter is a white, sticky, rubber-like solid at room temperature), the potential physical properties of other members of this family demand investigation. The difficulties in the preparation and isolation of higher-order glyoxylates in sufficient purity for synthetic methodology, let alone the very high purities required for polymerization, have limited research interest and investigations into their utility. However, a general high conversion and high purity synthetic approach should allow access to a wide variety of different glyoxylates and potentially a wider variety of physical properties.

SUMMARY

The inventors have created a family of polyglyoxylates, methods of making polyglyoxylates, including a family of glyoxylates useful as precursors for manufacturing polyglyoxylates. Various embodiments include homopolymers, mixed polymers, including block copolymers suitable for a variety of applications. Advantageously, a polyglyoxylate chain is end-capped, or capped with a linker as in a block copolymer. Various embodiments and details of each are described further below. The term polyglyoxylate is used herein to mean a polymer of one or more glyoxylic acid esters.

In particular embodiments, the caps stabilize the polymer against degradation, but are self-immolative when triggered i.e., exposed to a particular stimulus. Such triggerable self-immolative polymers are a significant new class of materials that utilizes such a mechanism for their degradation.[18,19,20] Unlike traditional polymeric materials that remain intact in the environment over the very long term, or more modern (bio)degradable polymers that decompose in a relatively uncontrolled manner, self-immolative polymers remain highly stable as long as their end-cap remains in place, but upon deprotection rapidly depolymerize, monomer by monomer, into small molecules. In comparison with other stimuli-responsive materials for which multiple cleavage events are needed to break down and/or change the properties of the material, self-immolative polymers require only the cleavage of the end-cap to break down the entire polymer chain. Therefore, they afford an amplified response to the stimulus.[21,22,23] A wide variety of potential trigger conditions are available such as pH, water, enzymatic cleavage, physiological reduction or oxidation, heat and light.[18] Light is of particular interest as a stimulus both in model and practical systems as an end group can be prepared such that it cleaves at a specific wavelength of light and does not require a specific external medium for the chemical reaction.

An aspect of the invention is a general approach to the synthesis of a glyoxylate, HC(O)C(O)—OR, from the corresponding diester of fumaric acid or maleic acid, RO—(O)CCH=CHC(O)—OR. It is possible to obtain the glyoxylates in highly pure form, which is especially preferred for synthesis of polymers therefrom. A general anionic homopolymerization of these glyoxylates is illustrated by particular examples, including methyl, ethyl, n-butyl, and benzyl derivatives.

Synthesis of copolymers of the glyoxylate monomers is also demonstrated.

Illustrative examples of capped glyoxylate polymers are provided, showing that these polymers can indeed be either triggered to depolymerize by e.g., UV light or remain stable to these conditions dependent on the choice of end-cap.

Preparation of block co-polymers of polyglyoxylates with other polymers is also illustrated with installation of a multifunctional triggerable group between the two blocks. In a particular example, block copolymers containing self-immolative PEtG were used in the preparation of stimuli-responsive nanoparticles. PEG is well known to be a hydrophilic polymer while PEtG is relatively hydrophobic so depending on the block ratios, these copolymers can be assembled into micelles, worm-like micelles, vesicles, and nanoaggregates. Such assemblies can be used to encapsulate a wide range of hydrophobic species such as drugs, imaging agents, and agricultural products, with their release triggered by the stimulus that cleaves the PEtG. In another example, a triblock copolymer of poly[(dimethylamino)ethyl methacrylate] (PDMAEMA) and PEtG was synthesized. PDMAEMA is a class of hydrophilic polymer that is both thermally sensitive and pH sensitive. Amphiphilic triblock copolymers based on PEtG and PDMAEMA are thus attractive as smart block polymers responsive to e.g., light irradiation as well as changes of temperature and pH. Nanoparticles formed therefrom should also respond in different ways to different stimuli, with temperature and pH mediating nanoparticle aggregation and light triggering degradation. Block copolymers can also incorporate degradable polymers such as poly(lactic acid), poly(glycolic acid), and poly(caprolactone).

Glyoxylates having functional side chains, heretofore unknown to the inventors, have also been synthesized. Examples of functional moieties include cross-linking moieties such as vinyl, functional handles such as bromo, azido and alkynyl, and chemically active groups such as pharmaceutically active side chains. A silyl-protected hydroxyethyl glyoxylate was also prepared, which will allow further functionalization with cross-linking agents such as (meth)acrylates or other with other groups. The biocompatibility of the metabolic byproducts of polyglyoxylates makes them ideal self-immolative polymers for biomedical applications. Coupled with the ability to form vesicles and nanoparticles with the incorporation of a suitable hydrophilic block, and the incorporation of a suitable triggerable end-cap or linker to stimulate self-immolation at the appropriate physiological location and time, the introduction of pharmacophores on the glyoxylate side chain provides opportunities for the preparation of a new class of pro-drugs for slow release applications.

In another aspect, the invention provides an amphiphilic block copolymer in which a relatively hydrophobic block is a poly(glyoxylic ester), and a relatively hydrophilic block is a poly(glyoxylic acid). A preferred copolymer includes end-caps that upon cleavage permits the polymeric material to degrade with both the hydrophobic and hydrophilic blocks producing glyoxylic acid derivatives. The material would thus be biocompatible and environmentally, relatively innocuous. The polyglyoxylate block can be synthesized as described below, while the poly(glyoxylic acid) block can be prepared either though the hydrolysis of e.g., a poly(methyl glyoxylate)[8,9] or a de novo synthesis such as that described by Kimura.[24] The two moieties can be end-capped and ligated together using, for example, the copper assisted azide alkyne cycloaddition reaction described in the examples.

In addition to their utility as assemblies such as nanoparticles and vesicles in aqueous solution, the insolubility of the polyglyoxylates in water also makes them useful as stimuli-responsive coatings. A coating of polyglyoxylate can be deposited on a surface. Upon stimulus-mediated cleavage of the end-cap, the coating degrades. Such coatings could be used for products such as drugs, fertilizers, or in packaging and would enable the selective release of the payload in response to the stimulus.

An embodiment of the invention is thus a capped polymer comprising a polyglyoxylate polymer having a cap covalently linked to an end thereof, wherein the cap is selected such that upon exposure to a preselected stimulus, covalent linkage of the cap to the polymer is cleaved in preference to cleavage of bonds of the polyacetal backbone of the polymer.

In certain disclosed embodiments, there is a cap at both ends of the polymer chain. A particular type of cap is a "linker", which is a cap that acts to covalently link another polymeric chain to the polyglyoxylate polymer. A cap which serves as a terminus of the polyglyoxylate polymer is an "end-cap".

Exposure of the capped polymer to a preselected stimulus or trigger acts to cleave the cap from the polyacetal backbone to permit chemically-reactive characteristics of the polyglyoxylate polymer e.g., self-immolative characteristics of the polymer to become manifest. The covalent linkage of the cap to the polymer is cleaved in preference to cleavage of bonds making up the polyacetal backbone of the polymer so that the uncapped polymer chain is left largely if not entirely intact after cleavage of the cap(s). Triggered release of the cap(s) of a polymer thus results in the triggering of self-immolation of a polymer exposed to the appropriate degradative conditions. A "self-immolative polyglyoxylate" is a polyglyoxylate that depolymerizes end-to-end through a cascade of reactions once the cleavage of the cap from the polymer terminus has occurred. Where a cap is a linker, it is preferred that the linker be capable of spontaneously separating from the second polymeric chain if the bond to the first polymeric chain is cleaved. In a preferred embodiment, the first polymeric chain is a polyglyoxylate hydroxyl terminal that is completely released from the linker. In some cases the remaining linker will remain attached to the second polymeric chain (block) while in other cases the linker and second block will additionally be cleaved from each other. The term "self-immolative linker" refers to a linker in either such situation.

The preselected stimulus can be one or more of an aqueous solution, an enzyme (e.g., catalytic antibodies, esterases, and peptidases), a reducing agent (e.g., thiol, particularly glutathione), an oxidizing agent (e.g., hydrogen peroxide), heat, light, and change in pH.

In an aspect, the polyglyoxylate polymer has an average molecular weight in the range from 1000 Da to $10^6$ Da, 2000 to 500,000 or 3000 to 100,000 based on polystyrene standards.

The polyglyoxylate polymer can have a polydispersity index (PDI) in the range from 1.0 to 3.0 or 1.3 to 2.6.

According to an aspect, the polymer has the structure of formula (A):

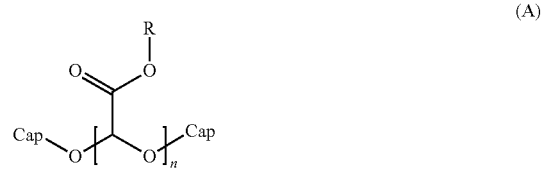

(A)

wherein n is between 10 and 2,000, or 10 and 1500, or 10 and 1000, or 20 and 1000, or 30 and 1000, or 40 and 1000, or 50 and 1000, or 100 and 1000, or 100 and 2,000, or 100 and 900, or 100 and 800 or 200 and 1000, or 200 and 800, or 200 and 700, or 300 and 1500, or 300 and 1000, or 300 and 800, or 300 and 700, or 400 and 600. R can be any of:
(i) H,
(ii) optionally substituted $C_{1-20}$ linear or branched alkyl,
(iii) optionally substituted $C_{1-20}$ cycloalkyl,
(iv) optionally substituted $C_{2-20}$ linear or branched alkenyl,
(v) optionally substituted $C_{5-20}$ cycloalkenyl (vi) optionally substituted $C_{2-20}$ linear or branched alkynyl,
(vii) optionally substituted $C_{6-20}$ aromatic,
(viii) optionally substituted $C_{4-20}$ heteroaryl,
(ix) optionally substituted $C_{7-20}$ arylalkyl,
(x) optionally substituted $C_{2-20}$ cycloheteroalkyl,
(xi) cinnamoyl,
(xii) acrylyl,
(xiii) methacrylyl, and
(xiv) —$CH_2CH_2OSi(R^i)(R^{ii})(R^{iii})$ wherein:
each of $R^i$, $R^{ii}$ and $R^{iii}$ is, independently of the other, selected from foregoing groups (i) to (x) and at least one of $R^i$, $R^{ii}$ and $R^{iii}$ is selected from foregoing groups (ii) to (x),
and
the invention includes salts of any of the foregoing.

The term "optionally substituted" means 1, 2, 3, 4 or 5 independent substitutions, by replacement of a corresponding number of hydrogen atoms, with the specified groups, radicals or moieties. Any atom with unsatisfied valences in the text, schemes, examples etc. herein is assumed to have the hydrogen atom(s) to satisfy the valences. The term "optionally substituted", when no groups radicals or moieties are specifically mentioned means the up to five substituents are selected independently from the following:

$C_{1-20}$ alkoxy,
$C_{2-20}$ alkenyloxy,
$C_{7-20}$ aryloxy,
$C_{7-20}$ cycloalkyloxy,
halogen (F, Cl, Br, I),
—OH,
—OC(O)CH=CH2 (acrylyl), —OC(O)CCH$_3$=CH$_2$ (methacrylyl),
—NH$_2$,
—N$_3$ (azido)
—C(O)R$^1$, —C(O)OR$^1$, —OC(O)R$^1$, NHR$^1$, NR$^1$R$^2$, wherein each R$^1$ and R$^2$ is independently selected from the group consisting of:
$C_{1-20}$ linear or branched alkyl, $C_{1-20}$ cycloalkyl, $C_{2-20}$ linear alkenyl, $C_{4-20}$ branched alkenyl, $C_{5-20}$ cycloalkenyl, $C_{2-20}$ linear alkynyl, $C_{5-20}$ branched alkynyl, $C_{6-20}$ aromatic, $C_{7-20}$ alkyl-substituted aromatic, $C_{7-20}$ aryl-substituted alkyl, epoxy, mercapto (—SH), NHR$^3$, NR$^3$R$^4$, wherein each R$^3$ and R$^4$ is independently selected from the group consisting of $C_{1-20}$ linear alkyl, $C_{1-20}$ branched alkyl, $C_{1-20}$ cyclic alkyl, $C_{2-20}$ linear alkenyl, $C_{4-20}$ branched alkenyl, $C_{5-20}$ cyclic alkenyl, $C_{2-20}$ linear alkynyl, $C_{5-20}$ branched alkynyl, $C_{6-20}$ aromatic, $C_{7-20}$ alkyl-substituted aromatic, and $C_{7-20}$ aryl-substituted alkyl;
—C(O)OR$^5$ wherein each R$^5$ is independently selected from the group consisting of:
$C_{1-20}$ linear alkyl, $C_{1-20}$ branched alkyl, $C_{1-20}$ cycloalkyl, $C_{2-20}$ linear alkenyl, $C_{4-20}$ branched alkenyl, $C_{5-20}$ cycloalkenyl, $C_{2-20}$ linear alkynyl, $C_{5-20}$ branched alkynyl, $C_{6-20}$ aromatic, $C_{7-20}$ alkyl-substituted aromatic, $C_{7-20}$ aryl-substituted alkyl, and epoxy.

The term "alkyl" indicates the radical obtained when one hydrogen atom is removed from a hydrocarbon. An alkyl group can contain 1 to 20 carbon atoms ($C_{1-20}$), and unless specified as linear, can be linear or branched. An alkyl group can also contain 1 to 20, 1 to 18, 1 to 16, 1 to 14, 1 to 12, 1 to 10, 1 to 8, 1 to 6, 1 to 4, 1 to 3 or 1 or 2 carbon atoms. Examples are methyl, ethyl, n-propyl, isopropyl, n-butyl, isobutyl, s-butyl, t-butyl, pentyl, isopentyl, hexyl and isohexyl.

The term "cycloalkyl" indicates a saturated cycloalkyl radical having 3 to 20 carbon, 3 to 10, 3 to 8, or 3 to 6 carbon atoms, and includes fused bicyclic rings. Examples are cyclopropyl, cyclobutyl, cyclopentyl, cyclohexyl, and cycloheptyl.

The term "alkenyl" means a mono-, di-, tri-, tetra- or pentaunsaturated hydrocarbon radical having 2 to 30 carbon atoms, which can be branched or unbranched. An alkenyl radical can also contain 2 to 20, 2 to 18, 2 to 16, 2 to 14, 2 to 12, 2 to 10, 2 to 8, 2 to 6, 2 to 5, 2 to 4, or 2 to 3 carbon atoms. Examples include ethenyl, propenyl, butenyl, pentenyl or hexenyl. A cycloalkenyl radical is a cycloalkyl radical containing 1, 2, 3, 4 or 5 carbon-carbon double bonds (C=C).

The term "alkynyl" indicates an hydrocarbon radical comprising 1 to 5 triple carbon-carbon triple bonds (C≡C) and 2 to 30 carbon atoms, and the radical can be branched or unbranched (linear). An alkynyl group can also contain 2 to 20, 2 to 18, 2 to 16, 2 to 14, 2 to 12, 2 to 10, 2 to 8, 2 to 6, 2 to 5, 2 to 4, or 2 to 3 carbon atoms. Examples include ethynyl, propynyl, butynyl, pentynyl or hexynyl.

The term "aromatic" or "aryl" means a radical of aromatic carbocyclic rings having 6 to 20 carbon atoms, or 6 to 14, 6 to 12, 6 to 10 carbon atoms. Included are fused carbocyclic rings with at least one aromatic ring, such as phenyl, naphthyl, indenyl and indanyl.

The term "heteroaryl" indicates radicals of heterocyclic aromatic rings containing 1 to 6 heteroatoms (O, S and/or N) and 1 to 20 carbon atoms. There may be 1 to 12, 1 to 10, 1 to 8, 1 to 6 or 1 to 5 carbon atoms, and 1 to 5, or 1 to 4, or 1 to 3 heteroatoms. Fused bicyclic rings with 1 to 4 heteroatoms, and having at least one ring that is aromatic are included. Examples are pyridyl, quinolyl, isoquinolyl, indolyl, tetrazolyl, thiazolyl, imidazolyl, pyrazolyl, oxazolyl, isoxazolyl, thienyl, pyrazinyl, isothiazolyl, benzimidazolyl and benzofuranyl.

An "alkoxy" group is a radical of the formula —OR in which R is $C_{1-10}$ alkyl. Examples are methoxy, ethoxy, n-propoxy, isopropoxy, n-butoxy, sec-butoxy, isobutoxy, tert-butoxy, n-pentoxy, neopentoxy, isopentoxy, hexoxy, n-heptoxy, n-octoxy, n-nonoxy and n-decoxy. An "alkenyloxy" group is a radical of the formula —OR in which R is $C_{2-10}$ alkenyl. An "aryloxy" group is a radical of the formula —OR in which R is $C_{5-10}$ aryl. An example is phenoxy ($C_6H_5O$—).

A "cycloheteroalkyl" group is a cycloalkyl radical in which one to 5 carbon atoms, and any associated hydrogen atoms as necessary, are independently replaced with the same or different heteroatom. A cycle contains 3 to 14 atoms. Examples are epoxides (epoxy radical) and radicals formed by the removal of a hydrogen atom from imidazolidine, morpholine, piperazine, piperidine, pyrazolidine, pyrrolidine and quinuclidine.

"Salts" refers to salts of a compound described herein, such as a compound of Formula (A), particularly those containing a readily ionizable group such as a carboxylate group or an amino group. Salts which may be derived from a variety of organic and inorganic counter ions are well known in the art and include, by way of example only, sodium, potassium, calcium, magnesium, ammonium, tetraalkylammonium, hydrochloride, hydrobromide, tartrate, mesylate, acetate, maleate, oxalate and the like. Illustrative salts include, but are not limited, to sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine, etc.

A preferred cap-polyacetal linkage is the carbonate linkage: —OC(O)O—R$^C$ in which the identity of R plays a role in determining the susceptibility of the linkage to various stimuli. Capping of the polyglyoxylate can frequently be conveniently achieved as illustrated herein by reaction of a freshly created polymer with a corresponding chloroformate, —XC(O)O—R$^C$, the "cap" of formula (A) being represented here by:

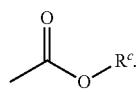

The -Cap can be an end-cap in which R$^C$ is a group that is cleaved in response to a stimulus such as light, enzymes, heat, change in pH or redox potential.

Examples of -Cap are:

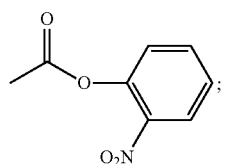

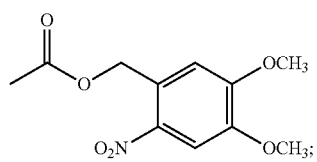

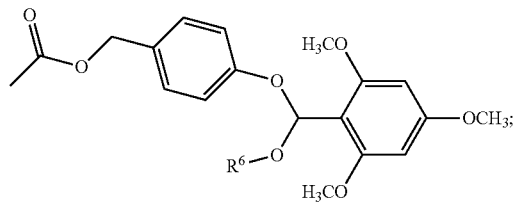

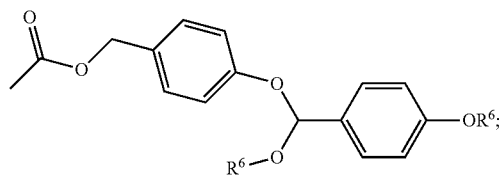

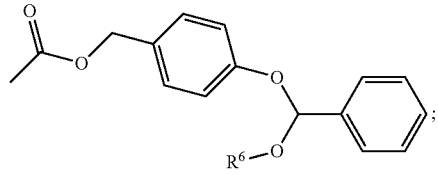

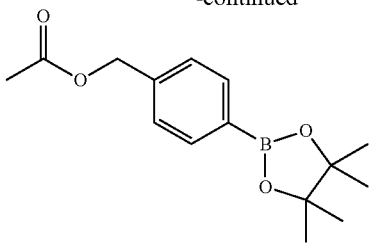

(sensitive to mildly oxidizing conditions such as $H_2O_2$);

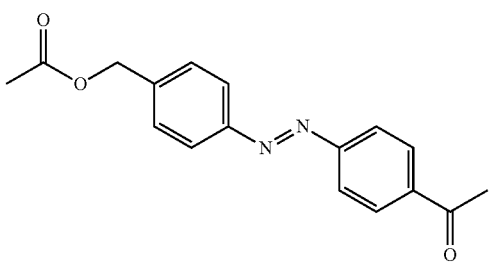 [SMILES: CC(=O)OCc1ccc(/N=N/c2ccc(C(C)=O)cc2)cc1]

(sensitive to reducing conditions or the enzyme azoreductase); and

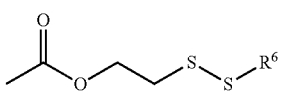

(sensitive to reducing conditions), wherein R$^6$ is optionally substituted $C_{1-20}$ linear or branched alkyl, optionally substituted $C_{6-20}$ aryl,

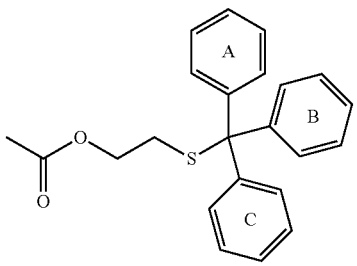

(sensitive to mild acid i.e., pH 4 to 6.5)

wherein each of rings A, B and C is, independently of the other of the rings, optionally substituted at one or more, including all, para- and ortho-positions with an electron-donating group. Preferred electron-donating groups are C1-C20 alkoxy, including methoxy, ethoxy, propoxy and butoxy, and dialkylamino wherein the two amino groups are the same or different and are C1-C20 alkyl, straight-chain or branched,

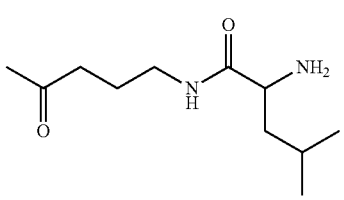

(sensitive to a peptidase such as leucine aminopeptidase),

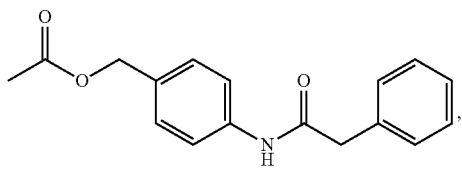 [SMILES: CC(=O)OCc1ccc(NC(=O)Cc2ccccc2)cc1]

(sensitive to penicillin-G amidase)

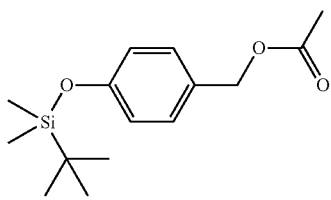 [SMILES: CC(=O)OCc1ccc(O[Si](C)(C)C(C)(C)C)cc1]

(sensitive to fluoride ion).

In embodiments, the polyglyoxylate polymer is a first polyglyoxylate polymer and the cap is a linker covalently attached to a second polyglyoxylate polymer.

In aspects, the linker is of the formula:

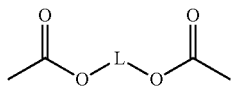

and L is a group that is cleaved in response to a stimulus such as light, enzymes, heat, change in pH or redox potential.

Examples of such linkers are:

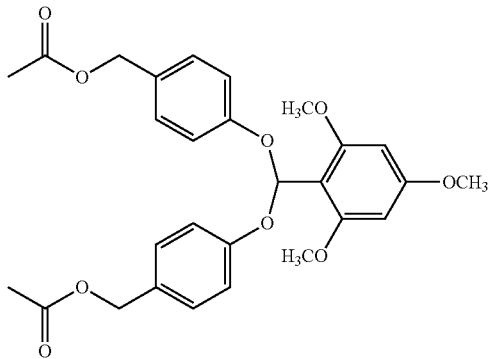 [SMILES: COc1cc(OC)c(C(Oc2ccc(COC(C)=O)cc2)Oc2ccc(COC(C)=O)cc2)c(OC)c1]

(sensitive to very mildly acidic pH (e.g., pH 6);

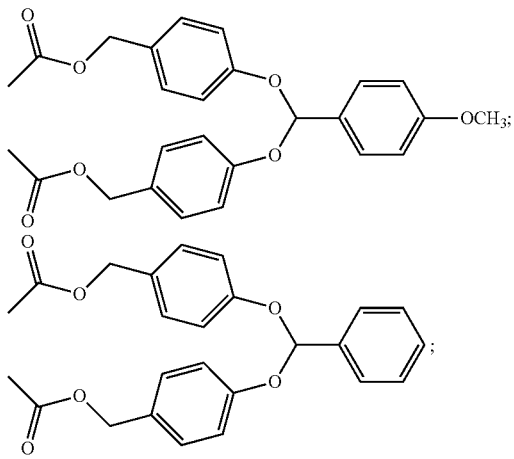

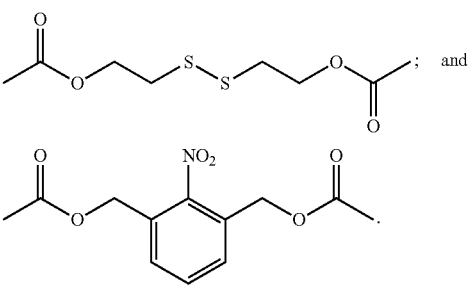

The invention includes block copolymers such as a block copolymer having first and second blocks, the first block being a polyglyoxylate polymer wherein: the blocks are linked to each other by a linker covalently attached to the first and second blocks; and upon exposure to a preselected stimulus, the covalent linkage of the linker to the first block is cleaved in preference to cleavage of bonds of the polyacetal backbone of the polymer of the first block.

An example of a linker of two blocks is:

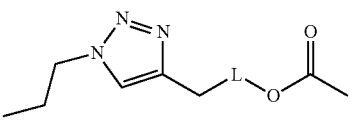

in which L is a group that is cleaved in response to a stimulus such as light, enzymes, heat, change in pH or redox potential.

More specific examples of linkers are:

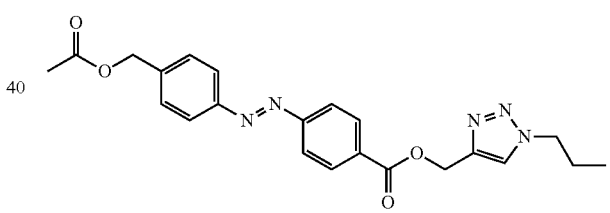

(sensitive to reducing conditions);

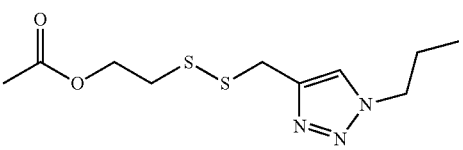 [SMILES: CCCn1cc(CSSCCOC(C)=O)nn1]

(sensitive to reducing conditions);

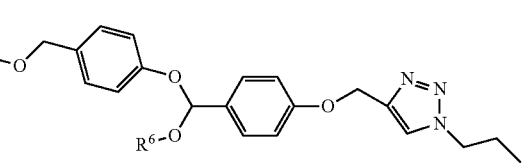

wherein $R^6$ is optionally substituted $C_{1-20}$ linear or branched alkyl, optionally substituted $C_{6-20}$ aryl; and

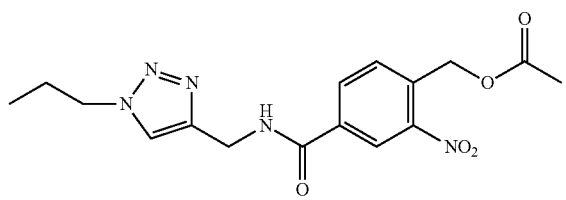 [SMILES: CCCn1cc(CNC(=O)c2ccc(COC(C)=O)c([N+](=O)[O-])c2)nn1]

(sensitive to light).

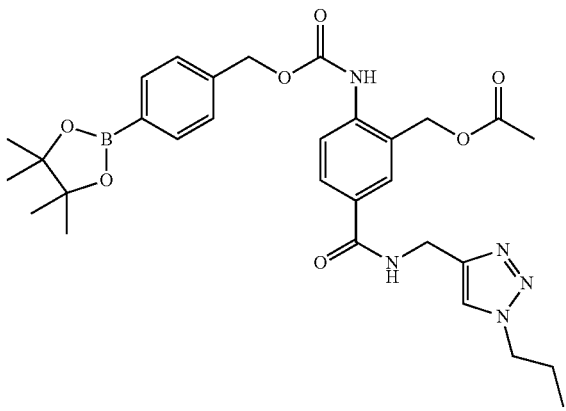 [SMILES: CCCn1cc(CNC(=O)c2ccc(NC(=O)OCc3ccc(B4OC(C)(C)C(C)(C)O4)cc3)c(COC(C)=O)c2)nn1]

(sensitive to oxidizing agents such as H₂O₂)

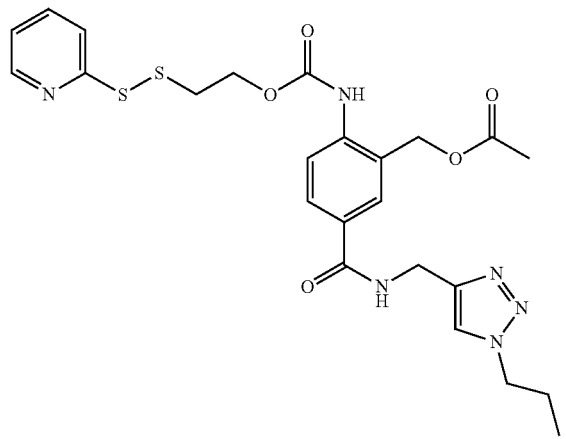 [SMILES: CCCn1cc(CNC(=O)c2ccc(NC(=O)OCCSSc3ccccn3)c(COC(C)=O)c2)nn1]

(sensitive to reducing agents such as thiols)

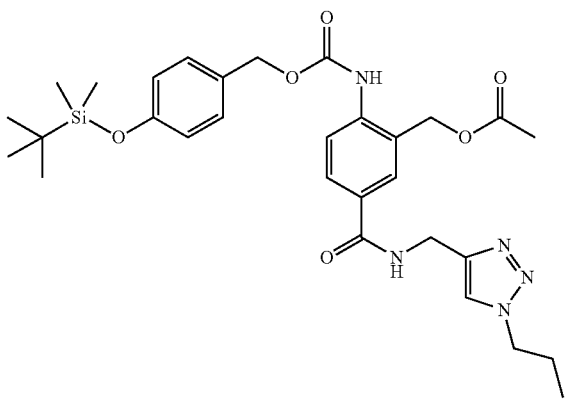 [SMILES: CCCn1cc(CNC(=O)c2ccc(NC(=O)OCc3ccc(O[Si](C)(C)C(C)(C)C)cc3)c(COC(C)=O)c2)nn1]

(sensitive to fluoride ion)

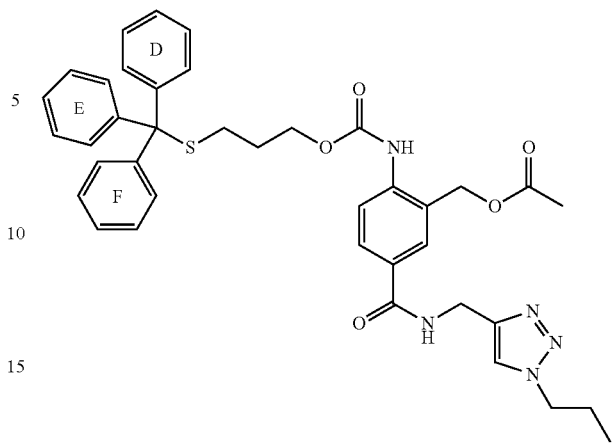

(sensitive to mild acid)

wherein each of rings D, E and F is, independently of the other of the rings, optionally substituted at one or more, including all, para- and ortho-positions with an electron-donating group. Preferred electron-donating groups are C1-C20 alkoxy, including methoxy, ethoxy, propoxy and butoxy, and dialkylamino wherein the two amino groups are the same or different and are C1-C20 alkyl, straight-chain or branched.

A block copolymer can have more than two blocks e.g., three blocks.

Blocks can be linked by a trivalent radical such as:

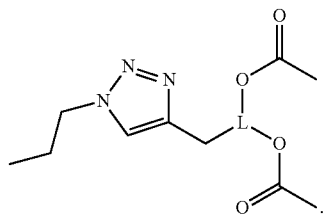

A particular example of a linker is:

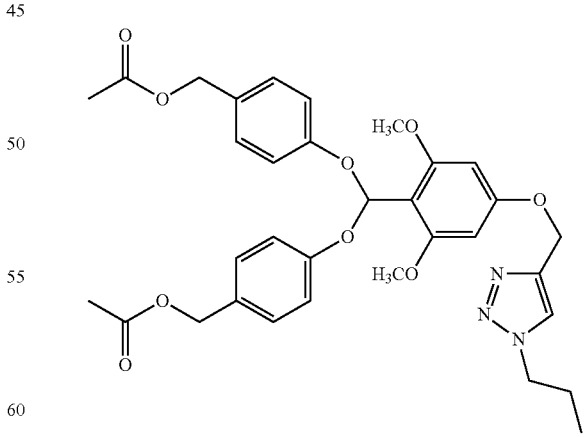

(sensitive to very mild acid).

Blocks are not limited to polyglyoxylates and can be, for example a PEG, a PDMAEMA, a poly(lactic acid), a poly (glycolic acid), a poly(lactic acid-co-glycolic acid), poly-caprolactone, and/or a poly(glyoxylic acid).

In another aspect, the invention is a method of making a polymer, the method comprising:

(1) oxidizing the 2,3-double bond of an ester of fumaric acid, maleic acid, or a combination thereof to form the corresponding oxoacetate; and (2) polymerizing the oxoacetate to form a polymer having a polyacetal backbone.

Step (1) can include subjecting the ester to ozonolysis, and may further include quenching the ozonide formed during ozonolysis with dimethyl sulfide. Step (2) can include polymerizing first and second oxoacetates to form a polymer having mixed subunits.

In preferred embodiments, the method includes the step of covalently attaching caps on the ends of the polymer formed in step (2).

The ester is preferably a diester, and example of which has the formula RO—(O)CH=CH(O)—OR.

The invention also includes a method of preparing an oxoacetate of the formula:

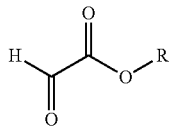

wherein R is as defined in claim 10, the method comprising:

(i) subjecting a diester of fumaric acid, maleic acid, or a combination thereof to ozonolyis; and (ii) quenching the ozonide formed during ozonolysis with dimethyl sulfide.

The invention includes an oxoacetate of the formula:

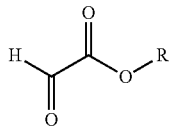

wherein R is optionally substituted $C_{3-20}$ linear or branched alkyl, or as defined in any of paragraphs (iii) to (xiii) as set out above.

DETAILED DESCRIPTION

General Procedures and Materials

Figure 1:
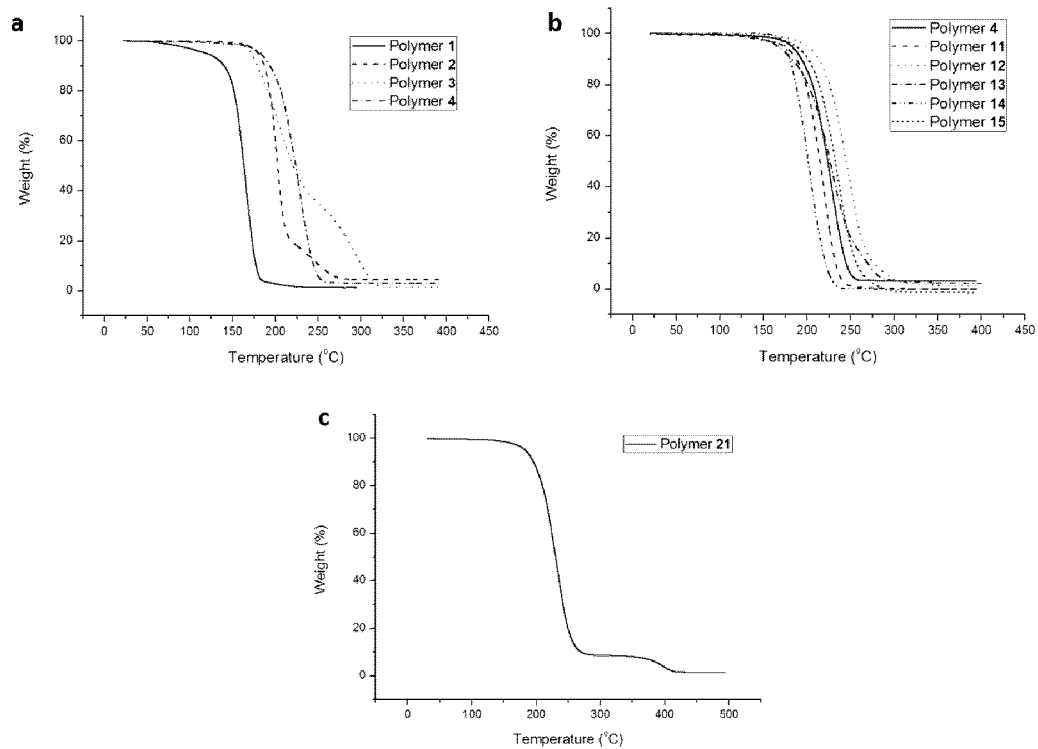
FIG. 1 shows (a) TGA results of different end-capped PEtGs 1-4. This shows that end-capped polyglyoxylates are more thermally stable than the uncapped polymer; (b) TGA results of different polyglyoxylates end-capped by NVOC-Cl showing that they are thermally stable and therefore well end-capped; and (c) TGA result of block polymer showing a two stage decomposition characteristic of the polymer being composed of two blocks.

Ethyl glyoxylate in toluene solution (50% w/w), phenyl isocyanate, dibutyltin dilaurate (DBTL), benzyl chloroformate, 4-dimethylaminopyridine (DMAP), 4-bromomethyl-3-nitrobenzoic acid, methanesulfonyl chloride and benzyl bromide were obtained from Alfa Aesar (Canada). Fumaric acid and maleic acid were purchased from Acros Organics (USA). 6-Nitroveratryl chloroformate (NVOC-Cl) was obtained from Chem-Impex International, Inc. (USA). Propargyl amine was purchased from AK Scientific, Inc. (USA). 4-(Hydroxymethyl)phenylboronic acid pinacol ester and hydrogen peroxide solution (50 wt %) in water, hydrazine hydrate, dimethyl sulfide, sodium azide ($NaN_3$), tin (II) chloride dehydrate, phosgene solution (15 wt. % in toluene), nile red and poly(ethylene glycol) methyl ether (MW=5000 g/mol, 2000 g/mol and 750 g/mol) were purchased from Sigma-Aldrich (USA). 1-Ethyl-3-(3-dimethylaminopropyl) carbodiimide hydrochloride (EDC.HCl) was purchased from Creo Salus (USA). Thionyl chloride (Alfa Aesar) was distilled under argon prior to use. Triethylamine ($Et_3N$), pyridine, and dichloromethane were distilled from calcium hydride before use. Anhydrous tetrahydrofuran (THF) and N,N-dimethylformamide (DMF) were obtained from a solvent purification system using aluminum oxide columns. All the other chemicals were of reagent grade and used without further purification. $^1$H NMR spectra were obtained in $CDCl_3$ at 400 MHz or 600 MHz on Varian Inova instruments. NMR chemical shifts (δ) are reported in ppm and are calibrated against residual solvent signals of $CDCl_3$ (δ 7.27), acetonitrile-$d_3$ (δ 1.94), DMSO-$d_6$ (δ 2.50) or deuterium oxide (δ 4.75). Fourier transform infrared spectra (FT-IR) were obtained using a Bruker tensor 27 instrument with films drop cast from $CH_2Cl_2$ on KBr plates. High-resolution mass spectrometry (HRMS) was performed using a Finnigan MAT 8400 electron impact (EI) mass spectrometer. The SEC instrument was equipped with a Viscotek GPC Max VE2001 solvent module. Samples were analyzed using the Viscotek VE3580 RI detector operating at 30° C. The separation technique employed two Agilent Polypore (300×7.5 mm) columns connected in series and to a Polypore guard column (50×7.5 mm). Samples were dissolved in THF (glass distilled grade) in approximately 5 mg/mL concentrations and filtered through 0.22 μm syringe filters. Samples were injected using a 100 μL loop. The THF eluent was filtered and eluted at 1 ml/min for a total of 30 minutes. A calibration curve was obtained from Polystyrene samples with molecular weight ranges of 1,540-1,126,000/mol Differential scanning calorimetry (DSC) and thermogravimetric analysis (TGA) were performed on a Mettler Toledo DSC 822e. For TGA the heating rate was 10° C./min between 50-400° C. under nitrogen. For DSC, the heating/cooling rate was 10° C./min from −100 to +17° C. Glass transition temperatures were obtained from the second heating cycle. Ultrapure water was obtained from a Barnstead EASYpure II system. Dialyses were performed using Spectra/Por regenerated cellulose membranes with 3500 g/mol MWCO.

Synthesis of Monomers

Synthesis of Dimethyl Maleate (5)

Maleic acid (25.0 g, 216 mmol) was dissolved in methanol (250 mL). Concentrated sulfuric acid (2.5 mL) was then added dropwise. After refluxing at 75° C. for 16 hours, the methanol was removed by rotary evaporator. Ethyl acetate (100 mL) was then added to the residue, and the solution was washed twice with saturated sodium bicarbonate (20 mL), and then with deionized water (20 mL). The organic layer was then dried over $MgSO_4$, filtered and concentrated under reduced pressure to provide a clear, colorless, oily liquid (30.0 g, 97%) after distillation of the oil at 140° C. (190 mbar). $^1$H NMR (400 MHz, $CDCl_3$): δ 6.26 (s, 2H), 3.79 (s, 6H). Spectral data are consistent with published values.[25]

Synthesis of Dibutyl Fumarate (6)

Fumaric acid (20.0 g, 172 mmol) was dissolved in n-butanol (250 mL). Concentrated sulfuric acid (2.5 mL) was then added dropwise. After stirring at 120° C. for 16 hours, the residual n-butanol was removed in vacuo. Ethyl acetate (100 mL) was then added to the residue, and the solution was washed with saturated sodium bicarbonate (20 mL) solution twice, and deionized water (20 mL) once. The organic layer was then dried over $MgSO_4$, filtered and concentrated under reduced pressure to provide a clear, colorless, oily liquid (36.8 g, 94%) after distillation at 100° C. (40 mbar). $^1$H NMR (400 MHz, $CDCl_3$): δ 6.85 (s, 2H), 4.20 (t, J=6.6 Hz, 4H), 1.63-1.70 (m, 4H), 1.36-1.46 (m, 4H), 0.95 (t, J=7.4 Hz, 6H). Spectral data are consistent with published values.[26]

Synthesis of Dibenzyl Fumarate (7)

Fumaric acid (10.0 g, 86 mmol, 1.0 equiv.) was dissolved in anhydrous DMF (200 mL), and then triethylamine (24.0 mL, 172 mmol, 2.0 equiv.) was added dropwise to the stirring solution. Benzyl bromide (19.5 mL, 164 mmol, 1.9 equiv.) was then injected into the reaction mixture. After stirring at 100° C. for 16 hours, the solution was precipitated into deionized water (800 mL) to provide a pale yellow solid (18.8 g, 78%) after filtration and drying. $^1$H NMR (400 MHz, $CDCl_3$): δ 7.31-7.41 (m, 10H), 6.94 (s, 2H), 5.24 (s, 4H). Spectral data are consistent with published values.[27]

Synthesis of Methyl Glyoxylate (8)

Diester 5 (20.0 g, 139 mmol, 1.0 equiv.) was dissolved in dichloromethane (200 mL), and the solution was cooled to −78° C. in a dry ice/acetone bath. Ozone was bubbled into the solution under stirring until the solution turned blue. The solution was then purged with oxygen. Dimethyl sulfide (12.2 mL, 167 mmol, 1.2 equiv.) was added dropwise to quench the system. After stirring for 5 hours, and warming to room temperature, the solvent and residual dimethyl sulfide were removed by distillation at 70° C. under argon. A pale yellow liquid (18.3 g, 75%) was obtained via distillation at 100° C. under a slightly reduced pressure. $^1$H NMR (400 MHz, CDCl$_3$): δ 9.33 (s, 1H), 3.86 (s, 3H). Spectral data are consistent with published values.[28]

Synthesis of n-Butyl Glyoxylate (9)

Diester 6 (26.0 g, 114 mmol, 1.0 equiv.) was dissolved in dichloromethane (300 mL), and the solution was cooled to −78° C. in dry ice/acetone bath. Ozone was bubbled into the solution under stirring until the solution turned into blue, and then the solution was purged with oxygen. Dimethyl sulfide (10.0 mL, 137 mmol, 1.2 equiv.) was then added dropwise to quench the system. After stirring for 5 hours, and warming to room temperature, the solvent and the residual dimethyl sulfide were removed by distillation at 70° C. under argon. A pale yellow liquid (15.3 g, 52%) was obtained after distillation at 150° C. (200 mbar) over P$_2$O$_5$. $^1$H NMR (400 MHz, CDCl$_3$): δ 9.39 (s, 1H), 4.31 (t, J=6.6 Hz, 3H), 1.68-1.76 (m, 2H), 1.37-1.47 (m, 2H), 0.94 (t, J=7.4 Hz, 3H). $^{13}$C NMR (150 MHz, DMSO-d$_6$): δ 184.2, 159.7, 65.3, 30.0, 18.6, 13.4. MS calc'd. for C$_6$H$_{10}$O$_3$, 130.06299; calc'd. for [M+H]$^+$, 131.07082. found, 131.07088.

Synthesis of Benzyl Glyoxylate (10)

Diester 7 (10.0 g, 34 mmol, 1.0 equiv.) and Sudan Red III (20.0 mg) were dissolved in dichloromethane (100 mL), and the solution was cooled to −78° C. by dry ice/acetone bath. Ozone was then bubbled into the stirred solution until the red solution turned clear and colorless, and then the solution was immediately purged with oxygen. Dimethyl sulfide (3.0 mL, 41 mmol, 1.2 equiv.) was then added dropwise into the solution to quench the ozonide. The mixture was stirred for an additional 5 hours, and allowed to warm to ambient temperature. The solvent and the residual dimethyl sulfide were then removed by distillation at 70° C. under argon to provide a pale yellow liquid (6.0 g, 55%) following distillation at 150° C. (40 mbar) from P$_2$O$_5$. $^1$H NMR (400 MHz, CDCl$_3$): δ 9.43 (s, 1H), 7.21-7.51 (m, 5H), 5.35 (s, 2H). Spectral data are consistent with published values.[29]

Synthesis of Bis(2-Hydroxyethyl) Fumarate (35)

Fumaric acid (63 g, 540 mmol) was dissolved in a round bottom flask containing ethylene glycol (220 mL, 3.9 mol). A catalytic amount of p-toluene sulfonic acid (2.5 g, 13 mmol) was added. The reaction mixture was then heated to 125° C. in an oil bath, with stirring for 8 hours. The reaction was then cooled to ambient, and triethylamine (10 g, 99 mmol) was added. The mixture was then distilled under reduced pressure (0.1 mbar) in an oil bath at 75-80° C. to reduce the solvent volume. Once the drip rate has slowed considerably, the heat is removed and the flakes allowed to cool to provide the product in >95% purity as a white powder. Isolated product: white powder; Rf=0.38 (17:3 ethyl acetate:hexanes); $^1$H NMR (600 MHz, CDCl$_3$): δ 6.88 (s, 2H), 4.34-4.31 (m, 4H), 3.88-3.85 (m, 4H), 3.03 (br s, 2H); $^{13}$C NMR (150 MHz, CDCl$_3$): δ 165.1, 133.6, 66.8, 60.6; HRMS (CI): Calculated for C$_8$H$_{13}$O$_6$ (M+H)$^+$: 205.0712. Found: 205.0717.

Synthesis of Bis (2-Tert-Butyl-Dimethylsiloxyethyl) Fumarate (36)

Bis(2-hydroxyethyl) fumarate (20 g, 120 mmol) and imidazole (28 g, 410 mmol) were dissolved in anhydrous CH$_2$Cl$_2$ (200 mL). TBDMSCl (50 g, 330 mmol) solution was then added portionwise and the solution was then allowed to stir for 16 hours. The reaction mixture was then diluted with CH$_2$Cl$_2$ (200 mL) and washed successively with saturated ammonium chloride (100 mL×2), saturated sodium bicarbonate (100 mL×2), and brine (1×50 mL) prior to being dried, filtered and concentrated in the usual fashion. The residue was then concentrated further under high vacuum (0.06 mbar) at 45° C. The resulting white crystals were then filtered, washed with ice-cold isopropanol, and dried in vacuo. The mother liquor was crystallized a second time to provide a total mass of 41 g of the product as white crystals in 82% yield over two steps. Clear, colourless crystals; $^1$H NMR (600 MHz, CDCl$_3$): δ 6.89 (s, 2H), 4.29-4.25 (m, 4H), 3.88-3.84 (m, 4H), 0.89 (s, 18H), 0.07 (s, 12H); $^{13}$C NMR (150 MHz, CDCl$_3$): δ 164.9, 133.6, 66.6, 61.0, 25.8, 18.3, −5.3. HRMS (CI) Calculated for C$_{20}$H$_{40}$O$_6$Si$_2$: 432.2363. Calculated for C$_{20}$H$_{41}$O$_6$Si$_2$ (M+H)$^+$: 433.2442. Found: 433.2461.

Synthesis of Bis(Propargyl) Fumarate (38)

Propargyl alcohol (Sigma-Aldrich, 16.9 mL, 292.3 mmol) was dissolved in anhydrous dichloromethane (600 mL) in a two-necked round-bottomed flask equipped with a stir bar and a 100 mL dropping funnel. DIPEA (61 mL, 348 mmol) was added, and the mixture cooled to 0° C. A solution of fumaryl chloride[30] (15.0 mL, 139.2 mmol) in CH$_2$Cl$_2$ (30 mL) was added dropwise over 45 minutes. The reaction mixture was allowed to warm to room temperature and stirred for 16 hours, then warmed to 45° C. and stirred for an additional 24 hours. The reaction mixture was then cooled to ambient and washed with sequentially with saturated ammonium chloride (3×250 mL), saturated sodium bicarbonate (2×240 mL) and brine (1×80 mL) before being dried filtered and concentrated in the usual manner. This provided 30 g of crude material as a dark brown oil that was purified by flash column chromatography (4:1, hexanes-ethyl acetate) to provide 19.2 g of product in 72% yield as an off-white amorphous solid.

Off white amorphous solid, Rf=0.78 (7:3 hexanes-ethyl acetate); $^1$H NMR (600 MHz, CDCl$_3$): δ 6.91 (s, 2H), 4.79 (d, J=2.5 Hz, 4H), 2.52 (t, J=2.5 Hz, 2H). HRMS (EI) Calculated for C$_{10}$H$_8$O$_4$: 192.0423. Calculated for C$_{10}$H$_9$O$_4$ (M+H)$^+$: 193.0501. Found: 193.0492. Spectral data is consistent with published data.[31]

Synthesis of Bis-(2-(Ethoxycarbonyl)Phenyl) Fumarate (40)

Ethyl salicylate 39a (6.5 g, 39.0 mmol, 5.7 mL) was dissolved in anhydrous CH$_2$Cl$_2$ (100 mL) under nitrogen and cooled to 0° C. Diisopropylethylamine (DIPEA, 4.8 g, 6.5 mL, 37.2 mmol) was then added in one batch and fumaryl chloride (2.0 mL, 18.6 mmol) was then added dropwise. Following full addition, the reaction was then allowed to warm to ambient, and stirred for 24 hours, then warmed to 40° C. and stirred for an additional 24 hours. The reaction was monitored by TLC (4:1 hexanes:ethyl acetate) and once the reaction ceased to progress further, the reaction mixture was quenched by the addition of water (30 mL) and saturated ammonium chloride (30 mL). The reaction mixture was then further diluted with CH$_2$Cl$_2$, the phases separated, and the combined organic phases, washed sequentially with saturated sodium bicarbonate and brine before drying with magnesium sulfate, filtration through a cotton plug, and concentration under reduced pressure. Column chromatography of the resulting purple solid provided the title compound as white crystals (7.6 g) in 98% yield. Colourless crystals; Rf=0.4 (4:1 hexanes:ethyl acetate); $^1$H NMR (600 MHz, CDCl$_3$): $\delta_{ppm}$ 8.08 (dd, J=7.84, 1.65 Hz, 2H), 7.61 (ddd, J=7.92, 7.81, 1.71 Hz, 2H), 7.37 (ddd, J=7.73, 7.72, 1.09 Hz, 2H), 7.31 (s, 2H), 7.18 (dd, J=8.08, 0.91 Hz, 2H), 4.33 (q, J=7.15 Hz, 4H), 1.36 (t, J=7.14 Hz, 6H); $^{13}$C NMR (150 MHz, CDCl$_3$): $\delta_{ppm}$ 164.3, 163.3, 149.9, 134.3, 133.9, 131.9, 126.5, 123.5, 61.3, 14.2.

Synthesis of Bis-(4-N-Acetylphenyl) Fumarate (41)

Acetaminophen (39b) (5.9 g, 39.0 mmol) was dissolved in anhydrous DMF (50 mL) with magnetic stirring under nitrogen. Once dissolved, CH$_2$Cl$_2$ (50 mL) was added and the mixture cooled to 0° C. DIPEA (6.5 mL, 4.8 g, 37.2 mmol) was then added at once. Fumaryl chloride (2 mL, 2.84 g, 18.6 mmol) was then added dropwise to the solution, and the reaction was then allowed to warm to ambient, and stirred for 24 hours, then warmed to 40° C. and stirred for an additional 24 hours. The reaction was monitored by TLC (8:1 ethyl acetate:hexanes) and once the reaction ceased to progress further, the reaction mixture was quenched by the addition of water (30 mL) and saturated ammonium chloride (30 mL). The reaction was then diluted with ethyl acetate and the two phases were separated. The organic phase was then washed with 1 M HCl before being partially concentrated, and filtered. The solid was washed with water and ethyl acetate. Similarly, the combined aqueous phases were likewise filtered and the solid washed with water. The combined solids were then dried in vacuo to provide the title compound as an off-white amorphous solid in 73% yield with no further purification required (5.2 g). Off-white amorphous solid; Rf=0.24 (8:1 ethyl acetate:hexanes); $^1$H NMR (600 MHz, DMSO-d6): $\delta_{ppm}$ 10.10 (s, 2H), 7.65 (d, J=8.96 Hz, 4H), 7.17 (d, J=8.94 Hz, 4H), 7.15 (s, 2H), 2.05 (s, 6H); $^{13}$C NMR (150 MHz, DMSO-d6): $\delta_{ppm}$. 168.8, 163.6, 145.6, 137.8, 134.3, 122.1, 120.3.

Synthesis of Propargyl Glyoxylate (28)

Propargyl fumarate (35f, 7.3 g, 38 mmol) was dissolved in 400 mL (4:1, acetone-acetonitrile) and cooled to −60° C. Ozone was bubbled through the solution as the reaction continued to cool to −78° C. Ozone was bubbled through for 35 minutes in total (reaction colour fades from yellow to grey). Oxygen was then bubbled through the reaction mixture for 15 minutes. Dimethyl sulfide (4.0 mL, 54.5 mmol) was then added and the reaction mixture was allowed to warm to ambient with stirring for twelve hours.

The reaction was then concentrated to dryness. The mixture was resuspended in ethyl acetate and extracted thrice with ice cold water. The combined organics were dried with magnesium sulfate, filtered and concentrated. This mixture was then distilled under vacuum three times successively, the latter two times in the presence of phosphorous pentoxide (bp=78-84° C., 60 mbar), to provide 2.8 g of the title compound as a pale yellow oil. $^1$H NMR (600 MHz, CDCl$_3$): $\delta_{ppm}$ 9.75 (s, 1H), 4.85 (d, J=2.6 Hz, 2H), 2.55 (t, J=2.5 Hz, 1H).

2-(Tert-Butyldimethylsiloxy)Ethyl Glyoxylate (30)

The TBS-protected fumarate (36, 11.0 g, 25.5 mmol) was dissolved in dichloromethane (280 mL) and cooled to −78° C. Ozone was bubbled through the solution for 12 minutes at which time a deep blue colour persisted. Oxygen was then bubbled through the solution for 10 minutes, and dimethyl sulfide (1.9 g, 2.3 mL, 30.5 mmol) was added and the reaction mixture was allowed to warm to ambient with stirring over 12 hours. The Solvent was then removed under reduced pressure, and the DMSO was removed by distillation under high vacuum. Phosphorous pentoxide was then added and the material was distilled thrice successively using a variable heating mantle. The product boiled at 75-79° C., and in the final distillation was collected in a flask cooled to −78° C. in a dry ice bath providing approximately 5 mL of product (approximately 50% yield) as a clear oil. The product was kept frozen in a dry ice bath until used for polymerization. $^1$H NMR (600 MHz, CDCl$_3$): $\delta_{ppm}$ 9.38 (s, 1H), 4.36-4.33 (m, 2H), 3.88-3.85 (m, 2H), 0.84 (s, 9H), 0.03 (s, 6H); $^{13}$C NMR (100 MHz, CDCl$_3$): $\delta_{ppm}$ 183.5, 159.3, 67.5, 60.6, 25.7, 18.2, −5.4. HRMS (EI) Calculated for C$_{10}$H$_{20}$O$_4$Si: 232.1131. Calculated for C$_{10}$H$_{21}$O$_4$Si: 233.1209. Found: 233.1206.

Synthesis of 2-(Ethoxycarbonyl)Phenyl) Glyoxylate (31)

Bis-(2-(ethoxycarbonyl)phenyl) fumarate (40) (3.7 g, 9.0 mmol) was dissolved in CH$_2$Cl$_2$ and cooled to −78° C. Sudan III (2 mg) was added. Ozone was bubbled through the reaction mixture until the deep red colour transitioned to a yellow indicating consumption of the indicator (approximately 10 minutes). Oxygen was then bubbled through the reaction for five minutes, and then dimethyl sulfide (1.0 mL, 14.4 mmol) was added and the reaction was degassed under vacuum and then allowed to warm slowly to ambient and stirred for 16 hours under nitrogen. Solvent was then removed. Crude NMR shows the formation of oligomeric glyoxylates (see text above). The mixture was redissolved in chloroform, and phosphorous pentoxide (500 mg) was added and the mixture stirred at 4° C. for 96 hours. Chloroform was removed and the solid material was heated to 160° C. to crack oligomers before being vacuum distilled (b.p.=120-123° C., 0.5 mbar) to provide 2.3 g of the product as a thick yellow oil in 60% yield. Reaction is unoptimized. Yellow oil; $^1$H NMR (600 MHz, CDCl$_3$): $\delta_{ppm}$ 9.61 (s, 1H), 8.10 (dd, J=7.9, 1.7 Hz, 1H), 7.62 (ddd, J=8.1, 7.6, 1.7 Hz, 1H), 7.39 (dt, J=7.6, 7.6, 1.2 Hz, 1H), 7.19 (dd, J=8.1, 1.2 Hz, 1H), 4.29 (q, J=7.1 Hz, 2H), 1.32 (t, J=7.15 Hz, 3H); $^{13}$C NMR (150 MHz, CDCl$_3$): $\delta_{ppm}$ 182.6, 136.9, 157.6, 149.6, 134.1, 132.1, 126.9, 123.0, 122.4, 61.4, 14.1. HRMS (ESI) Calculated for C$_{11}$H$_{10}$O$_5$: 222.0528. Calculated for C$_{11}$H$_{10}$NaO$_5$ (M+Na)$^+$: 245.0426. Found: 245.0451.

Synthesis of 4-N-Acetylphenyl Glyoxylate (32)

Bis-(4-N-acetylphenyl) fumarate (6.6 g, 17.3 mmol) was dissolved in DMF (60 mL) and 20 mL of CH$_2$Cl$_2$ was added. The mixture was cooled to −78° C. and ozone was bubbled through the reaction mixture until the solution turned blue (Sudan III proved to be an inaccurate indicator, being consumed before the reaction was complete), approximately 30 minutes. The reaction was then degassed with oxygen for 15 minutes, and then dimethyl sulfide (1.7 mL, 22.5 mmol) was added and the reaction mixture was allowed to warm with stirring over 16 hours under nitrogen. The solvent was then removed, and the material was distilled under vacuum (b.p.=180° C., 0.5 mbar) to provide the product as a thick brown oil. Brown oil; $^1$H NMR (600 MHz, DMSO-d6): $\delta_{ppm}$ 11.18 (bs, 1H), 10.06 (s, 1H), 7.62 (d, J=9.04 Hz, 2H), 7.14 (d, J=9.01 Hz, 2H), 2.03 (s, 3H); $^{13}$C NMR (150 MHz, CDCl$_3$): $\delta_{ppm}$ 185.5, 168.8, 158.1, 145.4, 138.0, 121.9, 120.4, 24.4. HRMS (ESI) Calculated for C$_{10}$H$_9$NO$_4$: 207.0532. Calculated for C$_{11}$H$_{10}$NaNO$_5$ (M+Na)$^+$: 230.0429. Found: 230.0418.

Synthesis of End-Caps/Linkers

Synthesis of Propargyl Amide 17

Compound 16[32] (580 mg, 2.9 mmol, 1 equiv.) was dissolved in solvent (12 mL of 5:1 dichloromethane:pyridine), then EDC.HCl (690 mg, 3.5 mmol, 1.2 equiv.), propargyl amine (1.1 mL, 17.7 mmol, 6 equiv.) and DMAP (430 mg, 3.5 mmol, 1.2 equiv.) were added into the stirring mixture under argon. After stirring at room temperature for 6 hours, the reaction was diluted with ethyl acetate (60 mL) and washed with saturated NaHCO$_3$ solution (1×30 mL), 1M HCl (3×30 mL) and deionized water (1×30 mL) successively. The organic phase was dried with MgSO$_4$, filtered and the solvent removed under reduced pressure to yield compound 17 (395 mg, 57%) as a brown solid. $^1$H NMR (400 MHz, DMSO-d$_6$): δ 9.26 (t, J=5.3 Hz, 1H), 8.53 (d, J=1.2 Hz, 1H), 8.22 (dd, J=7.6 Hz, 1.2 Hz, 1H), 7.94 (d, J=7.6 Hz, 1H), 5.67 (t, J=5.3 Hz, 1H), 4.87 (d, J=5.3 Hz, 2H), 4.09 (dd, J=5.3 Hz, 2.4 Hz, 2H) 3.16 (t, J=2.4 Hz, 1H). $^{13}$C NMR (150 MHz, CDCl$_3$): δ 163.7, 146.4, 141.6, 133.0, 132.0, 128.4, 123.1, 80.7, 73.0, 59.8, 28.6. MS calc'd for C$_{11}$H$_{10}$O$_4$N$_2$, 234.0641. found, 234.0642.

Synthesis of Chloroformate 18

Compound 17 (390 mg, 1.6 mmol, 1.0 equiv.) was dissolved in THF (7 mL). The resulting solution was then added dropwise into a phosgene solution (15 wt. % in toluene, 3.5 mL, 4.8 mmol, 3.0 equiv.) under an argon atmosphere at room temperature and was stirred for 40 hours. The residual phosgene and solvent was then removed by high vacuum to yield compound 18 (482 mg 98%) as a brown solid. Phosgene collected in the liquid nitrogen-cooled trap was then quenched with methanol (10 mL) and saturated sodium hydroxide solution (10 mL). $^1$H NMR (400 MHz, CDCl$_3$): δ 8.59 (d, J=2.0 Hz, 1H), 8.17 (dd, J=8.2 Hz, 2.0 Hz, 1H), 7.79 (d, J=8.2 Hz, 1H), 6.36 (s, 1H), 5.81 (s, 2H), 4.31 (dd, J=5.1 Hz, 2.3 Hz, 2H) 2.35 (t, J=2.3 Hz, 1H). $^{13}$C NMR (150 MHz, CDCl$_3$): δ 164.1, 150.6, 135.49, 133.4, 132.8, 132.3, 129.5, 124.1, 78.8, 72.8, 69.1, 30.4. MS calc'd for C$_{12}$H$_9$O$_5$N$_2$Cl, 296.0200. found, 296.0201.

Synthesis of Chloroformate 45.

4-(Hydroxymethyl)phenylboronic acid pinacol ester, compound 42 (800 mg, 3.4 mmol, 1.0 equiv.) was dissolved in THF (7 mL). The resulting solution was then added dropwise into a phosgene solution (15 wt % in toluene, 7.5 mL, 10.3 mmol, 3.0 equiv.) under an argon atmosphere at room temperature and was stirred for 24 h. The residual phosgene and solvent were then removed by high vacuum to yield chloroformate 45 (920 mg, 91%) as a pale brown liquid. Phosgene collected in the liquid nitrogen-cooled trap was then quenched with methanol (20 mL) and saturated sodium hydroxide solution (20 mL). $^1$H NMR (400 MHz, CDCl$_3$): δ 7.86 (d, J=8.2 Hz, 2H), 7.39 (d, J=8.2 Hz, 2H), 5.32 (s, 2H), 1.36 (s, 12H). Spectral data are consistent with published values.[33]

Synthesis of Chloroformate 46.

Compound 43[34] (500 mg, 2.7 mmol, 1.0 equiv.) was dissolved in THF (10 mL). The resulting solution was then added dropwise into a phosgene solution (15 wt % in toluene, 5.8 mL, 8.1 mmol, 3.0 equiv.) under an argon atmosphere at room temperature and was stirred for 24 h. The residual phosgene and solvent were then removed by high vacuum to yield chloroformate 46 (750 mg, 98%) as a pale brown liquid. Phosgene collected in the liquid nitrogen-cooled trap was then quenched with methanol (20 mL) and saturated sodium hydroxide solution (20 mL). $^1$H NMR (400 MHz, CDCl$_3$): δ 8.81 (s, 1H), 8.26 (t, J=7.0 Hz, 1H), 8.17 (d, J=8.2 Hz, 1H) 7.69 (t, J=7.0 Hz, 1H), 4.61 (t, J=5.9 Hz, 2H), 3.34 (t, J=5.9 Hz, 2H). $^{13}$C NMR (150 MHz, CDCl$_3$): δ 156.9, 150.5, 145.2, 142.9, 125.0, 123.9, 68.8, 37.8. MS calc'd. for [M]$^+$ C$_8$H$_8$ClNO$_2$S$_2$: 248.9685. found: 248.9689.

Synthesis of Chloroformate 47.

Compound 44[35] (200 mg, 0.84 mmol, 1.0 equiv.) was dissolved in THF (8 mL). The resulting solution was then added dropwise into a phosgene solution (15 wt % in toluene, 1.8 mL, 2.5 mmol, 3.0 equiv.) under an argon atmosphere at room temperature and was stirred for 24 h. The residual phosgene and solvent were then removed by high vacuum to yield chloroformate 47 (230 mg, 91%) as a pale brown liquid. Phosgene collected in the liquid nitrogen-cooled trap was then quenched with methanol (20 mL) and saturated sodium hydroxide solution (20 mL). $^1$H NMR (400 MHz, CDCl$_3$): δ 8.02 (d, J=8.2 Hz, 1H), 8.00 (d, J=8.8 Hz, 1H), 7.85 (d, J=8.8 Hz, 1H), 7.59 (d, J=8.2 Hz, 1H), 5.40 (s, 2H).

Synthesis of Compound 51

Compound 17 (630 mg, 2.86 mmol, 1 equiv.) and tin (II) chloride dehydrate (4.24 g, 14.36 mmol, 5 equiv.) were dissolved into a 39 mL solvent mixture (THF:water=10:3) and stirred at 70° C. with argon protection for 30 min. After cooling down to room temperature, the solution was poured into 50 mL cold water and be adjusted to pH 8.0 by 1 M sodium carbonate solution. Then the mixture was extracted by ethyl acetate (3×60 mL), The resulting organic phase was washed with brine once, and dried over anhydrous MgSO$_4$, filtered and the solvent was removed under reduced pressure to yield compound 51 (450 mg, 83%) as a yellow solid. $^1$H NMR (400 MHz, DMSO-d$_6$): δ 8.61 (t, J=5.3 Hz, 1H), 7.12 (d, J=7.6 Hz, 1H), 7.08 (d, J=1.8 Hz, 1H), 6.98 (dd, J=7.6 Hz, 1.8 Hz, 1H), 5.08 (t, J=5.3 Hz, 1H), 5.04 (s, 2H), 4.37 (d, J=5.3 Hz, 1H), 3.98 (dd, J=5.3 Hz, 2.4 Hz, 2H), 3.05 (t, J=2.4 Hz, 1H).

Synthesis of Compound 52

Compound 51 (430 mg, 2.26 mmol, 1 equiv.) was dissolved into 12 mL THF, 8 mL saturated sodium carbonate solution was then added. After the mixture was cool down to 0° C., chloroformate 45 (738 mg, 2.49 mmol, 1.1 equiv.) in 4 mL THF and 4 mL saturated sodium carbonate solution were added into the system dropwise at the same time. After stirring at room temperature for 1 hour, the mixture was diluted by 50 mL ethyl acetate, the organic phase was collected, washed with brine once, and dried over anhydrous MgSO4, filtered and the solvent was removed under reduced pressure, the product was further purified by column with 1:1=ethyl acetate and hexane as mobile phase to yield compound 52 (450 mg, 43%) as a yellow solid. $^1$H NMR (400 MHz, DMSO-d$_6$): δ 9.08 (s, 1H), 8.68 (t, J=5.1 Hz, 1H), 7.96 (s, 1H), 7.69 (d, J=8.2 Hz, 1H), 7.60 (dd, J=1.6 Hz, 8.2 Hz, 1H), 7.46 (d, J=7.8 Hz, 2H), 7.42 (d, J=7.8 Hz, 2H), 5.44 (t, J=5.5 Hz, 1H), 5.17 (s, 2H), 4.54 (d, J=5.5 Hz, 2H), 4.00 (dd, J=5.5 Hz, 2.3 Hz, 2H), 3.10 (t, J=2.3 Hz, 1H), 1.28 (s, 12H).

Synthesis of Chloroformate 53

Compound 52 (400 mg, 0.862 mmol, 1.0 equiv.) was dissolved in THF (4 mL). The resulting solution was then added dropwise into a phosgene solution (15 wt. % in toluene, 1.8 mL, 2.59 mmol, 3.0 equiv.) under an argon atmosphere at room temperature and was stirred for 16 hours. The residual phosgene and solvent was then removed by high vacuum to yield compound 53 (432 mg 95%) as a yellow solid. Phosgene collected in the liquid nitrogen-cooled trap was then quenched with methanol (10 mL) and saturated sodium hydroxide solution (10 mL). $^1$H NMR (400 MHz, CDCl$_3$): δ 8.06 (s, 1H), 7.75 (d, J=8.21 Hz, 2H), 7.64 (s, 1H), 7.61 (dd, J=7.6 Hz, 1.8 Hz, 1H), 7.52 (d, J=8.2 Hz, 1H), 7.45 (d, J=8.2 Hz, 2H), 7.35 (s, 1H), 5.38 (s, 2H), 5.23 (s, 2H), 4.12 (dd, J=5.3 Hz, 2.4 Hz, 2H), 2.48 (t, J=2.4 Hz, 1H), 1.33 (s, 12H).

Synthesis of Polymers

Due to the highly reactive nature of these monomers, even trace water can lead to oligomerization or polymerization. Therefore, immediately before polymerization, a second vacuum distillation with P$_2$O$_5$ was conducted to crack any oligomers and remove any remaining traces of water.

Polymerization of Ethyl Glyoxylate without End-Capping (Polymer 1)

Ethyl glyoxylate in toluene solution (20 mL) was fractionally distilled under vacuum (55° C., 125 mbar) over $P_2O_5$ to remove toluene and trace water in the first, discarded fraction. The residue was then distilled twice successively over $P_2O_5$ at atmospheric pressure under argon protection at 130° C. to obtain the highly pure monomer. This pale yellow liquid (5.0 mL, 50 mmol, 1.0 equiv.) was dissolved in dichloromethane (5.0 mL) and $Et_3N$ (3.5 µL, 25 µmol, 0.0005 equiv.). The solution was stirred for one hour at −20° C., and the resulting polymer was purified by precipitation into methanol. After drying in vacuo for 48 hours, a white, sticky polymer was obtained (1.8 g, 35%). $^1H$ NMR (400 MHz, $CDCl_3$): δ 5.48-5.75 (m, 100H), 4.12-4.38 (m, 204H), 1.24-1.44 (m, 298H). $^{13}C$ NMR (150 MHz, $CDCl_3$): δ 164.7-167.1, 90.6-93.8, 61.7, 13.5. SEC: $M_n$=103 kg/mol, $M_w$=266 kg/mol, PDI=2.6. $T_g$=−32° C.

Polymerization of Ethyl Glyoxylate with Phenyl Isocyanate as End-Cap (Polymer 2)

The same distillation and polymerization procedure was conducted to obtain poly(ethyl glyoxylate) as described for polymer 1; however, prior to precipitation, phenyl isocyanate (100 µL, 920 µmol, 0.018 equiv.) was added to end-cap the polymer along with 3 drops of DBTL. The solution was then stirred for 24 hours at room temperature and a further 16 hours at 40° C. Purification was achieved by precipitation of the crude reaction mixture into methanol. After decanting the excess methanol, the residue was dried in vacuo for 48 hours to provide 2.3 g of a white, sticky polymer in 45% yield. $^1H$ NMR (400 MHz, $CDCl_3$): δ 7.26-7.43 (m, 5H), 5.48-5.73 (m, 43H), 4.10-4.30 (m, 90H), 1.17-1.36 (m, 133H). $^{13}C$ NMR (150 MHz, $CDCl_3$): δ 164.7-166.9, 90.3-94.8, 61.7, 13.5. FT-IR (KBr, thin film): 2982, 1762, 1447, 1376, 1020 $cm^{-1}$. SEC: $M_n$=27 kg/mol, $M_w$=66 kg/mol, PDI=2.5. Tg=−1° C.

Polymerization of Ethyl Glyoxylate with Benzyl Chloroformate as End-Cap (Polymer 3)

Poly(ethyl glyoxylate) was prepared as described for polymer 1. Following polymerization, but prior to precipitation, benzyl chloroformate (100 µL, 710 µmol, 0.014 equiv.) was added at 0° C. along with $Et_3N$ (99.0 µL, 710 µmol, 0.014 equiv.). The solution was stirred for 24 hours at room temperature and a further 16 hours at 40° C. Purification was achieved by precipitation of the crude reaction mixture into methanol. After the solvent was decanted, the residue was dried in vacuo for 48 hours to provide 2.6 g of a white, sticky polymer in 50% yield. $^1H$ NMR (400 MHz, $CDCl_3$): δ 7.26-7.41 (m, 5H), 5.48-5.82 (m, 214H), 5.20 (s, 2H), 4.05-4.32 (m, 442H), 1.19-1.49 (m, 642H). $^{13}C$ NMR (150 MHz, $CDCl_3$): δ 165.0-167.5, 127.2-128.9, 90.6-94.0, 62.0, 13.8. FT-IR (KBr, thin film): 2982, 1762, 1448, 1379, 1020 $cm^{-1}$. SEC: $M_n$=31 kg/mol, $M_w$=59 kg/mol, PDI=1.9. $T_g$=−3° C.

Polymerization of Ethyl Glyoxylate with NVOC-Cl as End-Cap (Polymer 4)

Poly(ethyl glyoxylate) was prepared as described for polymer 1. Following polymerization, but prior to precipitation, NVOC-Cl (0.2 g, 730 µmol, 0.014 equiv.) was added at 0° C. to end-cap the polymer along with $Et_3N$ (100 µL, 730 µmol, 0.014 equiv.). The solution was stirred for 24 hours at room temperature and a further 16 hours at 40° C. Purification was achieved by precipitation of the crude reaction mixture into methanol. After decanting the excess methanol, the residue was dried in vacuo for 48 hours to provide 3.2 g of a white, sticky polymer in 62% yield. $^1H$ NMR (400 MHz, $CDCl_3$): δ 7.75 (s, 1H), 7.01 (s, 1H), 5.48-5.75 (m, 120H), 4.06-4.34 (m, 265H), 4.05 (s, 3H), 3.97 (s, 3H), 1.17-1.45 (m, 390H). $^{13}C$ NMR (150 MHz, $CDCl_3$): δ 164.8-166.4, 148.1, 107.9, 90.1-94.0, 86.9, 66.7, 61.9, 56.5, 55.1, 13.7. FT-IR (KBr, thin film): 2985, 1757, 1448, 1377, 1022 $cm^{-1}$. SEC: $M_n$=62 kg/mol, $M_w$=132 kg/mol, PDI=2.1. $T_g$=−9° C.

Polymerization of Methyl Glyoxylate with NVOC-Cl as End-Cap (Polymer 11)

Freshly distilled methyl glyoxylate (5.0 mL, 63 mmol, 1.0 equiv.) was dissolved in dichloromethane (5.0 mL) and $Et_3N$ (4.4 µL, 32 µmol, 0.0005 equiv.). After the solution had been stirred for one hour at −20° C., $Et_3N$ (0.2 mL, 1.5 mmol, 0.023 equiv.) and NVOC-Cl (0.4 g, 1.5 mmol, 0.023 equiv.) were added into the mixture to end-cap the polymer. The solution was then stirred for 24 hours at room temperature and a further 16 hours at 40° C. Purification was achieved by precipitation of the crude reaction mixture into methanol. After decanting the excess methanol, the residue was dried in vacuo for 48 hours, to provide 3.3 g of a white, semi-crystalline polymer in 59% yield. $^1H$ NMR (400 MHz, $CDCl_3$): δ 7.75 (s, 1H), 7.14 (s, 1H), 5.55-5.78 (m, 37H), 4.06 (s, 3H), 3.97 (s, 3H), 3.73-3.86 (m, 111H). $^{13}C$ NMR (150 MHz, $CDCl_3$): δ 164.7-166.5, 153.8, 148.1, 109.2, 107.6, 90.0-93.9, 86.7, 66.8, 56.4, 56.2, 52.6. FT-IR (KBr, thin film): 2960, 1760, 1440, 1019 $cm^{-1}$. SEC: $M_n$=3800 g/mol, $M_w$=4800 g/mol, PDI=1.3. $T_g$=24° C.

Polymerization of n-Butyl Glyoxylate with NVOC-Cl as End-Cap (Polymer 12)

Freshly distilled n-butyl glyoxylate (5.0 mL, 38 mmol, 1.0 equiv.) was dissolved in dichloromethane (5.0 mL) and $Et_3N$ (2.7 µL, 19 µmol, 0.0005 equiv.). After the solution was stirred for one hour at −10° C., $Et_3N$ (0.2 mL, 1.5 mmol, 0.038 equiv.) and NVOC-Cl (0.4 g, 1.5 mmol, 0.038 equiv.) were added into the mixture to end-cap the polymer. The solution was then stirred for 24 hours at room temperature and a further 16 hours at 40° C. The solvent was removed by high vacuum and the crude polymer was re-dissolved in tetrahydrofuran (5.0 mL) and dialyzed against water for 24 hours (200 mL, 2 solvent changes) using a regenerated cellulose membrane (6000-8000 g/mol MWCO). The residual content was then lyophilized to afford 2.2 g of a pale yellow, gel-like polymer in 44% yield. $^1H$ NMR (400 MHz, $CDCl_3$): δ 7.75 (s, 1H), 7.09 (s, 1H), 5.46-5.77 (m, 23H), 4.06-4.24 (m, 44H), 4.05 (s, 3H), 3.96 (s, 3H), 1.55-1.73 (m, 44H), 1.25-1.45 (m, 43H), 0.81-1.04 (m, 62H). $^{13}C$ NMR (150 MHz, $CDCl_3$): δ 164.1-166.4, 153.9, 147.5, 109.2, 107.6, 90.2-94.3, 65.7, 56.6, 56.3, 30.2, 18.8, 13.6. FT-IR (KBr, thin film): 2963, 2936, 2876, 1759, 1464, 1379, 1219, 1016 $cm^{-1}$. SEC: $M_n$=5000 g/mol, $M_w$=9800 g/mol, PDI=1.9. $T_g$=−30° C.

Polymerization of Benzyl Glyoxylate with NVOC-Cl as End-Cap (Polymer 13)

Freshly distilled benzyl glyoxylate (5.0 mL, 36 mmol, 1.0 equiv.) was dissolved in dichloromethane (5.0 mL) and $Et_3N$ (2.5 µL, 18 µmol, 0.0005 equiv.). After the solution was stirred for one hour at 0° C., $Et_3N$ (0.2 mL, 1.5 mmol, 0.042 equiv.) and NVOC-Cl (0.40 g, 1.5 mmol, 0.042 equiv.) were added into the mixture to end-cap the polymer. The solution was then stirred for 24 hours at room temperature and a further 16 hours at 40° C. The solvent was removed under high vacuum and the crude polymer was re-dissolved in DMF (5.0 mL) and dialyzed against DMF for 24 hours (200 mL, 2 solvent changes) and water for 24 hours (200 mL, 2 solvent changes) using a regenerated cellulose membrane (6000-8000 g/mol MWCO). The residual content was then lyophilized to afford 1.9 g of a pale yellow, solid, polymer in 36% yield. $^1H$ NMR (400 MHz, $CDCl_3$): δ 7.69 (s, 1H), 6.89-7.36 (m, 88H), 5.46-5.83 (m, 23H), 4.74-5.20 (m, 41H), 3.93 (s, 3H), 3.73 (s, 3H). $^{13}$C NMR (150 MHz, CDCl$_3$): δ 164.6-166.6, 153.9, 147.4, 134.8, 128.2, 109.1, 107.7, 91.1-94.2, 67.4, 56.5, 56.3. FT-IR (KBr, thin film): 3034, 2968, 1763, 1583, 1522, 1500, 1456, 1217, 974, 746, 696 cm$^{-1}$. SEC: M$_n$=2100 g/mol, M$_w$=3500 g/mol, PDI=1.6. T$_g$=12° C.

Copolymerization of Ethyl Glyoxylate and Methyl Glyoxylate with NVOC-Cl as End-Cap (Polymer 14)

Freshly distilled methyl glyoxylate (4.0 mL, 50 mmol, 1.0 equiv.) and ethyl glyoxylate (4.0 mL, 40 mmol, 0.8 equiv.) were dissolved in dichloromethane (8.0 mL) and Et$_3$N (12.6 μL, 90 μmol, 0.001 equiv.). After the solution was stirred for one hour at −20° C., Et$_3$N (0.2 mL, 1.5 mmol, 0.03 equiv.) and NVOC-Cl (0.4 g, 1.5 mmol, 0.03 equiv.) were added into the mixture to end-cap the polymer. The solution was then stirred for 24 hours at room temperature and a further 16 hours at 40° C. Purification was achieved by precipitation of the crude reaction mixture into methanol. After decanting the excess methanol, the residue was dried in vacuo for 48 hours to provide 4.8 g of a white, rubbery polymer in 57% yield. $^1$H NMR (400 MHz, CDCl$_3$): δ 7.75 (s, 1H), 7.09 (s, 1H), 5.48-5.78 (m, 70H), 4.16-4.32 (m, 70H), 4.05 (s, 3H), 3.97 (s, 3H), 3.73-3.86 (m, 87H), 1.21-1.39 (m, 104H). $^{13}$C NMR (150 MHz, CDCl$_3$): δ 164.6-166.8, 148.1, 107.9, 90.1-94.4, 66.8, 61.9, 56.2, 52.5, 13.6. FT-IR (KBr, thin film): 2960, 1759, 1445, 1377, 1016 cm$^{-1}$. SEC: M$_n$=40 kg/mol, M$_w$=81 kg/mol, PDI=2.0. T$_g$=15° C.

Copolymerization of Ethyl Glyoxylate and n-Butyl Glyoxylate with NVOC-Cl as End-Cap (Polymer 15)

Freshly distilled n-butyl glyoxylate (3.0 mL, 25 mmol, 1.0 equiv.) and ethyl glyoxylate (4.0 mL, 40 mmol, 1.6 equiv.) were dissolved in dichloromethane (7.0 mL) and Et$_3$N (9.0 μL, 65 μmol, 0.001 equiv.). After the solution was stirred for one hour at −10° C., Et$_3$N (0.2 mL, 1.5 mmol, 0.023 equiv.) and NVOC-Cl (0.40 g, 1.5 mmol, 0.023 equiv.) were added into the mixture to end-cap the polymer. The solution was then stirred for 24 hours at room temperature and a further 16 hours at 40° C. After that the solvent was removed by high vacuum and the crude polymer was re-dissolved into DMF (5.0 mL) and dialyzed against DMF for 24 hours (200 mL, 2 solvent changes) and distilled water for 24 hours (200 mL, 2 solvent changes) using a regenerated cellulose membrane (6000-8000 g/mol MWCO). The residual content was then lyophilized to afford 3.4 g of a clear, colorless, gel-like polymer in 45% yield. $^1$H NMR (400 MHz, CDCl$_3$): δ 7.75 (s, 1H), 7.16 (s, 1H), 5.46-5.75 (m, 60H), 4.09-4.43 (m, 124H), 4.05 (s, 3H), 3.97 (s, 3H), 1.57-1.73 (m, 40H), 1.17-1.46 (m, 164H), 0.84-0.99 (m, 53H). $^{13}$C NMR (150 MHz, CDCl$_3$): δ 164.7-166.7, 153.7, 148.2, 141.4, 126.7, 109.9, 107.9, 90.4-94.5, 66.8, 65.7, 61.9, 56.7, 56.3, 30.2, 18.8, 13.8, 13.6. FT-IR (KBr, thin film): 2964, 2939, 2876, 1765, 1468, 1381, 1219, 1024 cm$^{-1}$. SEC: M$_n$=11 kg/mol, M$_w$=22 kg/mol, PDI=2.0. T$_g$=−10° C.

Polymerization of Ethyl Glyoxylate with Compound 18 as End-Cap (Polymer 19)

Poly(ethyl glyoxylate) was prepared as described for polymer 1. Following polymerization, but prior to precipitation, compound 18 (0.22 g, 730 μmol, 0.014 equiv.) was added at 0° C. to end-cap the polymer along with Et$_3$N (100 μL, 730 μmol, 0.014 equiv.). The solution was stirred for 24 hours at room temperature and a further 16 hours at 40° C. Purification was achieved by precipitation of the crude reaction mixture into methanol. After decanting the excess methanol, the residue was dried in vacuo for 48 hours to provide 2.8 g of a white, sticky polymer in 56% yield. $^1$H NMR (400 MHz, CDCl$_3$): δ 8.65 (s, 1H), 8.19 (s, 1H), 7.82 (s, 1H), 5.46-5.71 (m, 275H), 4.12-4.30 (m, 570H), 2.29 (s, 1H), 1.12-1.40 (m, 855H). $^{13}$C NMR (150 MHz, CDCl$_3$): δ 169.4, 164.9-166.7, 128.3, 90.9-94.5, 81.7, 62.9, 62.2, 29.9, 13.9. FT-IR (KBr, thin film): 2988, 1759, 1468, 1379, 1021, 1028 cm$^{-1}$. SEC: M$_n$=42 kg/mol, M$_w$=89 kg/mol, PDI=2.1.

Coupling of Polymer 19 with Polymer 20 (Polymer 21)

Synthesis of Polymer 21a.

PEG-N$_3$ (polymer 20a) (750 Da, 56 mg, 75 μmol, 1.5 equiv.) and polymer 19 (59 kDa, 1.0 g, 25 μmol, 1 equiv.) were dissolved into DMF (5 mL). After removing the air and refilling with argon, CuSO$_4$ (4 mg, 25 μmol, 1 equiv.) and sodium ascorbate (5 mg, 25 μmol, 1 equiv.) were added into the solution, and the mixture was stirred at 40° C. for 16 hours. It was then transferred into a regenerated cellulose membrane (50 kDa MWCO) and dialyzed against deionized water for 48 hours (300 mL, 6 solvent changes). The dialyzed material was then lyophilized to afford polymer 3.1 (860 mg, 81%). 1H NMR (400 MHz, CDCl$_3$): δ 5.47-5.75 (m, 473H), 4.15-4.31 (m, 854H), 3.65 (s, 136H), 3.39 (s, 6H), 1.17-1.40 (m, 1269H). SEC: Mn=68 kDa, Mw=130 kDa, Đ=1.9.

Synthesis of Polymer 21b.

PEG-N$_3$ (polymer 20b) (2 KDa, 150 mg, 75 μmol, 3 equiv.) and polymer 19 (500 mg, 25 μmol, 1 equiv.) were dissolved into DMF (5 mL). After removing the air and refilling with argon, CuSO$_4$ (4 mg, 25 μmol, 1 equiv.) and sodium ascorbate (5 mg, 25 μmol, 1 equiv.) were added into the solution, and the mixture was stirred at 40° C. for 16 hours. Then it was transferred into a regenerated cellulose membrane (50 kg/mol MWCO) and dialyzed against deionized water for 48 hours (300 mL, 6 solvent changes). The dialyzed material was then lyophilized to afford 434 mg of a white, rubber-like, polymer in 79% yield. $^1$H NMR (400 MHz, CDCl$_3$): δ 8.71 (s, 1H), 8.24 (s, 1H), 7.83 (s, 1H) 5.47-5.75 (m, 100H), 4.15-4.31 (m, 211H), 3.65 (s, 92H), 3.39 (s, 3H), 1.17-1.40 (m, 307H). $^{13}$C NMR (150 MHz, CDCl$_3$): δ 164.7-166.3, 127.5, 124.1, 90.8-93.9, 71.8, 70.5, 62.0, 13.7. FT-IR (KBr, thin film): 2985, 2941, 2908, 2876, 1759, 1447, 1377, 1231, 1021 cm$^{-1}$. SEC: M$_n$=40 kg/mol, M$_w$=85 kg/mol, PDI=2.1. T$_g$=−5° C.

Synthesis of Polymer 21c.

PEG-N$_3$ (polymer 20c) (5 kDa, 375 mg, 75 μmol, 1.5 equiv.) and polymer 19 (47 kDa, 0.5 g, 25 μmol, 1 equiv.) were dissolved in DMF (5 mL). After removing the air and refilling with argon, CuSO4 (4 mg, 25 μmol, 1 equiv.) and sodium ascorbate (5 mg, 25 μmol, 1 equiv.) were added into the solution, and the mixture was stirred at 40° C. for 16 hours. It was then transferred into a regenerated cellulose membrane (50 kDa MWCO) and dialyzed against deionized water for 48 hours (300 mL, 6 solvent changes). The dialyzed material was then lyophilized to afford polymer 3.3 (580 mg, 77%). 1H NMR (400 MHz, CDCl3): δ 5.47-5.75 (m, 578H), 4.15-4.31 (m, 1023H), 3.65 (s, 909H), 3.39 (s, 6H), 1.17-1.40 (m, 1502H). SEC: Mn=50 kDa, Mw=95 kDa, Đ=1.9.

Coupling of Polymer 19 with Compound 22 (Polymer 23)

Polymer 19 (1.0 g, 25 μmol, 1 equiv.) and compound 22 (37.5 mg, 150 μmol, 6 equiv.) were dissolved into DMF (7 mL). After removing the air and refilling with argon, CuSO$_4$ (4 mg, 25 μmol, 1 equiv.) and sodium ascorbate (5 mg, 25 μmol, 1 equiv.) were added into the solution, and the mixture was stirred at 40° C. for 16 hours. Then it was transferred into a regenerated cellulose membrane (50 kDa MWCO) and dialyzed against the mixture of acetone and methanol (3:7) for 48 hours (1000 mL, 6 solvent changes). The dialyzed material was then dried to afford 856 mg of macroinitiator (polymer 23). $^1$H NMR (400 MHz, CDCl$_3$):

δ 5.49-5.73 (m, 96H), 4.13-4.30 (m, 199H), 1.95 (s, 0.73H), 1.17-1.40 (m, 300H). SEC: $M_n$=83 kg/mol, $M_w$=147 kg/mol, PDI=1.8.

Atom-Transfer Radial Polymerization Using Macroinitiator 23 (Polymer 24)

Polymer 23 (0.7 g, 17 μmol, 1 equiv.), 2-(dimethylamino)ethyl methacrylate (1.1 g, 6.8 mmol, 400 equiv.) and N,N,N',N",N"-pentamethyldiethylenetriamine (5.8 mg, 34 μmol, 2 equiv.) were dissolved in DMF (7 mL). After removing the air and refilling with argon, $CuSO_4$ (3.7 mg, 17 μmol, 1 equiv.) and sodium ascorbate (15 mg, 85 μmol, 5 equiv.) were added into the solution, and the mixture was stirred at 40° C. for 16 hours. Then it was transferred into a regenerated cellulose membrane (50 kg/mol MWCO) and dialyzed against the mixture of acetone and methanol (3:7) for 24 hours (500 mL, 3 solvent changes). The dialyzed material was then dried to afford 340 mg block polymer. $^1$H NMR (400 MHz, CDCl$_3$): δ 5.48-5.72 (m, 100H), 4.17-4.31 (m, 215H), 4.01-4.15 (m, 111H), 2.51-2.78 (m, 101H), 2.19-2.48 (m, 347H), 1.75-2.03 (m, 87H), 1.16-1.34 (m, 339H), 0.78-1.11 (m, 172H). SEC: $M_n$=76 kg/mol, $M_w$=136 kg/mol, PDI=1.8.

Co-Polymerization of Propargyl Glyoxylate (28) and Ethyl Glyoxylate with NVOC-Cl as End-Cap Freshly distilled propargyl glyoxylate (1.0 mL, 9 mmol, 1.0 equiv.) and ethyl glyoxylate (5.0 mL, 50 mmol, 5.5 equiv.) were dissolved in dichloromethane (7.0 mL) and Et$_3$N (2.0 μL, 16 μmol, 0.001 equiv.). After the solution was stirred for one hour at −10° C., Et$_3$N (0.2 mL, 1.5 mmol, 0.09 equiv.) and NVOC-Cl (0.40 g, 1.5 mmol, 0.09 equiv.) were added into the mixture to end-cap the polymer. The solution was then stirred for 24 hours at room temperature and a further 16 hours at 40° C. After that the solvent was removed by high vacuum and the crude polymer was re-dissolved into DMF (5.0 mL) and dialyzed against DMF for 24 hours (200 mL, 2 solvent changes) and distilled water for 24 hours (200 mL, 2 solvent changes) using a regenerated cellulose membrane (3 kg/mol MWCO). The residual content was then lyophilized to afford 2.0 g of a clear, colorless, gel-like polymer in 30% yield. $^1$H NMR (400 MHz, CDCl$_3$): δ 7.72 (s, 2H), 7.13 (s, 2H), 5.87-5.40 (m, 76H), 4.90-4.73 (m, 14H), 4.32-4.10 (m, 142H), 4.03 (s, 6H), 3.93 (s, 6H), 2.60-2.45 (m, 6H), 1.32-1.23 (m, 210H). SEC: $M_n$=4.3 kg/mol, $M_w$=5.7 kg/mol, Đ=1.3.

Co-Polymerization of 2-(Tert-Butyldimethylsiloxy)Ethyl Glyoxylate (30) with Ethyl Glyoxylate Freshly distilled 2-(tert-butyldimethylsiloxy)ethyl glyoxylate (1.0 mL, 4.3 mmol, 1.0 equiv.) and ethyl glyoxylate (5 mL, 50 mmol, 11 equiv.) were dissolved in dichloromethane (5 mL) and Et$_3$N (0.8 μL, 5 μmol, 0.001 equiv.). After the solution was stirred for one hour at −10° C., Et$_3$N (0.3 mL, 2.25 mmol, 0.53 equiv.) and NVOC-Cl (0.3 g, 1.2 mmol, 0.28 equiv.) were added into the mixture to end-cap the polymer. The solution was then stirred for 24 hours at room temperature and a further 16 hours at 40° C. After that the solvent was removed by high vacuum and the crude polymer was re-dissolved into DMF (5.0 mL) and dialyzed against DMF for 24 hours (200 mL, 2 solvent changes) and distilled water for 24 hours (200 mL, 2 solvent changes) using a regenerated cellulose membrane (30 kg/mol MWCO). The residual content was then lyophilized to afford 850 mg of a clear off-white, gel-like polymer in 22% yield. $^1$H NMR (400 MHz, CDCl$_3$): δ 7.75 (s, 2H), 7.09 (s, 2H), 5.75-5.44 (m, 184H), 4.30-4.14 (m, 327H), 4.05 (s, 6H), 3.97 (s, 6H), 3.85-3.78 (m, 32H), 1.35-1.23 (m, 448H). 0.92-0.85 (88H, m), 0.09-0.02 (m, 56H). SEC: $M_n$=25 kg/mol, $M_w$=49 kg/mol, Đ=1.9.

Synthesis of Polymer 48

Purified ethyl glyoxylate (5.0 mL, 50 mmol, 1.0 equiv.) was dissolved in CH$_2$Cl$_2$ (5.0 mL) and Et$_3$N (3.5 μL, 25 μmol, 0.0005 equiv.). The solution was stirred for 1 h at −20° C. Chloroformate 45 (0.22 g, 730 μmol, 0.014 equiv.) and Et$_3$N (100 μL, 730 μmol, 0.014 equiv.) were added at 0° C. to end-cap the polymer. The solution was stirred for 24 h at room temperature and a further 16 h at 40° C. Purification was achieved by precipitation of the crude reaction mixture into methanol. After decanting the excess methanol, the residue was dried in vacuo for 48 h to provide 3.3 g of a white, sticky polymer in 63% yield. $^1$H NMR (400 MHz, CDCl$_3$): δ 7.80 (d, J=8.6 Hz, 2H), 7.53 (d, J=8.6 Hz, 2H), 5.46-5.78 (m, 675H), 4.10-4.33 (m, 1367H), 1.34 (s, 12H), 1.21-1.44 (m, 2000H). $^{13}$C NMR (150 MHz, CDCl$_3$): δ 164.6-166.5, 90.0-93.9, 61.7, 13.5. FT-IR (KBr, thin film): 2986, 2943, 2908, 1759, 1469, 1446, 1377, 1302, 858, 735, 702 cm$^{-1}$. SEC: $M_n$=131 kg/mol, $M_w$=304 kg/mol, Đ=2.3. $T_g$=−1° C.

Synthesis of Polymer 49.

Purified ethyl glyoxylate (2.5 mL, 25 mmol, 1.0 equiv.) was dissolved in CH$_2$Cl$_2$ (2.5 mL) and Et$_3$N (1.8 μL, 13 μmol, 0.0005 equiv.). The solution was stirred for 1 h at −20° C. Chloroformate 46 (0.11 g, 365 μmol, 0.014 equiv.) and Et$_3$N (100 μL, 730 μmol, 0.028 equiv.) were added at 0° C. to end-cap the polymer. The solution was stirred for 24 h at room temperature and a further 16 h at 40° C. Purification was achieved by precipitation of the crude reaction mixture into methanol. After decanting the excess methanol, the residue was dried in vacuo for 48 h to provide 1.5 g of a white, sticky polymer in 60% yield. $^1$H NMR (400 MHz, CDCl$_3$): δ 5.48-5.75 (m, 2500H), 4.12-4.33 (m, 5150H), 1.34 (s, 12H), 1.20-1.37 (m, 7645H). $^{13}$C NMR (150 MHz, CDCl$_3$): δ 165.4-166.1, 91.0-94.43, 62.4, 14.2. FT-IR (KBr, thin film): 2986, 2939, 2367, 1765, 1468, 1385, 1302, 1229, 1146, 1020, 966, 8568 cm$^{-1}$. SEC: $M_n$=250 kg/mol, $M_w$=425 kg/mol, Đ=1.7. $T_g$=−7° C.

Synthesis of Polymer 50.

Purified ethyl glyoxylate (2.5 mL, 25 mmol, 1.0 equiv.) was dissolved in CH$_2$Cl$_2$ (2.5 mL) and Et$_3$N (1.8 μL, 13 μmol, 0.0005 equiv.). The solution was stirred for 1 h at −20° C. Chloroformate 47 (0.12 g, 365 μmol, 0.014 equiv.) and Et$_3$N (50 μL, 365 μmol, 0.014 equiv.) were added at 0° C. to end-cap the polymer. The solution was stirred for 24 h at room temperature and a further 16 h at 40° C. Purification was achieved by precipitation of the crude reaction mixture into methanol. After decanting the excess methanol, the residue was dried in vacuo for 48 h to provide 1.2 g of a white, sticky polymer in 48% yield. $^1$H NMR (400 MHz, CDCl$_3$): δ 5.47-5.76 (m, 2548H), 4.09-4.31 (m, 5299H), 1.25-1.42 (m, 7798H). $^{13}$C NMR (150 MHz, CDCl$_3$): δ 165.9-166.7, 91.2-94.3, 62.1, 13.8. FT-IR (KBr, thin film): 2986, 2947, 1767, 1468, 1379, 1300, 1229, 1144, 1026, 964, 858 cm$^{-1}$. SEC: $M_n$=246 kg/mol, $M_w$=461 kg/mol, Đ=1.9. $T_g$=−7° C.

Polymerization of Ethyl Glyoxylate with Compound 53 as End-Cap (Polymer 54)

Poly(ethyl glyoxylate) was prepared as described for polymer 1. Following polymerization, but prior to precipitation, compound 53 (0.38 g, 730 μmol, 0.014 equiv.) was added at 0° C. to end-cap the polymer along with Et$_3$N (100 μL, 730 μmol, 0.014 equiv.). The solution was stirred for 24 hours at room temperature and a further 16 hours at 40° C. After that the solvent was removed by high vacuum and the crude polymer was re-dissolved into acetone (5.0 mL) and dialyzed against mixed solvent (1:1=methano:acetone) for 24 hours (500 mL, 3 solvent changes) using a regenerated cellulose membrane (6000-8000 g/mol MWCO). The solvent was removed by high vacuum to afford 1.2 g of a clear, colorless polymer in 24% yield. $^1$H NMR (400 MHz, CDCl$_3$): δ 7.85 (m, 4H), 7.63 (m, 2H), 7.40 (m, 6H), 6.26 (m, 2H), 5.47-5.75 (m, 53H), 5.21 (s, 4H), 4.09-4.43 (m, 101H), 2.27 (s, 2H), 1.33 (s, 24), 1.17-1.46 (m, 142H). SEC: Mn=9.4 kDa, Mw=17 kDa, Đ=1.8.

Synthesis of Copolymer 55

PEG-N$_3$ (polymer 20b) (2 kDa, 180 mg, 90 μmol, 3 equiv.) and polymer 54 (10 kDa, 0.3 g, 30 μmol, 1 equiv.) were dissolved in DMF (5 mL). After removing the air and refilling with argon, CuSO4 (4.5 mg, 30 μmol, 1 equiv.) and sodium ascorbate (5.5 mg, 30 μmol, 1 equiv.) were added into the solution, and the mixture was stirred at 40° C. for 16 hours. It was then transferred into a regenerated cellulose membrane (50 kDa MWCO) and dialyzed against deionized water for 48 hours (300 mL, 6 solvent changes). The dialyzed material was then lyophilized to afford polymer 51 (120 mg, 33%). $^1$H NMR (400 MHz, CDCl3): δ 5.47-5.75 (m, 90H), 4.15-4.31 (m, 185H), 3.65 (s, 441H), 1.17-1.40 (m, 273H). SEC: Mn=9.8 kDa, Mw=13 kDa, Đ=1.3.

Degradation Studies

NMR Degradation Study of Polymers in Solution

General Protocol for Degradation Studies Involving UV Light as a Stimulus

Polymer 4 (15.0 mg) was dissolved into a mixture of CD$_3$CN and deuterium oxide (1.2 mL, 9:1, v/v). The solution was then transferred into two NMR tubes and the tubes were promptly sealed. One tube was exposed to UV light (wavelength: 300-350 nm, 1400 LUX) to initiate the removal of the photo-labile end-cap, and the absorbance at 341 nm was monitored by UV-vis spectroscopy to ensure the complete deprotection of the polymer (approximately 80 minutes). Another NMR tube was stored in a light-impermeable box over this time, and was prepared as a control for any background polymer degradation. Then, $^1$H NMR spectra were recorded at defined intervals to monitor the depolymerization of the materials. At the same time, polymer 3 also went through all of these procedures to work as a non-triggerable control.

This same protocol was also applied to study the degradation of polymers 11-15 and 21.

General Protocol for Degradation Studies Involving H$_2$O$_2$ as a Stimulus

PEtG 48 (15 mg) was dissolved in a 9:1 mixture of CD$_3$CN:D$_2$O (1.2 mL) at ambient temperature (21° C.). The solution was then transferred into two NMR tubes and 4 μL H$_2$O$_2$ (50 wt % in water solution) was added to one tube to initiate the removal of the H$_2$O$_2$-labile end-cap, then the tubes were promptly sealed. $^1$H NMR spectra were recorded at defined intervals to monitor the depolymerization of the materials. At the same time, benzyl chloroformate end-capped PEtG 3 was also exposed to the same amount of H$_2$O$_2$ and its depolymerization was monitored by NMR spectroscopy.

General Protocol for Degradation Studies Involving DTT as a Stimulus

PEtG 49 or 50 (15 mg) was dissolved in a 9:1 mixture of CD$_3$CN:D$_2$O (1.2 mL) at ambient temperature (21° C.). The solution was then transferred into two NMR tubes and 10 mg DTT was added to one tube to initiate the removal of the end-cap, then the tubes were promptly sealed. $^1$H NMR spectra were recorded at defined intervals to monitor the depolymerization of the materials. At the same time, benzyl chloroformate end-capped PEtG 3 was also exposed to the same amount of DTT and its depolymerization was monitored by NMR spectroscopy.

General Protocol for Mass Loss and SEC Degradation Studies

Polymer 4 (3.0 g) was dissolved in dichloromethane (15 mL) and drop-cast onto sixty individual glass slides to provide sixty thin films. After the solvent was evaporated in vacuo for 48 hours in a desiccator, the mass of each film sample was recorded. 30 films were placed into a UV box as describe above for 17 hours to remove the end-cap. During this time the remaining slides were stored in the dark. Then, all the slides were placed into a buffer solution (phosphate buffer, 100 mM, pH=7.4) at ambient temperature (21° C.). At selected times, three plates from each treatment were removed from the buffer solution, rinsed, and dried under house vacuum for 48 hours and then weighed. Any weight loss during those procedures was attributed to the degradation of polymer. A control group, made up of polymer 3, was also subjected to identical treatment to control for background polymer degradation. After each set of samples was weighed, 5.0 mg from a slide of each treatment was analyzed by SEC to assess any polymer degradation via molecular weight changes that did not result in mass-loss. The mass loss studies were also performed under different conditions including: pH 5.0 (100 mM citrate buffer), 20° C.; pH 6.0 (100 mM citrate buffer), 20° C.; pH 7.0 (100 mM phosphate buffer), 20° C., pH 8.0 (100 mM phosphate buffer), 20° C.; pH 7.0 (100 mM phosphate buffer), 10° C.; pH 7.0 (100 mM phosphate buffer), 30° C.

Dynamic Light Scattering (DLS)

The sizes and size distributions of the nanoparticles prepared as described above were measured by dynamic light scattering (Zetasizer Nano Series, Malvern Instruments, UK) at room temperature (25° C.) in a glass cell. The concentration of polymer was approximately 1 mg/mL.

Representative Micelle Preparation 8 mg of polymer 21b (PEG-PEtG-PEG(2 k)) was fully dissolved in 1 mL of DMSO. Then, 0.1 mL of the resulting solution was injected quickly into 0.9 mL of stirring deionized water. After stirring for 0.5 hours, the micelle suspension was transferred into a regenerated cellulose membrane (3 kDa MWCO) and dialyzed against deionized water for 12 hours (300 mL, 2 solvent changes) to remove DMSO.

Representative Vesicle Preparation 8 mg of polymer 21a (PEG-PEtG-PEG(750)) was fully dissolved in 1 mL of THF. Then, 0.9 mL deionized water was injected dropwise into 0.1 mL of the above stirring solution. After stirring for 0.5 hours, the suspension was transferred into a regenerated cellulose membrane (3 kDa MWCO) and dialyzed against deionized water for 12 hours (300 mL, 2 solvent changes) to remove THF.

Representative DLS Study of Micelle Degradation

The micelles were formed by the procedure described above, except that the DMSO solutions were precipitated into either 100 mM pH 7.4 phosphate buffer solution or 100 Mm pH 5.0 citrate buffer solution and dialyzed against the same buffer. The formed micelles were then transferred into quartz cuvettes and the count rate was measured by DLS while fixing the attenuator at 7. The samples were then irradiated for 20 min in the UV box (wavelength: 300-350 nm, 23 mW cm$^{-2}$), the samples were incubated at 37° C. and the count rate was measured at selected time points.

NMR Degradation Study of the Micelles 16 mg of block copolymer 21 b was fully dissolved in 0.8 mL of DMSO-d$_6$. 0.2 mL of the resulting solution was rapidly injected into 1.0 mL of 100 mM, pH 7.4 phosphate or 100 mM, pH 5.0 citrate buffered D$_2$O. After stirring for 0.5 h, the micelle suspension was transferred into two NMR tubes. One tube was then irradiated for 10 min in with UV light (wavelength: 300-350 nm, 23 mW cm$^{-2}$), while the other one was kept in the dark. A $^1$H NMR spectrum was obtained immediately following irradiation (10 min time point in the graph), then the samples were incubated at 37° C. and spectra were obtained at regular intervals over 24 h. Complete depolymerization was confirmed for the irradiated sample as the sum of the integration of the methyl peaks corresponding to EtGH and ethanol (1.0-1.2 ppm) plateaud at a very similar (1198) value to that of the methyl peak at 1.17-1.45 ppm in the block copolymer 21b taken in CDCl$_3$ (integration 1152) when setting the PEG peak integral to 364. The % polymer remaining was calculated as 100−(sum of integration from 1.0-1.2 ppm/1198))*100.

Representative Procedure Nile Red Encapsulation and Triggered Release 8 mg of block copolymer 21b and 0.16 mg (2 wt % relative to polymer) of nile red were fully dissolved into 1 mL of DMSO to form a homogenous solution. Then, 0.1 mL of the resulting solution was injected quickly into 0.9 mL of stirring deionized water or different buffer solutions. After stirring for 2 minutes, the micelle suspension was then transferred into a regenerated cellulose membrane (3500 g/mol MWCO) and dialyzed against deionized water or different buffer solutions for 12 hours (300 mL, 2 solvent changes) to remove DMSO. After the initial fluorescence emission of the micelle suspension was measured, the micelle suspension was put into a UV box and irradiated for different times (wavelength: 300-350 nm, 23 mW cm$^{-2}$). The fluorescence emission at 605 nm was measured after the different irradiation times.

Dox Encapsulation and Release 10 mg DOX (0.0172 mmol) and 1.74 mg (0.0172) triethylamine were dissolved into 2 mL DMSO and stirred for 10 minutes, then 16 mg polymer 21 b was added into the solution and stirred for 5 hours. The mixed solution was then injected quickly into 18 mL of stirring deionized water and stirred for an additional 15 minutes. The resulting suspension was dialysized against 100 mM pH 5.0 citrate buffer solution for 48 hours (4×1000 mL) with regenerated cellulose membrane (3500 g/mol MWCO). After the initial absorption was measured at 500 nm by UV-visible spectroscopy, the nanomedicine with DOX encapsulated was then separated into two batches, One was irradiated for 3 hours with UV light (wavelength: 300-350 nm, 23 mW cm$^{-2}$), while the other one was kept in the dark. The two samples were then transferred into a regenerated cellulose membrane (3500 g/mol MWCO) and dialysized against 100 mM pH 5.0 citrate buffer solution at 37° C. The absorption of the samples inside the dialysis membrane were measured at selected times over 100 h to quantify the percentage of released drug.

Transmission Electron Microscopy (TEM)

TEM imaging was performed using a Phillips CM10 microscope operating at an acceleration voltage of 80 kV. In order to observe the size and distribution of nanoparticles, 5 μL of nanoparticle suspension (prepared as described above, then diluted to 0.08 mg/mL) was placed onto a copper grid. The resulting sample was air dried for overnight before imaging.

Results and Discussion

Purification and polymerization of commercially available ethyl glyoxylate was examined. Purification of this monomer is an essential prerequisite to obtain high molecular weight PEtG, as transfer reactions initiated by any glyoxylate hydrate, water or other impurities may lead to excessive initiation sites or may terminate the polymerization early. Ultra-pure ethyl glyoxylate was obtained through two successive distillations of the crude monomer at 130° C. over P$_2$O$_5$ under argon at atmospheric pressure. Commonly reported vacuum distillation,[9,12] was found to provide material of insufficient purity. The high temperature of the distillation ensured cracking of the glyoxylate oligomers and the drying agent removed any liberated water. As shown in Scheme 1, PEtG was then synthesized through anionic polymerization to provide polymer 1, and polymers with different end-caps (phenyl isocyanate, benzyl chloroformate and NVOC-Cl) were obtained by in situ treatment with the appropriate reagents. Polymer 2 with the phenyl carbamate end-cap was prepared for comparison with previous work.[14] Polymer 3 was prepared as a model polymer with a carbonate end-cap. Polymer 4 with the NVOC end-cap was chosen as the NVOC group can be cleaved with UV light (λ=341 nm), which was expected to initiate the depolymerization of the polymer (Scheme 2).

Scheme 1
Polymerization and end-capping of PEtG

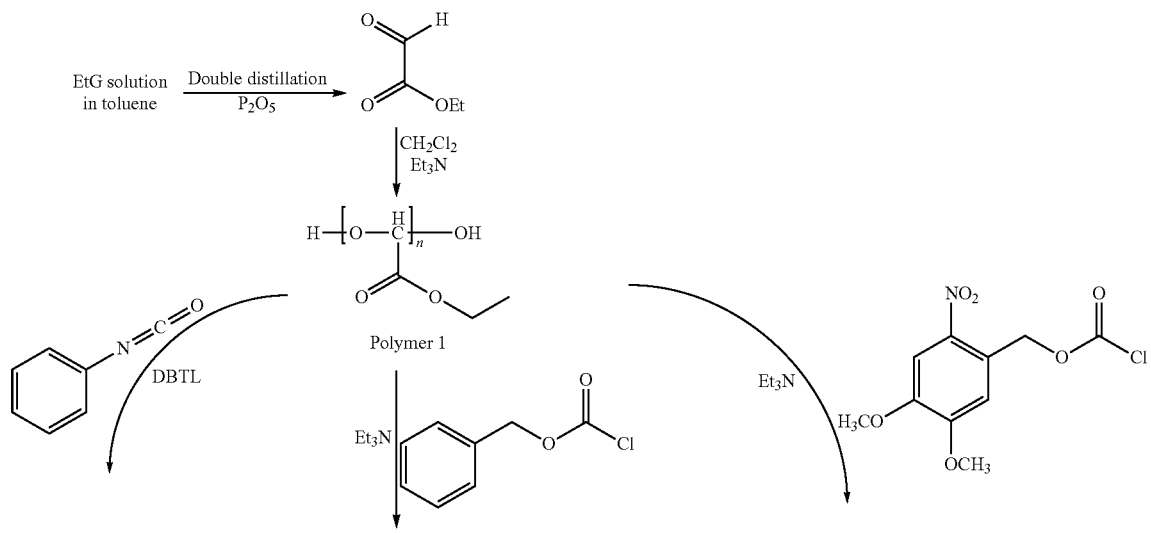

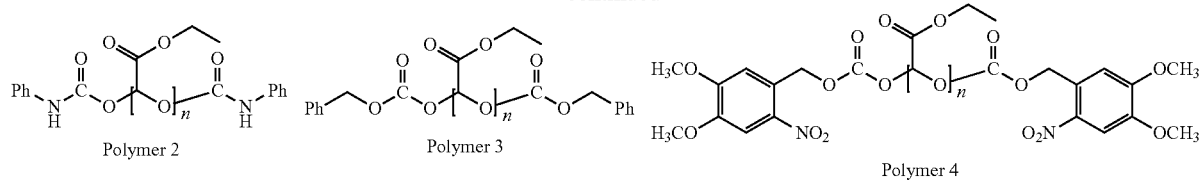

Polymer 2   Polymer 3   Polymer 4

Scheme 2
Degradation mechanism of NVOC—Cl end-capped polyglyoxylates. R = CH$_2$CH$_3$ for PEtG

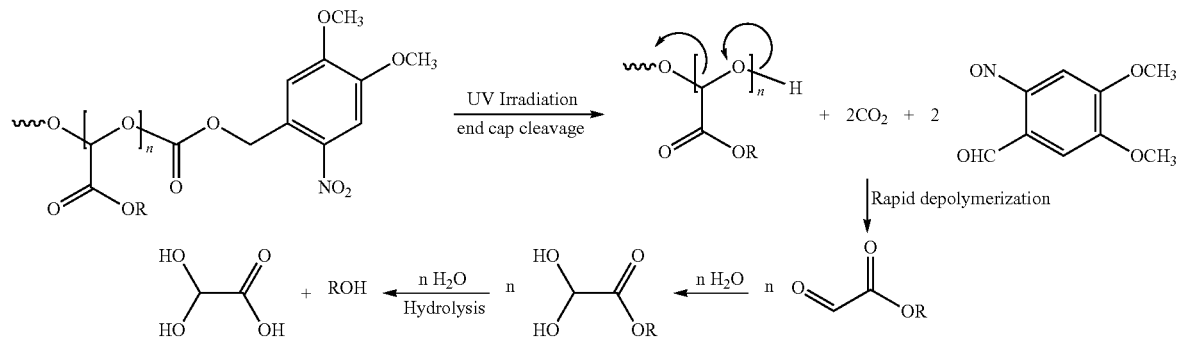

While these PEtGs show interesting properties and polymer 4 provides triggerable decomposition (described below), the simple structure of the monomer should allow for the rapid generation of structural diversity through the preparation of alternate glyoxylates. Several glyoxylates are commercially available, but with the exception of the ethyl derivative, they are all currently prohibitively expensive to obtain on large (greater than 10 mmol) scale. The most common synthetic approach towards glyoxylates is the oxidative cleavage of dialkyl tartrates.[36] This is synthetically simple, but appears to introduce oxidative impurities into the products that could potentially be difficult to remove from such a reactive molecule as a glyoxylate. The purity of these products is sufficient for most synthetic applications, but for polymerization even small concentrations of impurities can result in significant decreases in chain length and yield. Consequently, we sought an alternative methodology for accessing these molecules in significant, 10-100 mmol quantities. Ozonolysis of dialkyl fumarates or maleates is a promising possibility as the starting materials can be easily obtained through standard esterification techniques from very inexpensive feedstocks, and this process has been used industrially for the preparation of a hemiacetal derivative of methyl glyoxylate.[6] The ozonolysis reaction itself is rapid, very clean, and leads to complete conversion. Using dimethyl sulfide as the reductant creates only innocuous dimethyl sulfoxide as a byproduct of the reaction. Isolation of the glyoxylates can be accomplished by simple distillations to remove solvent and reagents as well as to crack any dimers and oligomers that can readily form in the presence of water, to provide the glyoxylates in very high purity.

As shown in Scheme 3, methyl maleate (5), n-butyl fumarate (6) and benzyl fumarate (7) were first prepared and were converted to their corresponding glyoxylates (8-10), as well as their polymers (11-13) and copolymers (with ethyl glyoxylate) (14-15). These polymers were all end-capped with the photolabile NVOC-Cl end-cap to provide materials with a variety of physical characteristics, from tacky adhesives (poly(n-butyl glyoxylate) 12) to glassy solids (poly (methyl glyoxylate) 11).

Scheme 3
Synthesis of different polyglyoxylates.

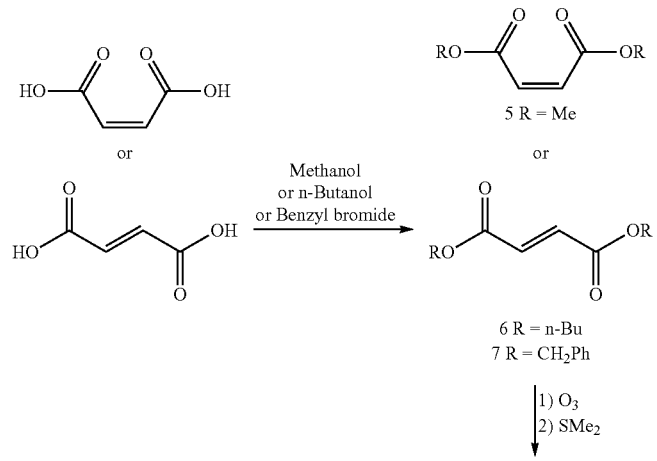

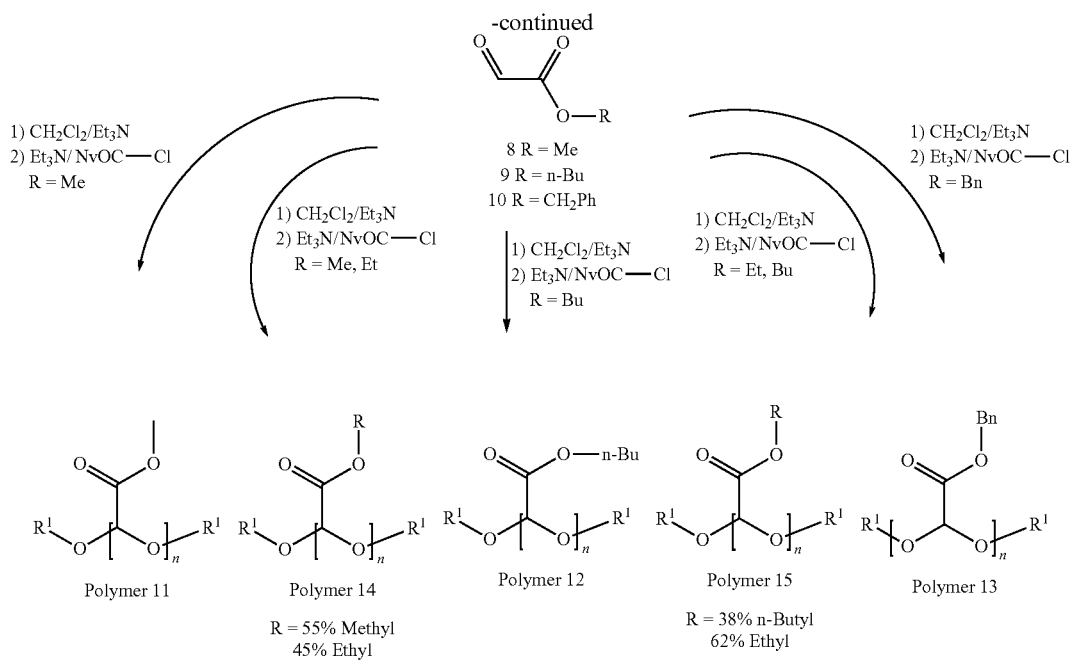

The preparation of block polymers is another strategy routinely used to modify the properties of polymeric materials. Polyglyoxylates are relatively hydrophobic materials, and in order to assemble them into functional nanoparticles, such as micelles and vesicles, for e.g., pharmaceutical applications, the incorporation of a hydrophilic block is required. To demonstrate the feasibility of preparing block copolymers of polyglyoxylates, poly(ethylene glycol) (PEG) was selected as a hydrophilic block. First, an end-cap/linker containing a photodegradable moiety was prepared to link the PEtG and PEG blocks in a way that allows for triggered degradation. As shown in Scheme 4, starting from the previously reported alcohol 16[32], the propargyl amide (compound 17) was synthesized through EDC coupling. The alcohol group was then converted into a chloroformate by phosgene to obtain the target linker (compound 18).

Scheme 4
Preparation of a photodegradable end-cap/linker

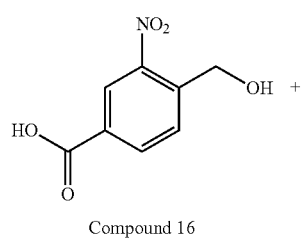

Compound 16

As shown in Scheme 5, PEtG was end-capped with chloroformate 18 to provide photodegradable polymer 19. A copper assisted azide-alkyne cycloaddition (CuAAC) between 19 and azide-terminated PEG having molecular weights of 750, 2000, or 5000 g/mol (20a-c respectively)[37] provided PEG-PEtG-PEG triblock copolymers 21a-c respectively.

Scheme 5
Synthesis of a triblock copolymer. (a corresponds to PEG 750 g/mol; b corresponds to PEG 2000 g/mol; c corresponds to PEG 5000 g/mol)

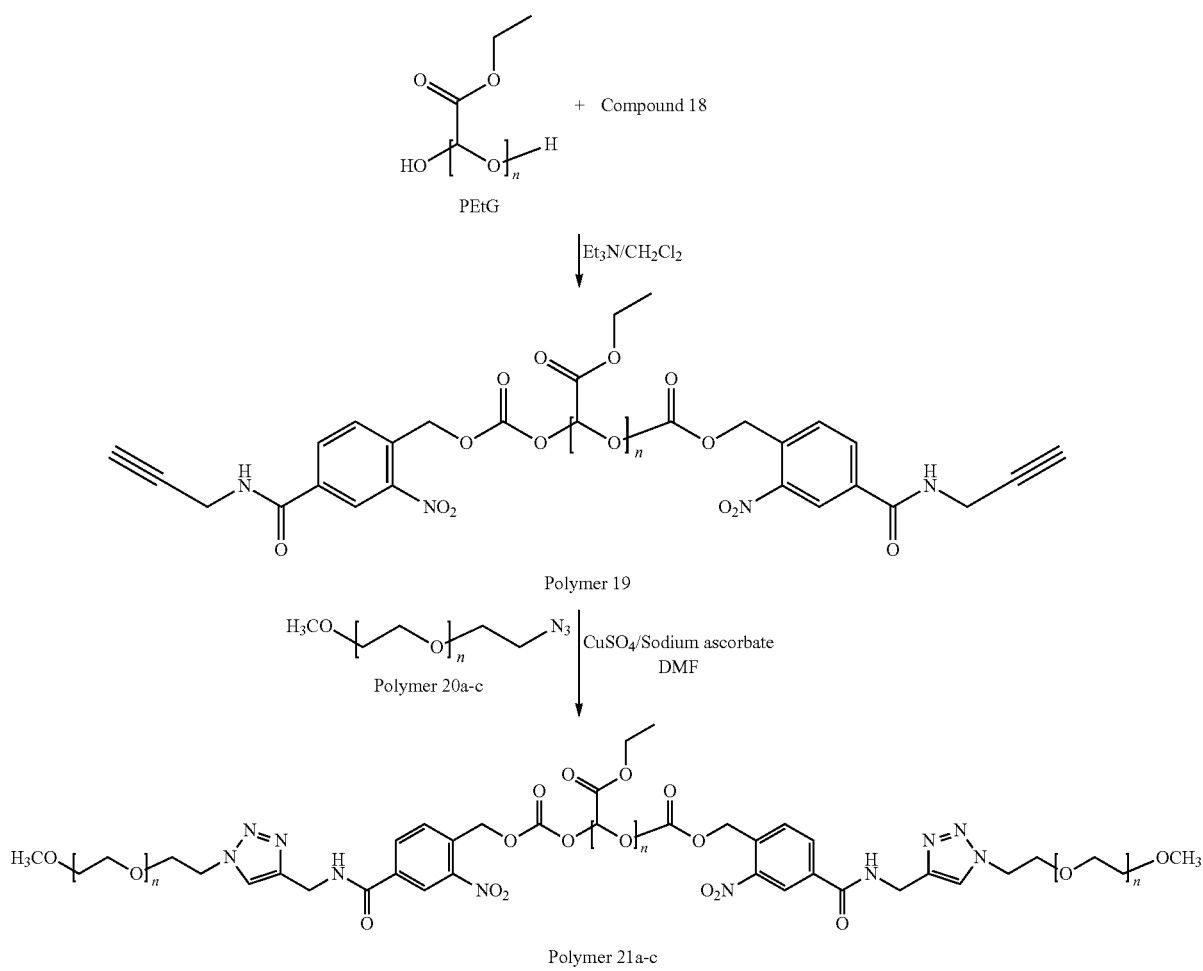

Characterization of Polyglyoxylates

Polyglyoxylates were characterized by $^1H$ and $^{13}C$ nuclear magnetic resonance (NMR) spectroscopy, infrared (IR) spectroscopy, and size exclusion chromatography (SEC). The spectral data were consistent with the expected chemical structures of the materials. As shown in Table 1, SEC results suggested that PEtGs 1-4, with or without the various end-caps, had the highest molecular weights. Poly(methyl glyoxylate) 11, poly(n-butyl glyoxylate) 12, and poly(benzyl glyoxylate) 13 had significantly lower number average molecular weights ($M_n$) and weight average molecular weights ($M_w$). This can possibly be attributed to steric hindrance in the case of n-butyl glyoxylate and benzyl glyoxylate monomers, but the similar result for the methyl glyoxylate suggests that it may be related to the ability to purify the respective monomers. Despite this, copolymerization of the different glyoxylates with ethyl glyoxylate such as for polymers 14 and 15 surprisingly resulted in molecular weight characteristics similar to those of the PEtGs, even at 38-55 mol % of the co-monomer. The polydispersity indices (PDIs) ranged from ~1.3-2.6.

TABLE 1

| | Molecular weights, physical characteristics, and thermal properties of polymers | | | | | | | |
|---|---|---|---|---|---|---|---|---|
| | | | | TGA | | DSC | | |
| Polymer | $M_n$ (kg/mol) | $M_w$ (kg/mol) | PDI | $T_{98\%}$ (° C.)[1] | $T_o$ (° C.)[2] | $T_p$ (° C.)[3] | $T_g$ (° C.) | $T_m$ (° C.) |
| 1 | 103 | 266 | 2.6 | 84 | 148 | 165 | −32 | — |
| 2 | 27 | 66 | 2.5 | 168 | 190 | 202 | −1 | — |
| 3 | 31 | 59 | 1.9 | 161 | 173 | 203 | −3 | — |
| 4 | 53 | 91 | 1.7 | 164 | 202 | 228 | −9 | — |
| 11 | 3.8 | 4.8 | 1.3 | 139 | 196 | 220 | 25 | — |

TABLE 1-continued

Molecular weights, physical characteristics, and thermal properties of polymers

|  |  |  |  | TGA | | DSC | | |
|---|---|---|---|---|---|---|---|---|
| Polymer | $M_n$ (kg/mol) | $M_w$ (kg/mol) | PDI | $T_{98\%}$ (° C.)[1] | $T_o$ (° C.)[2] | $T_p$ (° C.)[3] | Tg (° C.) | Tm (° C.) |
| 12 | 5.0 | 9.8 | 1.9 | 180 | 218 | 247 | −30 | — |
| 13 | 2.1 | 3.5 | 1.6 | 147 | 195 | 229 | 12 | — |
| 14 | 40 | 81 | 2.0 | 169 | 181 | 203 | 15 | — |
| 15 | 11 | 22 | 2.0 | 164 | 208 | 236 | −10 | — |
| 21b | 40 | 85 | 2.1 | 160 | 203 (375)[4] | 232 (398)[4] | −5 | 46 |

[1]$T_{98\%}$ represents the temperature at which 98% of the mass is still present.
[2]$T_o$ is the onset degradation temperature.
[3]$T_p$ is the peak degradation temperature.
[4]The values in brackets represent the values for the second stage of this two-stage decomposition.

The thermal properties of the polymers were analyzed by thermogravimetric analysis (TGA) and differential scanning calorimetry (DSC). Regardless of the end-cap used, the $T_{98\%}$ of PEtGs 2, 3, 4 were approximately 160° C., which is considerably higher than was observed for the non-end-capped PEtG 1 ($T_{98\%}$=84° C., FIG. 1(a)). These TGA results strongly suggest that the isolated polymers are indeed well capped and that the end-cap signals in the $^1$H NMR spectra are not due to small amounts of small molecule contamination. Similarly, the thermal stabilities of the different polyglyoxylates end-capped by NVOC-Cl are provided in FIG. 1(b). Polymer 12, poly(n-butyl glyoxylate), shows the highest thermal stability, as the $T_{98\%}$, $T_o$, and $T_p$ were improved by approximately 20° C. compared to polymer 4. However, in general, all polymers showed similar thermal stability despite the variety of different side-chains and orders of magnitude differences in molecular weight. This strongly suggests that the thermal stability of polyglyoxylates is determined mostly by the nature of the acetal backbone linkages regardless of the other structural variations. For the block copolymer 21b there are clearly two stages corresponding to degradation of the PEtG block and PEG blocks in the triblock polymer (FIG. 1(c)). TGA also showed a ratio of 9:1 for the mass losses in the two stages, which is consistent with the ratio of the different blocks based on $^1$H NMR spectroscopy.

The DSC data showed that the glass transition temperatures ($T_g$s) were very similar for all well end-capped PEtGs 2-4, around −5° C. This was significantly higher than the non-end-capped PEtG 1 which had a $T_g$ of −32° C. However, for the different polyglyoxylates the $T_g$ ranged from −30° C. for poly(n-butyl glyoxylate) 12, to 25° C. for poly(methyl glyoxylate) 11. The surprisingly low $T_g$ of 12° C. for the poly(benzyl glyoxylate) 13, which would be expected to have a considerably higher $T_g$ due to the bulky aromatic side chains, can be possibly explained by the very low molecular weight (2000 g/mol) relative to the other polymers. This variation can likely be attributed in part to the varying molecular weights of these polymers (all considerably lower than those of the PEtGs) and the differing mobility of each side chain. The triblock copolymer 21 was also semicrystalline with a $T_m$ of 46° C. resulting from the PEG block.

The glass transition temperature can also be significantly increased through copolymerization, as both the PEtG-co-poly(methyl glyoxylate) and PEtG-co-poly(n-butyl glyoxylate), show higher $T_g$s, by almost 20° C., than either the simple poly(ethyl glyoxylate) or poly(n-butyl glyoxylate). This is potentially due to the ability to incorporate the thermal properties of the butyl and methyl side-chains into a longer chain than could be obtained from the homopolymerization of each monomer alone. Thus, a range of $T_g$s, and degrees of crystallinity are accessible with these polyglyoxylates.

Controlled Degradation Study

Figure 2:
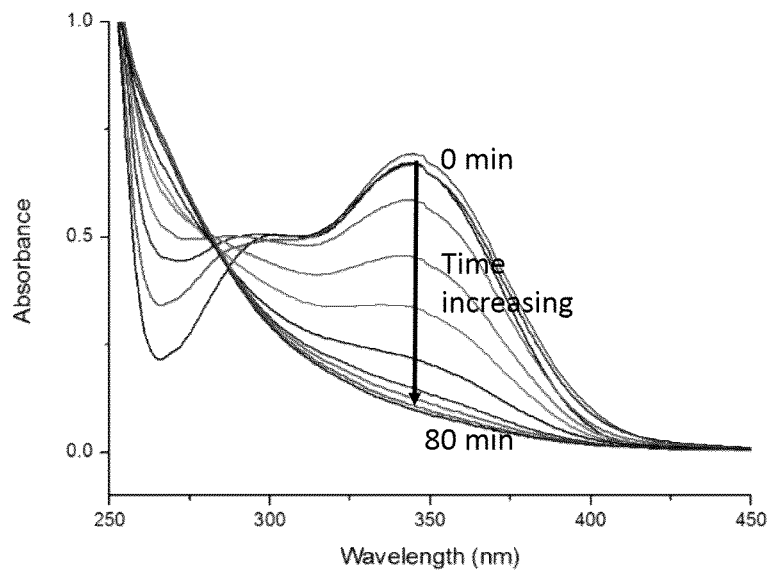
FIG. 2 shows UV-visible spectra of polymer 4 following different periods of irradiation with UV light, demonstrating the reduction in the absorbance of the peak at 341 nm. This illustrates successful removal of the end-cap by UV light.

The kinetics of the triggered polymer degradation was studied. UV-visible spectroscopy was used to determine the required irradiation time for NVOC cleavage and the experimental results are provided in FIG. 2. Prior to irradiation, there was a clear peak at 341 nm corresponding to the absorbance of the end-cap; however, after 40 minutes of irradiation the intensity of the signal had greatly decreased. After 80 minutes of irradiation, the peak had disappeared, indicating complete cleavage of polymer the end-cap.

Figure 3:
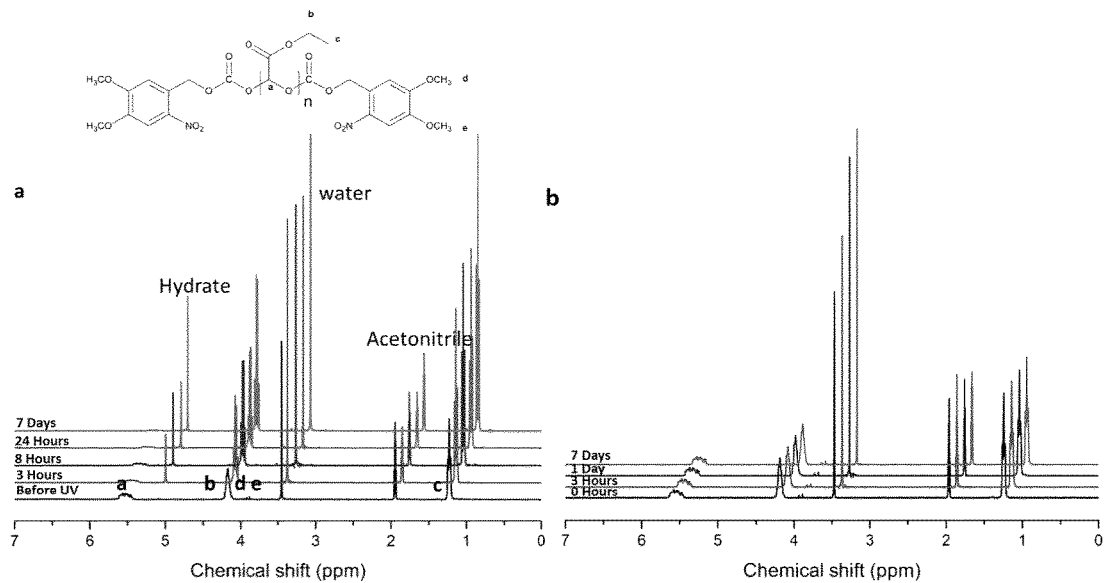
FIG. 3 shows $^1$H NMR spectra of (a) polymer 4 after UV irradiation; (b) polymer 4 without UV irradiation, following incubation in 9:1 acetonitrile-$d_3$:$D_2O$ for varying time periods. This demonstrates that degradation occurs selectively upon irradiation.
Figure 4:
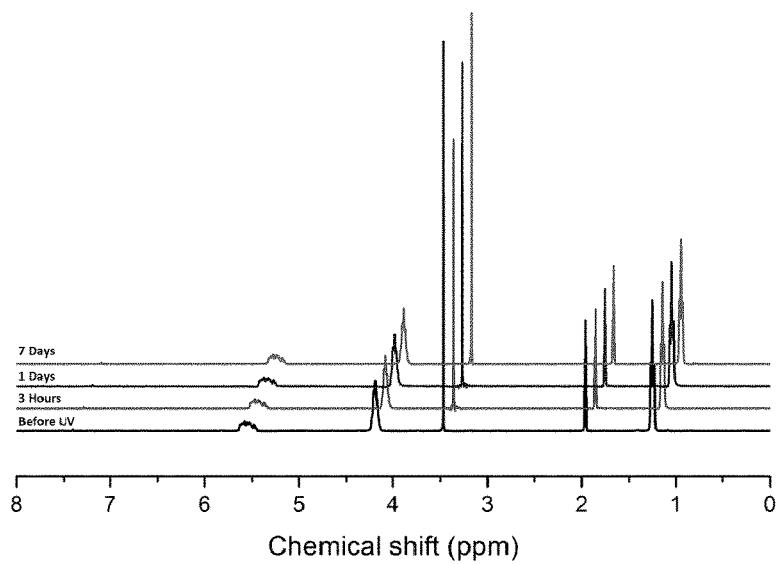
FIG. 4 shows $^1$H NMR spectrum of polymer 3 after UV irradiation and incubation in 9:1 acetonitrile-$d_3$:$D_2O$ for varying time periods. No changes were observed, indicating that the polymer is stable under these conditions.

As shown in FIG. 3(a) for PEtG 4, the NMR spectra before and after 80 minutes of irradiation support the successful cleavage of the end-cap and were used to quantify the degree of depolymerization as the reaction proceeded (FIG. 3(a)). Before irradiation, the polymer resonances were three clear broad peaks, and the peaks for two methoxy groups (4.06 ppm and 3.97 ppm) on the end-cap were also observable (black trace). However, after irradiation and then incubation in 9:1 acetonitrile-$d_3$/$D_2O$ for 3 hours, these two resonances had clearly disappeared, suggesting the end-cap of polymer 4 was indeed successfully eliminated by the UV light (red trace). Furthermore, the broad peak at 5.5 ppm decreased, indicating that the depolymerization of the backbone of polymer 4 was occurring. Meanwhile, a new peak (5.09 ppm) appeared, and the broad peaks of the ethyl group began to resolve into the quartet (4.17 ppm) and triplet (1.23 ppm) expected from the small molecule depolymerization product ethyl glyoxylate hydrate (EtGH) (Scheme 2). All of these changes are indicative of the depolymerization of polymer 4. Eight hours later, based on the integration of the broad peak at 5.5 ppm, more than half of the polymer had already decomposed into EtGH. After 24 hours, more than 70% of the polymer had depolymerized. By comparison, as shown in FIG. 3(b) for a non-irradiated sample of polymer 4 after seven days in the solvent mixture, the end-capped polymer remains unchanged even in the presence of water. Similarly, for the benzyl chloroformate end-capped PEtG 3, the polymer remains unchanged after seven days even though it is exposed to UV light (FIG. 4). This indicates that the degradation is not due to backbone cleavage of the polymer, but is induced by the UV light.

Figure 5:
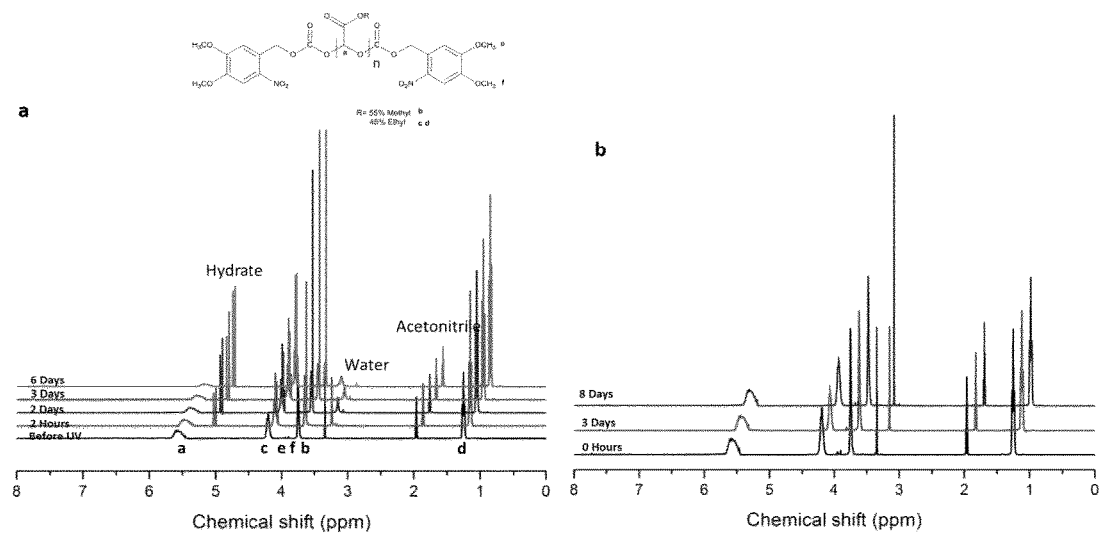
FIG. 5 shows $^1$H NMR spectra of (a) polymer 14 after UV irradiation; and (b) polymer 14 without UV irradiation, following incubation in 9:1 acetonitrile-$d_3$:$D_2O$ for varying time periods. This demonstrates that degradation occurs selectively upon irradiation also for a random copolymer.
Figure 6:
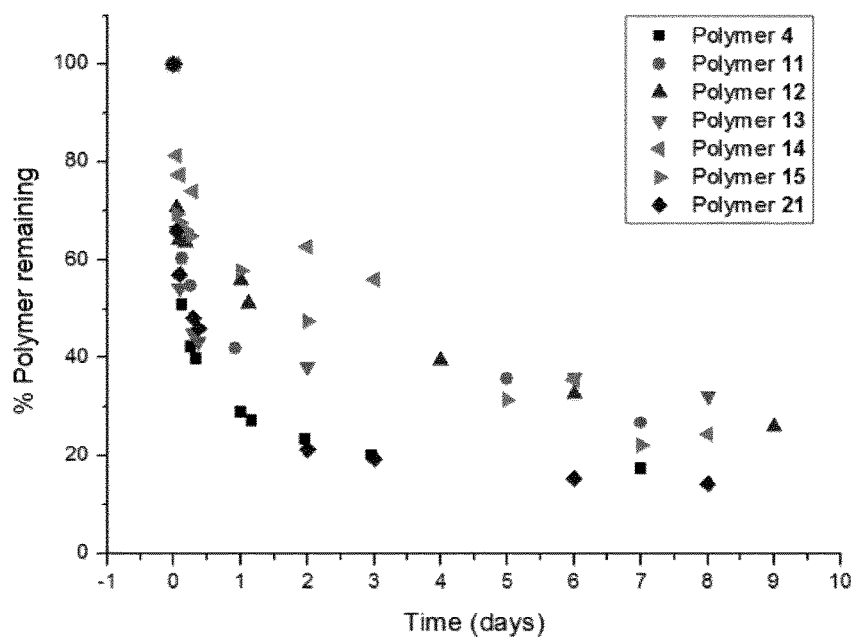
FIG. 6 shows degradation profiles of different NVOC end-capped polymers and copolymers. This shows that all of the polymers depolymerize upon irradiation with UV light.

The degradations of the other polyglyoxylates 11-15 and triblock polymer 21 were investigated in the same manner. For example polymer 14, the copolymer of ethyl and methyl glyoxylate, was subjected to the same irradiation and incubation sequence. Just as for polymer 4, before irradiation, the polymer showed a series of broad peaks and the four small resonances corresponding to the end-cap. Following irradiation by UV light (FIG. 5(a)), the broad peak at 5.51 ppm started to decrease, and two new peaks at 5.11 ppm and 5.08 ppm, characteristic of methyl glyoxylate hydrate and EtGH, respectively, began to increase, and all the other broad peaks transformed into sharper signals typical of a small molecule. The control (non-irradiated) polymer (FIG. 5(b)) did not show any signs of degradation, even after eight days. This suggested that the copolymers degrade similarly to the homopolymers, opening the door for the preparation of a wide variety of mixed glyoxylate polymers. The percent degradation versus time for all the polymers and copolymers is plotted in FIG. 6. For almost all polymers, at least 70% of the material degraded in the first week following UV irradiation, while the non-irradiated polymers remained stable.

Figure 7:
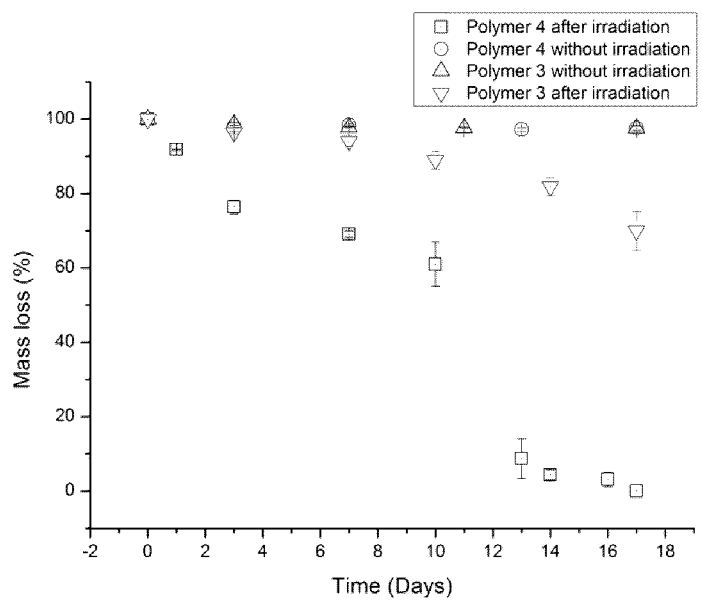
FIG. 7 shows rates of mass loss from films of PEtGs 3 and 4 with and without UV irradiation. This shows that films of polymer degrade following irradiation with UV light, much more rapidly than the controls.
Figure 8:
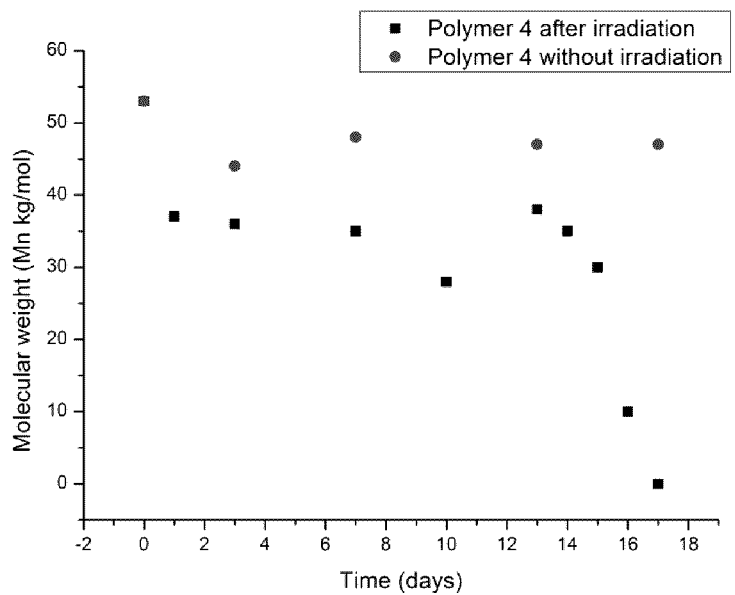
FIG. 8 shows $M_n$ changes for polymer 4 in films after UV irradiation and without irradiation following incubation in aqueous buffer (pH=7.4)

To further support the depolymerization studies conducted in solution and demonstrate the use of these polymers as stimuli-responsive coatings, films of PEtG 4 were subjected to a mass-loss study. Samples of polymer 4 were deposited on glass slides (60 slides), and half of the slides were exposed to UV light, while the other half were kept in the dark. The slides were then immersed in a neutral aqueous buffer solution (pH=7.4) and the masses of the slides were measured at selected times until the polymers were completely degraded. As shown in FIG. 7, the irradiated samples of polymer 4 started degrading immediately from the first day in buffer solution, with steady mass loss over the next 17 days until they had completely depolymerized and dissolved into the water. However, for the non-irradiated polymer 4, less than 4% of weight loss was observed after the same 17-day period. This small amount of weight loss is likely due to non-specific ester hydrolysis of the side chains. As controls, the benzyl chloroformate end-capped polymer 3 (both irradiated and non-irradiated) were treated in the same manner. Interestingly, the irradiated polymer 3 showed around 30% mass loss after 17 days. This could be result from the damage of long time UV irradiation on the polymer backbone or through the partial cleavage of the benzyl carbonate end-cap by an inefficient photochemical process. However, compared to the 100% mass loss of irradiated polymer 4, it appears that most of mass loss for irradiated-polymer 4 was due primarily to loss of the end-cap and the resulting end-to-end depolymerization.

After the measurement of mass loss, the material remaining on the slide was examined by SEC to determine to what degree depolymerization had occurred, as small levels of non-specific hydrolysis and slow depolymerization would result in a lower molecular mass, but may not result in dissolution of the material. The initial $M_n$ of polymer 4 was 53 kg/mol, but after irradiation by UV light, the $M_n$ of polymer 4 decreased to about 37 kg/mol in the first day. Over the next 15 days, the $M_n$ exhibited very little change but at the same time the mass of the film kept decreasing. This suggests that the film was likely disintegrating via a surface erosion process. After 16 days, the entire film had degraded leaving a very small amount of residue with an $M_n$ of 10 kg/mol. In comparison, the $M_n$ of the non-irradiated control remained around 47 kg/mol.

Figure 9:
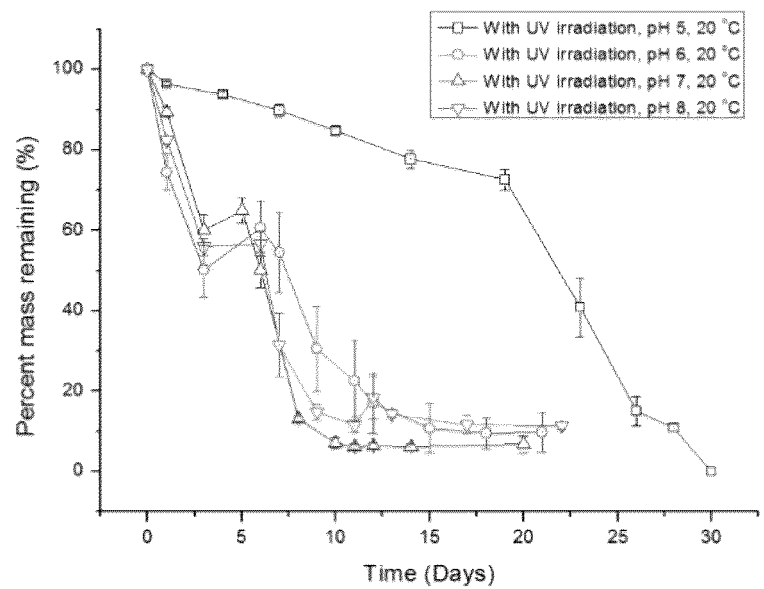
FIG. 9 shows the rate of mass loss from films of polymer 4 following irradiation with UV light and incubation in buffers with varying pH.
Figure 10:
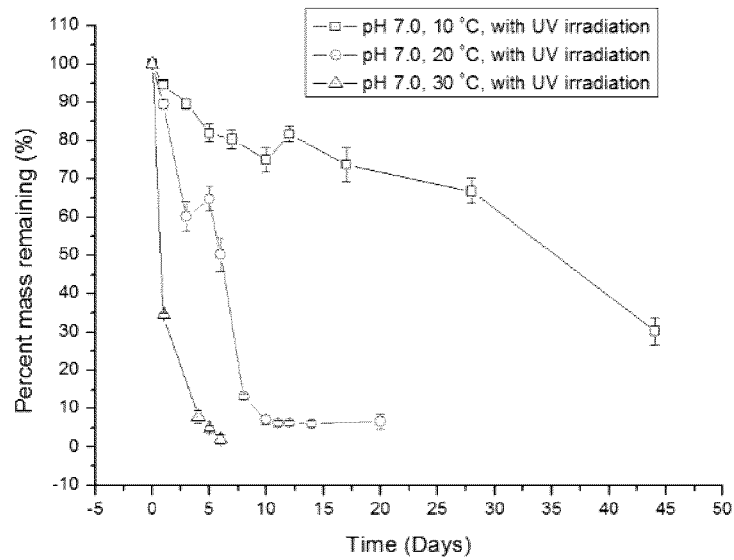
FIG. 10 shows the rate of mass loss from films of polymer 4 following irradiation with UV light and incubation at pH 7 at varying temperatures.

The effects of pH and temperature on the degradation rates of films were also examined. As shown in FIG. 9, despite the polyacetal backbone, PEtG surprisingly degraded more slowly at pH 5 than at pH 6-8. At pH 5.0, the polymer film required almost 30 days to reach complete degradation, whereas if the pH was increased to 6.0, the time required for complete degradation was almost decreased in half. With further increases of pH, the degradation time did not change significantly. Increasing the temperature from 10° C. to 30° C., the degradation rate increased as shown in FIG. 10. For example, 1 day was required to achieve 65% degradation at 30° C., but 44 days were needed at 10° C. Moreover, for all the degradation profiles, a plateau was observed at ~20% degradation of the films by mass. The cause of this plateau is believed to be related to a unique combination of the end-to-end depolymerization mechanism and the surface erosion. As depolymerization occurs from end-to-end and the reactions are greatly accelerated by exposure to water, we propose polymer chains with termini near the film surface degrade rapidly in the initial stage. After this, time is required for water to penetrate the films, resulting in initiation of depolymerization of the remaining chains.

Assembly of PEG-PEtG-PEG Triblock Copolymers in Aqueous Solution

Figure 11:
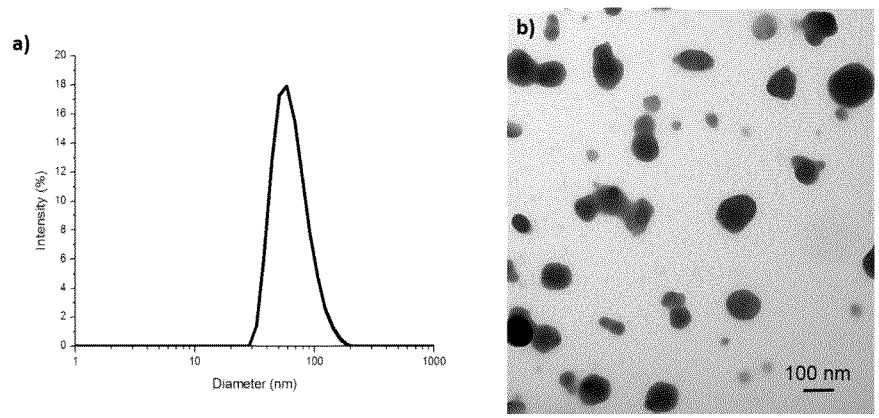
FIG. 11 shows a) a dynamic light scattering (DLS) trace of a suspension of micelles formed from polymer 21a and b) a transmission electron microscopy (TEM) image of the same micelles.
Figure 12:
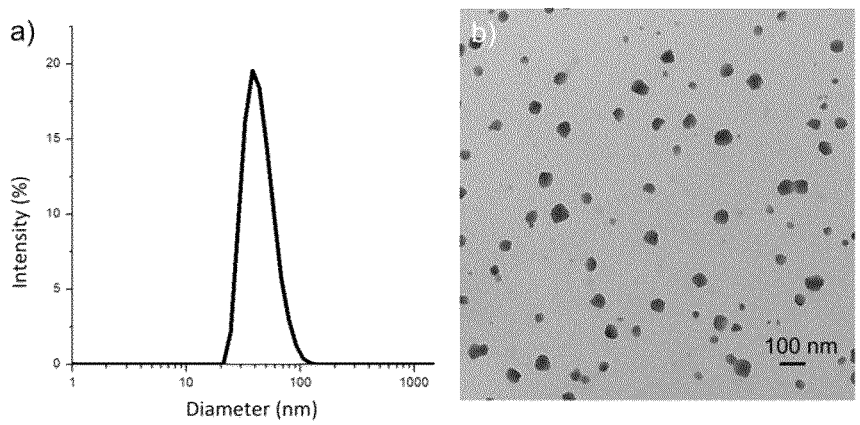
FIG. 12 shows a) DLS trace of a suspension of micelles formed from polymer 21 b and b) a TEM image of the same micelles.
Figure 13:
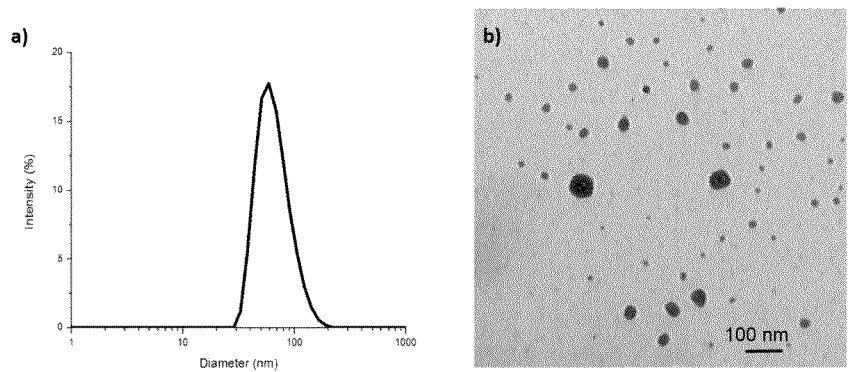
FIG. 13 shows a) a DLS trace of a suspension of micelles formed from polymer 21c and b) a TEM image of the same micelles.

The copolymer PEG-PEtG-PEG (21a), containing a PEG block of 750 g/mol, PEG-PEtG-PEG (21b), containing a PEG block of 2000 g/mol, and an additional PEG-PEtG-PEG (21c), containing a PEG block of 5000 g/mol were used in this study. Using a nanoprecipitation/solvent exchange procedure, the polymer was dissolved into DMSO and rapidly injected into stirring deionized water or buffer solution. The DMSO was then removed by dialysis against deionized water. The sizes and size distributions of the nano-aggregates were characterized by dynamic light scattering (DLS). The results are summarized in Table 2 and FIGS. 11-13. The Z-average diameters of the nano-aggregates were all below 100 nm for polymers 21a, 21b and 21c. The polydispersity indices (PDI) were relatively narrow, particularly for 21b.

TABLE 2

DLS characterization data for assemblies formed from PEG-PEtG-PEG block copolymers

| Triblock copolymers | Micelle | | |
|---|---|---|---|
| | z-average (nm) | PDI | Hydrophilic block mass fraction |
| PEG-PEtG (59 kDa)-PEG (750 Da) 21a | 78 | 0.12 | 2.48% |
| PEG-PEtG (42 kDa)-PEG (2 kDa) 21b | 52 | 0.06 | 8.70% |
| PEG-PEtG (48 kDa)-PEG (5 kDa) 21c | 89 | 0.19 | 17.24% |

Figure 14:
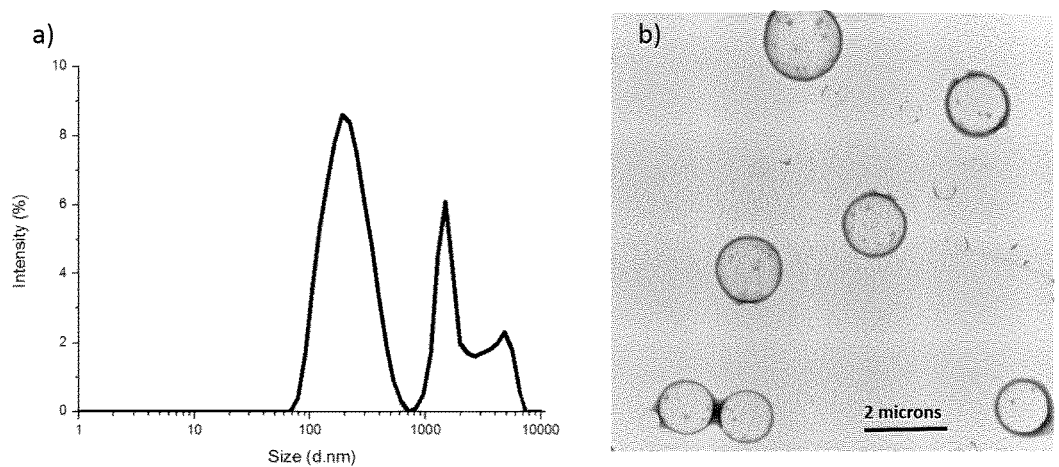
FIG. 14 shows a) a DLS trace of a suspension of vesicles formed from polymer 21a and b) a TEM image of the same vesicles.
Figure 15:
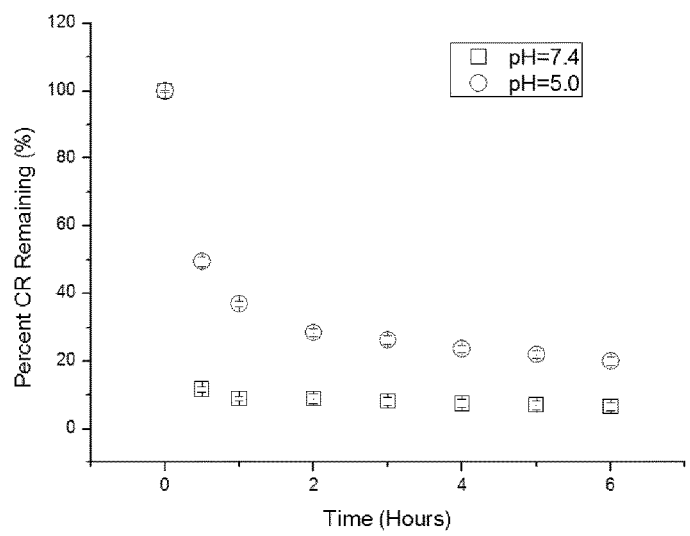
FIG. 15 shows decreases in the DLS count rate (CR) as a function of time and pH for micelles formed from polymer 21c. The decreasing CR is consistent with breakdown of the micelles.

Transmission electron microscopy (TEM) was also used to confirm the presence of the nano-aggregates and their morphologies. TEM images showed that all of the copolymers formed solid spherical aggregates, which suggests that they formed micelles or compound micelles. Given the low hydrophilic mass fractions of 21a and 21b, it was surprising that they formed micellar nano-aggregates based on the guidelines of Discher and Eisenberg[38] which suggest that the vesicles will be formed if the hydrophilic fraction was less than 40%. This can likely be attributed to a kinetic trapping effect as the DMSO solution of polymer was rapidly injected into the aqueous solution. In contrast, when 21a was dissolved in THF and water was slowly added to this solution, it was possible to form vesicles as observed via TEM and DLS in FIG. 14. Overall, this self-assembly work demonstrates that the morphologies of the assemblies formed by polyglyoxylates can be readily tuned by varying the ratios of the hydrophilic and hydrophobic blocks as well as the assembly procedure. These assemblies will be useful for encapsulating and releasing payloads in a stimuli-responsive manner. The linker molecule connecting the PEtG and PEG is photo-cleavable. Therefore, with UV irradiation, it is possible to separate the triblock polymer into its constituent blocks and initiate the depolymerization of the hydrophobic PEtG. This should lead to the disassembly of the micelles. By DLS with a fixed detector attenuation, it was possible to monitor the disintegration of the micelles by the change in count rate, as the count rate is proportional to the number of scattering species and their sizes. In this study, polymer 21c was chosen for micelle preparation. The micelle suspensions were prepared in two different buffer solutions, one at pH 7.4, and another at pH 5.0. After the initial micelle suspensions were measured by DLS, the samples were put into a UV box (23 mW/cm$^2$) and irradiated for 20 minutes. The irradiation time was previously determined by a series of control studies in which irradiation was performed for periods ranging from 5 minutes to 60 minutes. As shown in FIG. 15, after UV irradiation, reductions of almost 90% and 50% in the count rate were observed at pH 7.4 and pH 5.0, respectively. These changes in count rates suggest a much faster degradation rate of PEtG in a fully aqueous system than what was described in the mixture of 9:1 acetonitrile:water. Moreover, the data suggest that the micelles disintegrated more rapidly in neutral conditions than in acidic conditions, which is in agreement with the mass loss studies of the films described above.

Figure 16:
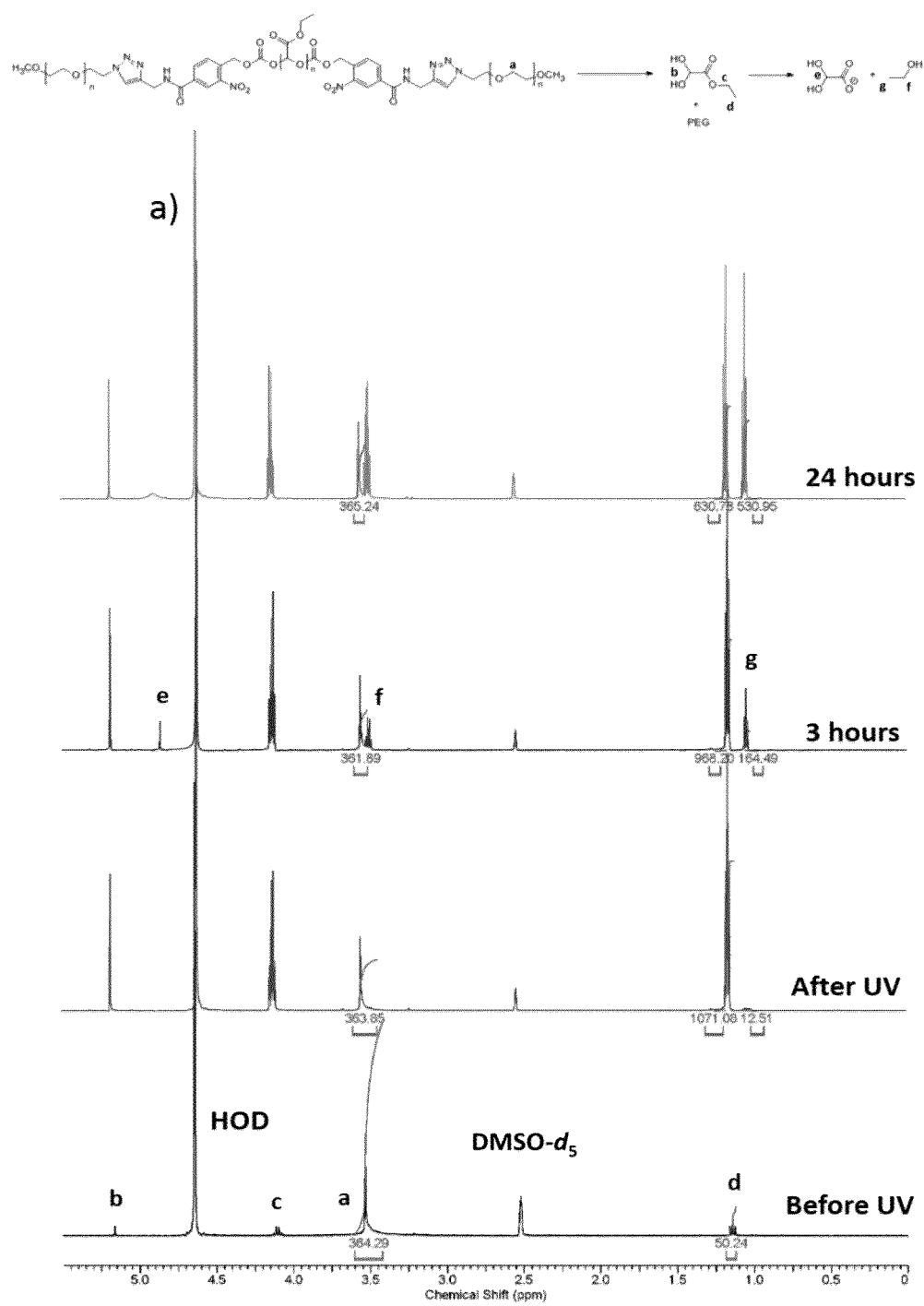
FIG. 16 shows $^1$H NMR spectra of micelles formed from polymer 21b following irradiation with UV light. The lack of peaks corresponding to the core forming polyglyoxylate block before UV irradiation is consistent with the formation of micelles. The appearance of sharp peaks following irradiation is consistent with the degradation of the polyglyoxylate block into monomers.
Figure 17:
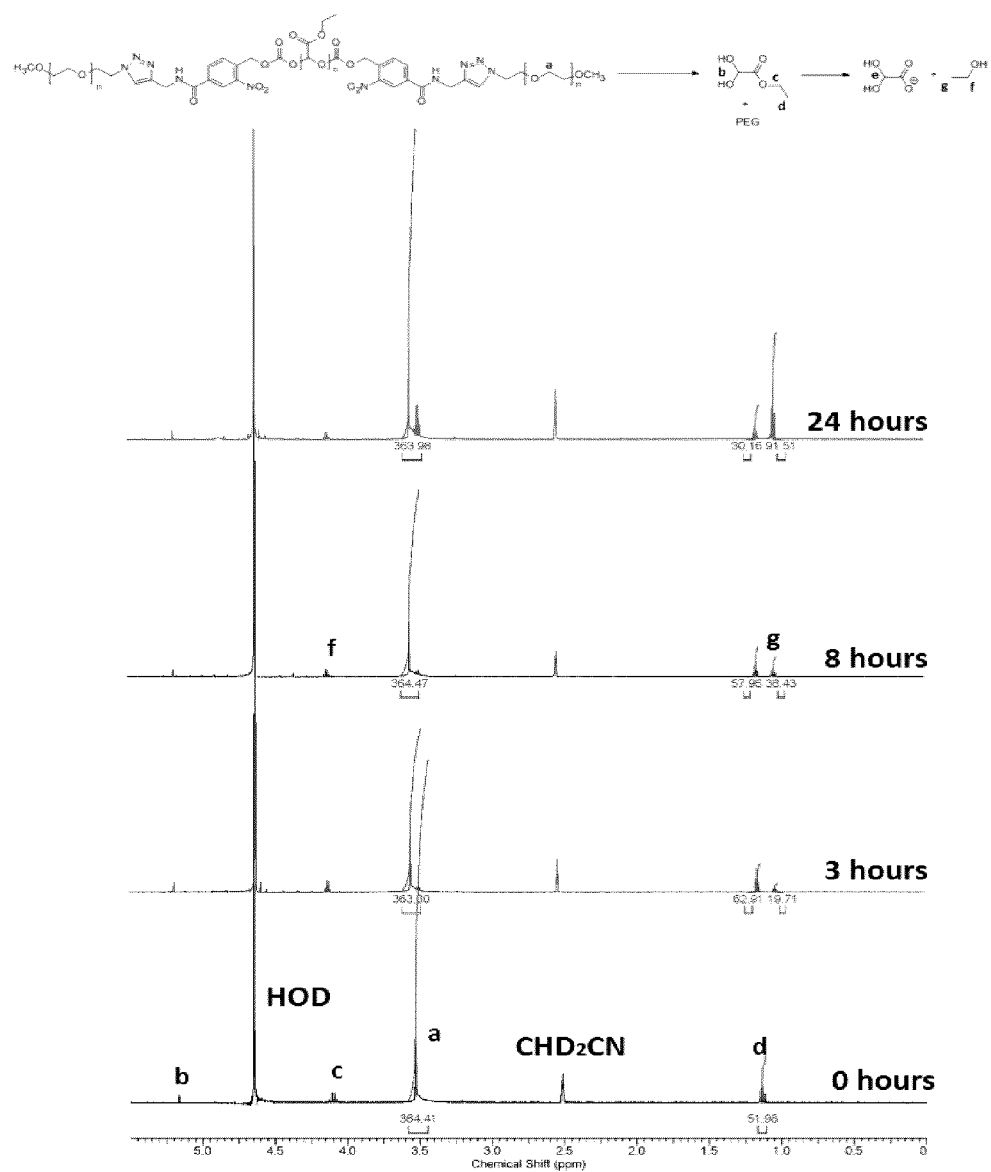
FIG. 17 shows $^1$H NMR spectra of micelles formed from polymer 21b without irradiation with UV light. The lack of peaks corresponding to the core forming polyglyoxylate block before UV irradiation is consistent with the formation of micelles. The lack of appearance of sharp peaks corresponding to monomers supports the stability of the micelles over 24 hours in the absence of the stimulus.
Figure 18:
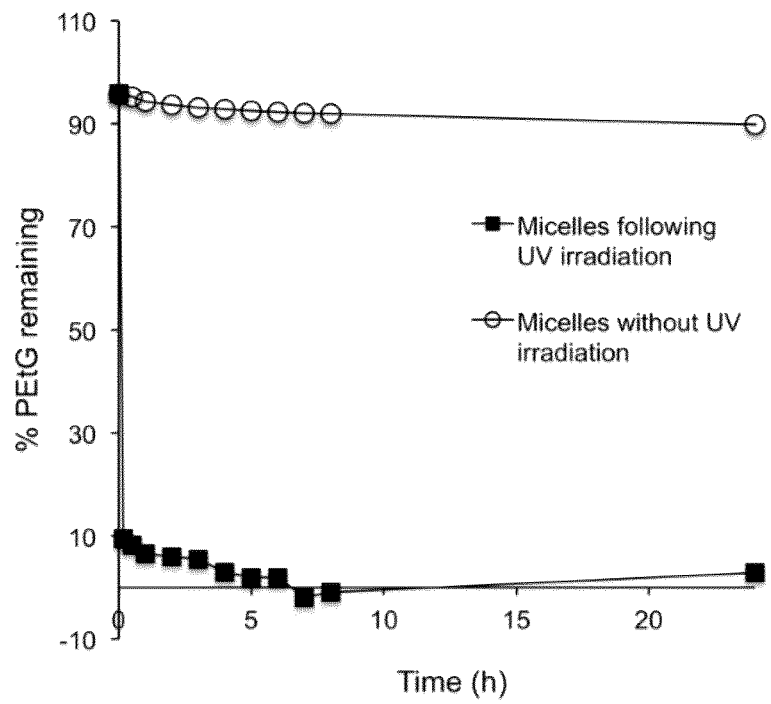
FIG. 18 shows a comparison of the % polyglyoxylate remaining at various time points either with or without UV irradiation.

The self-assembly and depolymerization were also studied by $^1$H NMR spectroscopy. In this case, the assemblies were prepared by nanoprecipitation of a DMSO-$d_6$ solution of the polymer into pH 7.4 phosphate buffered $D_2O$ (DMSO-$d_6$:$D_2O$=1:5). For practical reasons, the DMSO-$d_6$ was not removed by dialysis. Consistent with the self-assembly of 21 b into micelles under these conditions, only the peak corresponding to the PEG block, and no peaks corresponding to the PEtG block were observed in the NMR spectrum prior to UV irradiation (FIG. 16). However, a $^1$H NMR spectrum taken immediately following UV irradiation showed greater than 90% degradation of PEtG block (FIG. 16), as measured by the appearance of peaks corresponding to EtGH. Subsequently, the resulting EtGH underwent ~45% hydrolysis to glyoxylic acid and ethanol over 24 h at 37° C. These results confirm that the depolymerization following end-cap cleavage is much faster in these buffered aqueous conditions than in 9:1 CD$_3$CN:H$_2$O, and also that the nanoscale dispersion of PEtG into water through self-assembly of copolymer 21b results in much more rapid depolymerization than in the films of pure PEtG described previously In contrast, a control sample of micelles that was not irradiated underwent less than 10% degradation over 24 h. (FIG. 17, 18)

Figure 19:
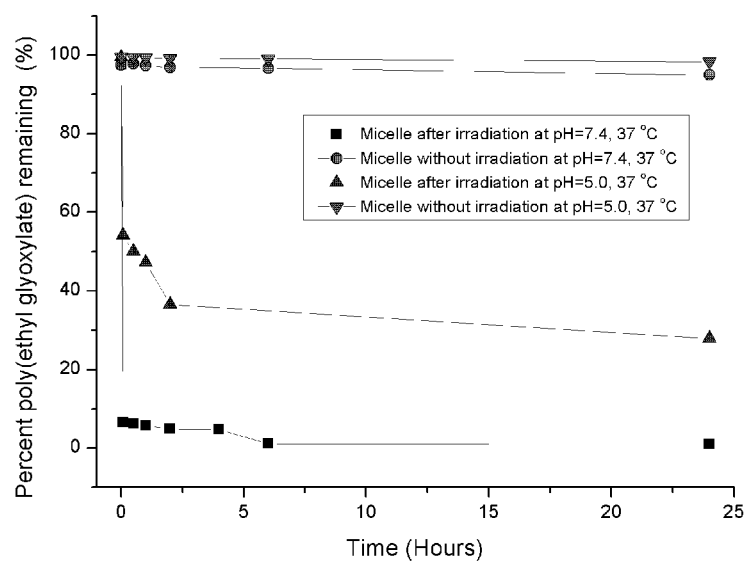
FIG. 19 shows a comparison of the % polyglyoxylate remaining at various time points either with or without UV irradiation at pH 7.4 or pH 5.0. This shows that degradation is more rapid at neutral pH.

The NMR degradation study of the micelles was also extended to copolymer 21c at different pHs. At pH 7.4, the PEtG showed fast degradation with more than 90% of the polymer degraded by the first measurement (FIG. 19, 5 min). However, in pH 5.0 buffer solution, only ~50% of PEtG had degraded by the first measurement. These results are consistent with the DLS studies, and also confirm that the disassembly of micelles observed by DLS were the result of the degradation of PEtG block upon end-cap cleavage by UV irradiation.

Model Payload Incorporation and Release Studies

Figure 20:
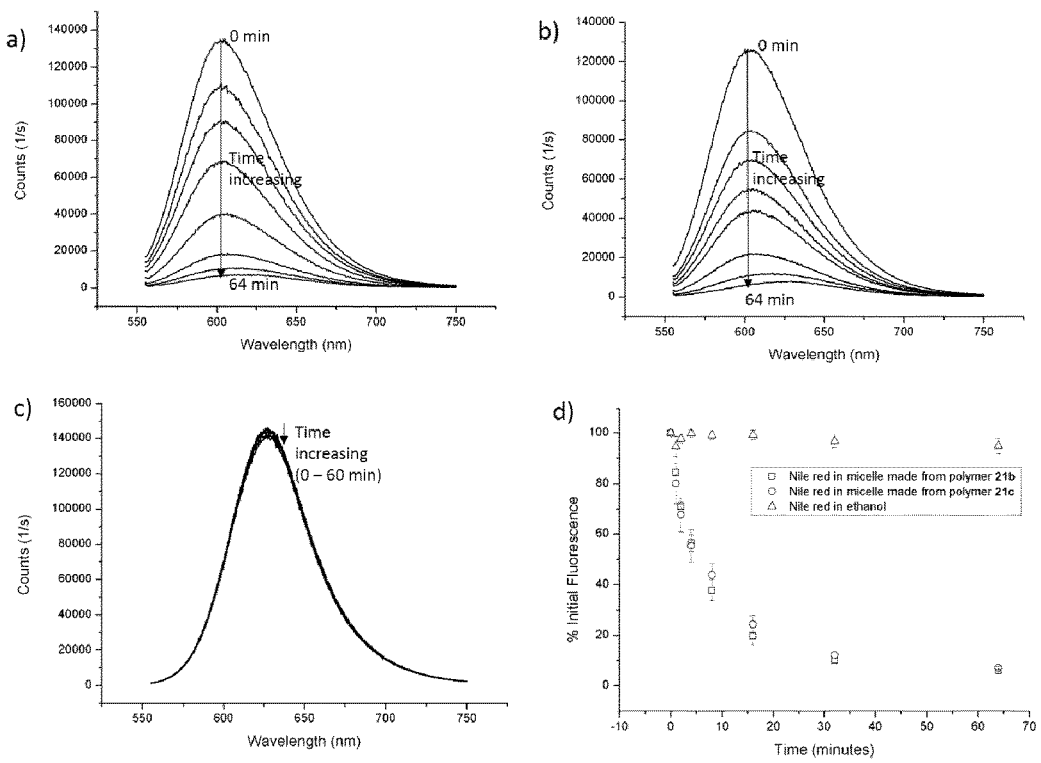
FIG. 20 shows the change of fluorescence intensity with different UV irradiation times for micelles formed from a) 21b and b) 21c; c) nile red in ethanol demonstrating its photostability; d) a comparison of the % initial fluorescence versus time for these systems.

In order to demonstrate the encapsulation and release abilities of the micelles, the hydrophobic dye nile red was used as a model payload. This molecule has strong fluorescence emission at 550 nm when it is dissolved into organic solvent or incorporated into a hydrophobic core of a micelle, but the emission is negligible in water due to aggregation and quenching.[39] This allows its release from the micelle core to be directly probed. In this experiment, both micelles formed from copolymer 21b and 21c were used. The micelle suspensions (in water) were irradiated for time periods ranging from 1 minute to 64 minutes, and then the fluorescence intensity was record immediately after each irradiation. As shown in FIGS. 20a, 20b and 20d, the intensity of nile red fluorescence in micelles both from 21b and 21c showed dramatic decreases for the first 16 minutes of irradiation, but after about 30 minutes of irradiation, the intensity almost did not decrease significantly further. This experiment provides an indication of the irradiation time (range from 16 minutes to 32 minutes) needed for complete disintegration of micelles containing the dye. In addition, nile red dissolved in ethanol served as a control. When subject to the same irradiation periods as the micelles, no detectable decrease in intensity was observed (FIGS. 20c and 20d). This confirms that the decreases in nile red fluorescence were indeed due to its release from the micelles rather than photodegradation of the dye.

Figure 21:
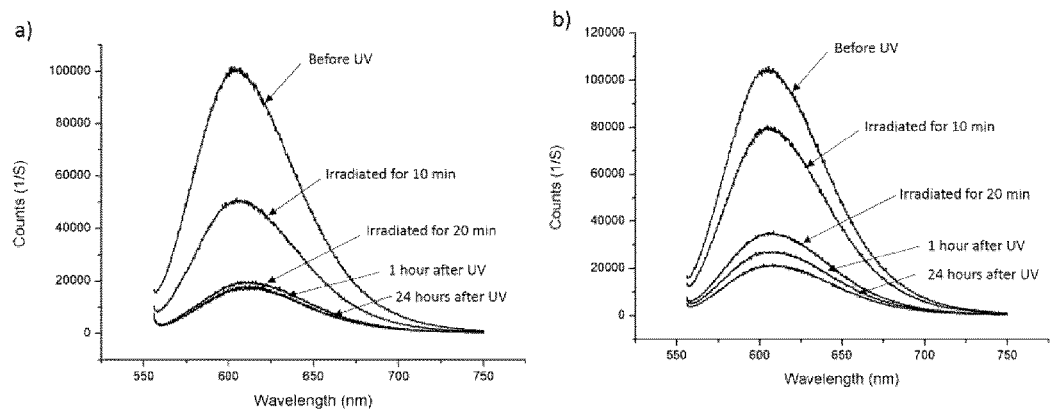
FIG. 21 shows the change in encapsulated nile red fluorescence intensity following different irradiation times for micelles at a) pH 7.4 and b) pH 5.0.

The release study was then conducted in different buffer solutions at 37° C. with micelles formed from 21c. As shown in FIGS. 21a and 21b, there was an almost 50% decrease in fluorescence intensity after 10 minutes of irradiation and more than 80% decrease after 20 minutes of irradiation at pH 7.4. However, for the micelle suspension at pH 5.0 only a 20% intensity decrease was observed after 10 minutes and another 40% decrease was observed after 20 minutes irradiation. In addition, when the micelles were subsequently incubated over longer time periods, the fluorescence intensity continued to decrease at pH 5.0. In contrast, no further decrease was observed for the suspension at pH 7.4 suggesting that release was already complete at 20 min. Therefore, the micelles can undergo a rapid burst release of nile red at neutral conditions, whereas the release is more gradual at slightly acidic conditions. This result is consistent with the degradation of the micelles studied by DLS and NMR.

Doxorubicin (DOX) Incorporation and Release Studies

Figure 22:
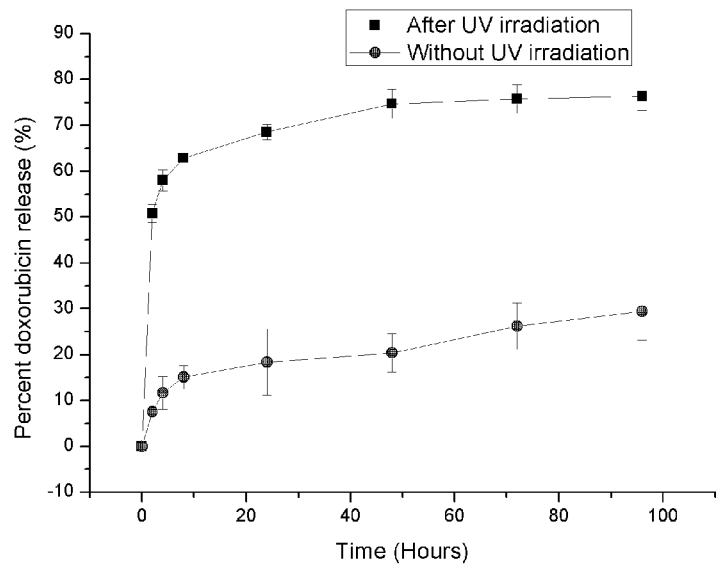
FIG. 22 shows the difference in doxorubicin release rates from micelles formed from polymer 21 b either with or without UV irradiation. This shows that drug release can be selectively triggered using light as a stimulus.

The anti-cancer drug DOX was incorporated into micelles made from polymer 21 b using the same procedure as the nile red incorporation except that the excess DOX was removed by dialysis against pH 5.0 buffer solution for 48 hours. The loading capability was ~10% by weight, as measured by the UV-vis absorption at 500 nm. Then the release of DOX from the micelles with and without UV irradiation were both monitored over 96 hours at pH 5.0, 37° C. As shown in FIG. 22. After UV irradiation, the system showed burst releasing of DOX in the first 10 hours, and a final 80% releasing was achieved in 96 hours. However, without UV irradiation, the system showed much slower release with only less than 30% of drug released during the same time period. This demonstrates the utility of polyglyoxylate micelles for releasing drugs in a controlled manner.

Synthesis of PDMAEMA-PEtG-PDMAEMA Triblock Copolymers

Different approaches towards block copolymer synthesis are also possible. It was shown to be possible to polymerize the PDMAEMA from a PEtG macroinitiator. First, the previously reported azide terminated initiator 22[40] was prepared and coupled to polymer 19 through CuAAC to obtain polymer 23 as shown in Scheme 6. Then, polymer 23 was used as a macroinitiator to grow PDMAEMA on the both sides of polymer through atom-transfer radical polymerization to provide PDMAEMA-PEtG-PDMAEMA amphiphilic triblock copolymer 24.

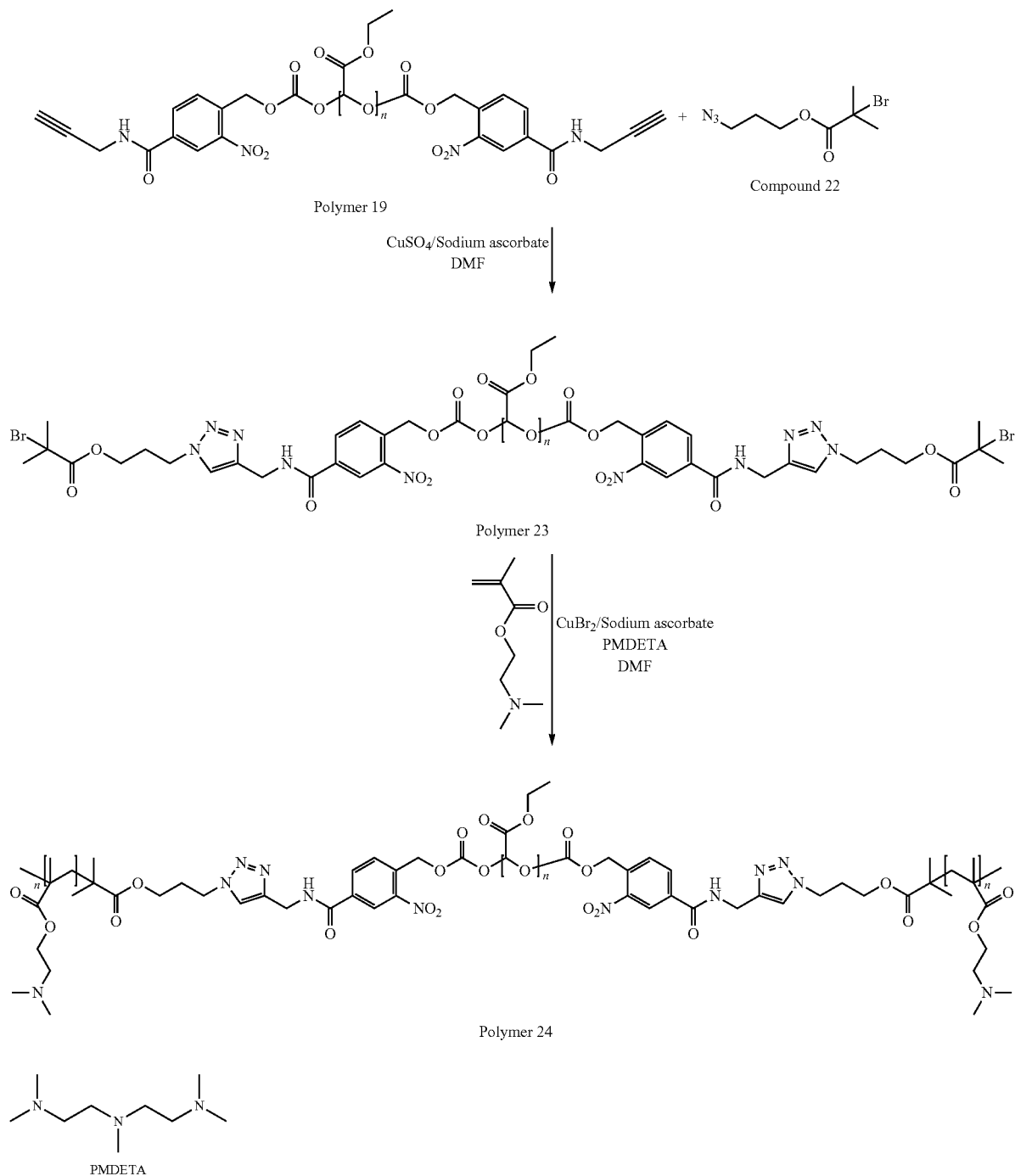

Scheme 6
Synthesis of PDMAEMA-PEtG-PDMAEMA triblock polymer

Synthesis of Polyglyoxylates with Functional Side Chains

Methods of the invention make possible the synthesis of novel glyoxylates with functional side chains. These include, for example, cross-linking moieties such as vinyl groups (25) and (26), functional handles such as azides (27), alkynes (28), halides (29), and protected alcohols (30) which permit functionalization or cross-linking after a polymer has been prepared, and pharmaceutically active sidechains (31-33):

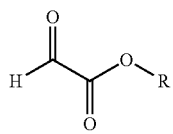

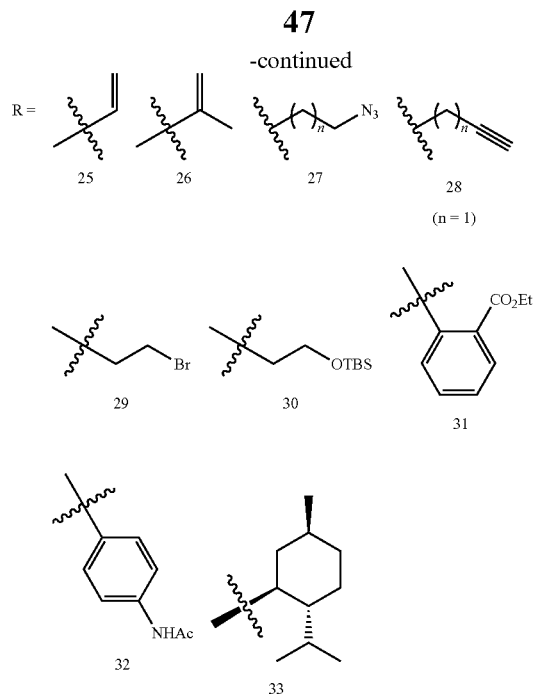

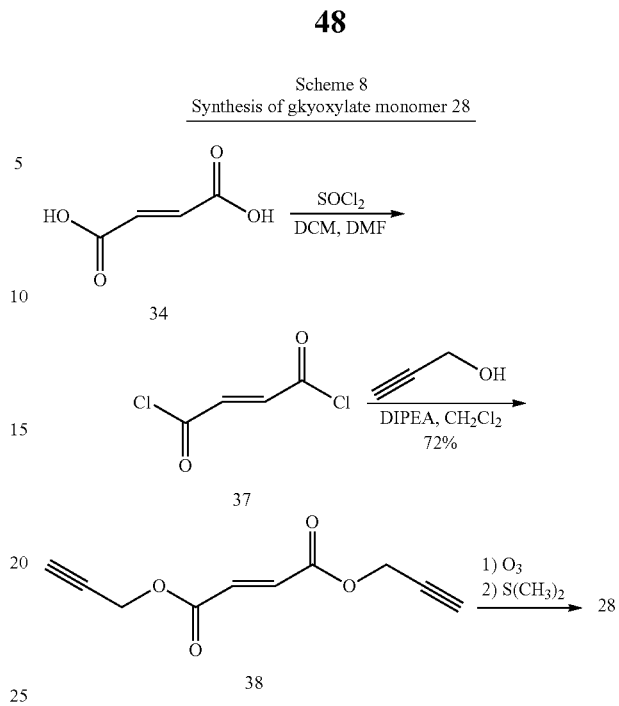

For example, as shown in Scheme 7, to prepare glyoxylate 30, fumaric acid (34) was esterified using ethylene glycol under acidic conditions to provide 35. The alcohol groups were then protected by reaction with tert-butyldimethylsilyl chloride (TBDMSCl) to provide 36. Ozonolysis afforded 30. As shown in Scheme 8, fumaric acid could alternatively be converted to the corresponding acid chloride (37)[30] and then reacted with propargyl alcohol to afford 38. Ozonolysis provided 28.

Two pharmaceutical targets, acetaminophen (31) and the ethyl ether of salicylic acid (32), marketed as Tylenol™ and Aspirin™ (the free acid), respectively, were also used to demonstrate feasibility. The glyoxylate monomers were prepared as described below in Scheme 9. Compound 37[30] was coupled to the phenol derivatives (38) and (39) to provide 40 and 41 respectively. Alternative preparations of 40 and 41 directly from fumaric acid were also investigated using agents such as 1,1'-carbonyldiimidazole (CDI), O-(6-Chlorobenzotriazol-1-yl)-N,N,N',N'-tetramethyluronium hexafluorophosphate (HCTU), and N-(3-Dimethylaminopropyl)-N'-ethylcarbodiimide hydrochloride (EDC-HCl), which are also capable of generating the dialkyl fumarates. Lower yields were obtained. Ozonoloysis of 40 and 41 provided glyoxylates 32 and 33 respectively. The resulting glyoxylates were then purified by high-vacuum distillation over $P_2O_5$.

Scheme 7
Synthesis of glyoxylate monomer 30

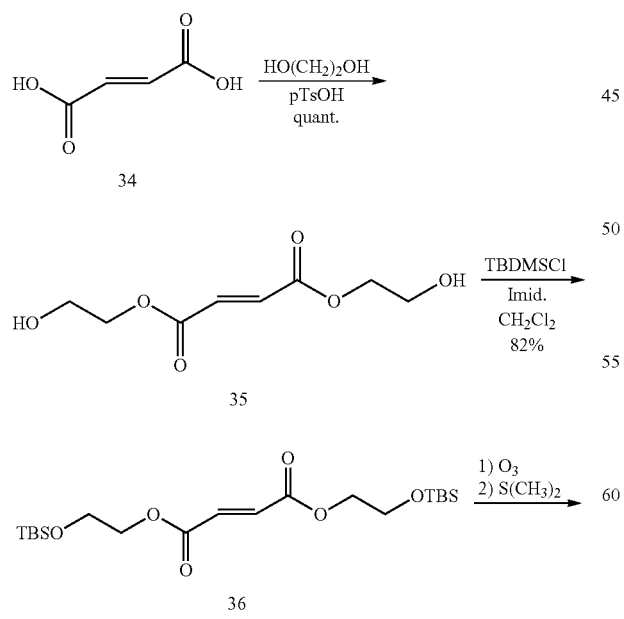

Scheme 9
Synthesis of glyoxylate monomers 31 and 32.

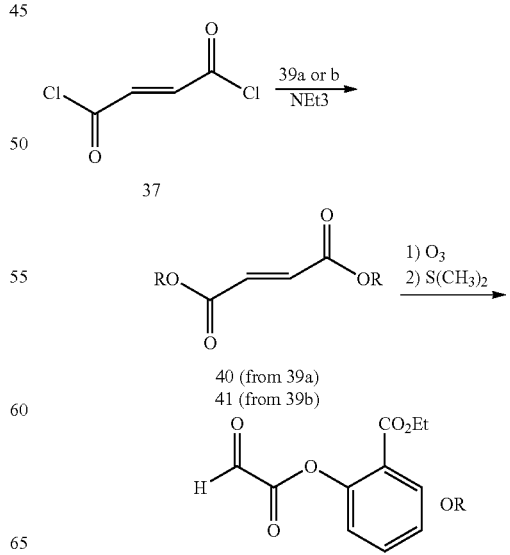

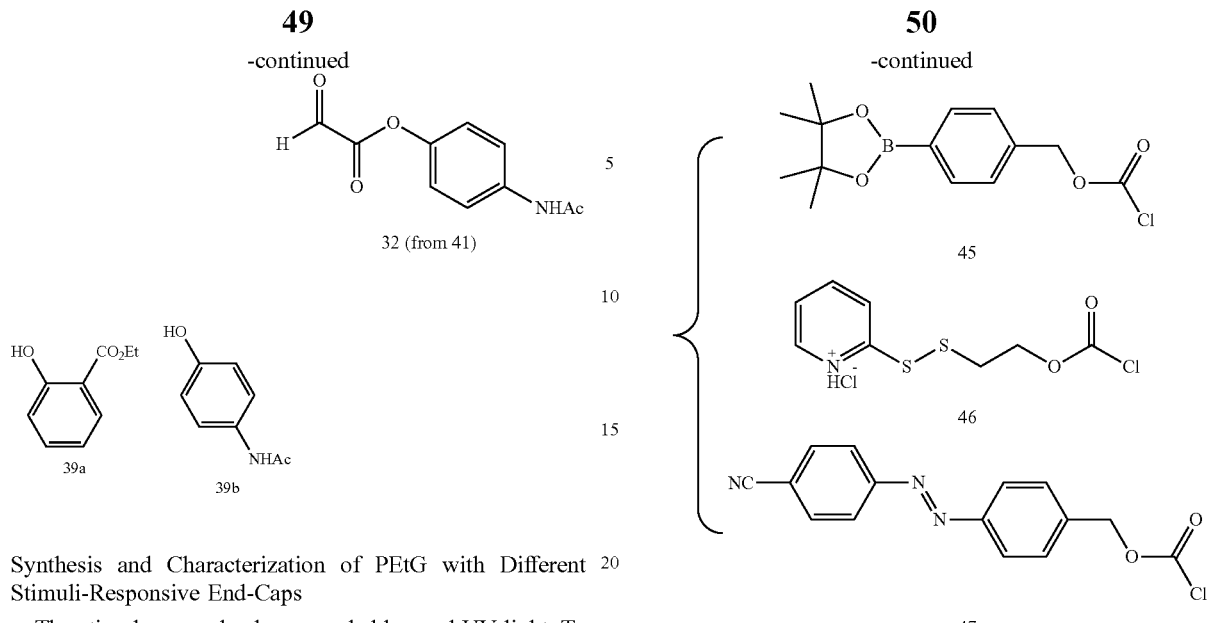

Synthesis and Characterization of PEtG with Different Stimuli-Responsive End-Caps The stimulus can also be expanded beyond UV light. To demonstrate this, several new end-caps were prepared. For example, as shown in the Scheme 10, the hydroxyl groups in compounds 42-44 were converted into chloroformates 45-47 by reaction with phosgene in more than 90% yield. The phenylboronic acid pinacol ester in chloroformate 45 can readily react with hydrogen peroxide or other oxidizing agents to provide a phenol, which can then initiate a 1,6-elimination to form a quinone methide, followed by the release of carbon dioxide. It was proposed that this process could initiate depolymerization as shown in Scheme 11a. In chloroformate 46, the disulfide linkage is sensitive to reducing conditions. With one equivalent of reductive agent, such as DTT, the disulfide linkage can be reduced and then the resulting thiol was proposed to undergo cyclization[41] to release the hemiacetal terminated polymer (Scheme 11b). Chloroformate 47 is an azo-compound, which was recently explored as a reductive sensitive end-cap by our group.[42] It can be reduced by reaction with either hydrazine or DTT to provide a secondary amine, which can lead to 1,6-elimination, followed by loss of $CO_2$ to initiate depolymerization (Scheme 11c).

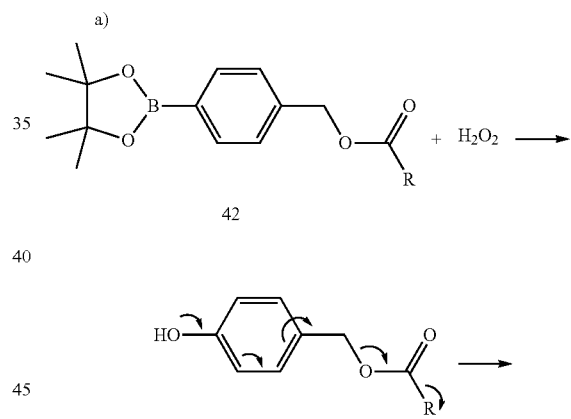

Scheme 10
Synthesis of chloroformate based end-caps.

Scheme 11
Triggering mechanism of different end-caps.
R⁻ = polyglyoxylate-O⁻ terminus

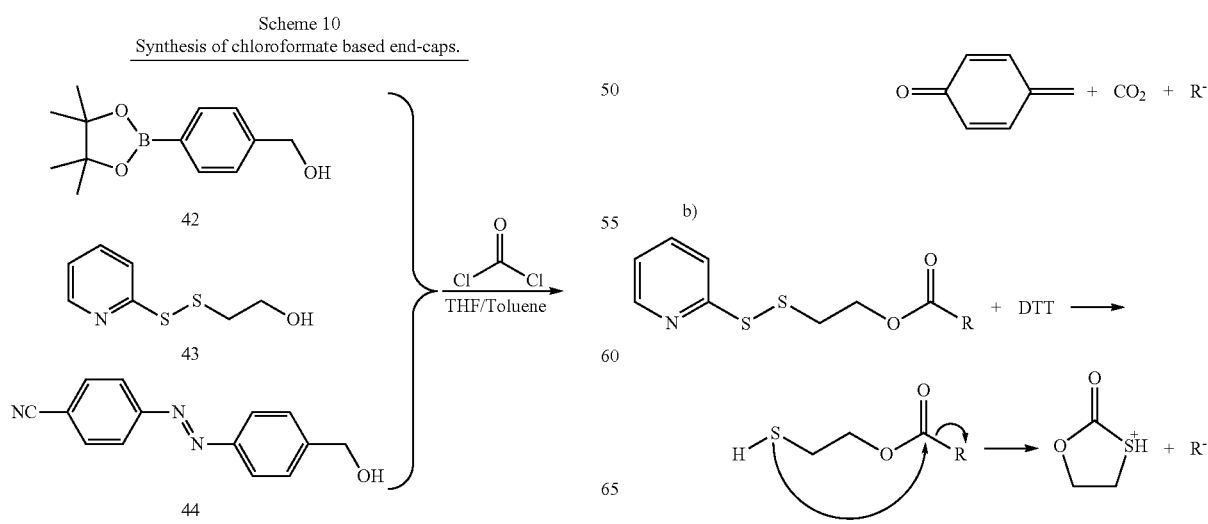

51

-continued c)

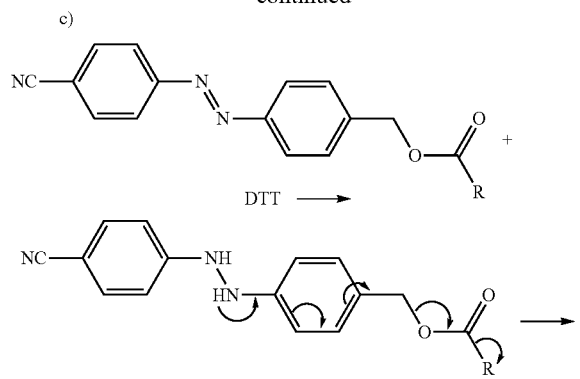

DTT ⟶

52

-continued

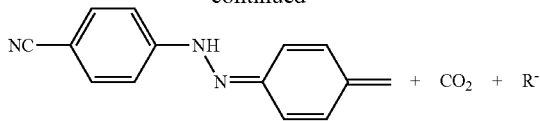

+ CO₂ + R⁻

With all of these chloroformate end-caps in hand, polymerization of ethyl glyoxylate was conducted via anionic polymerization at −20° C., then the polymer was end-capped in situ by reaction with chloroformates 45-47, to afford polymers 48-50 that are sensitive to oxidation, reduction and hydrazine respectively (Scheme 12). Characterization data for these polymers is given in Table 3.

Scheme 12
Synthesis of poly(ethyl glyoxylates) with different end-caps.

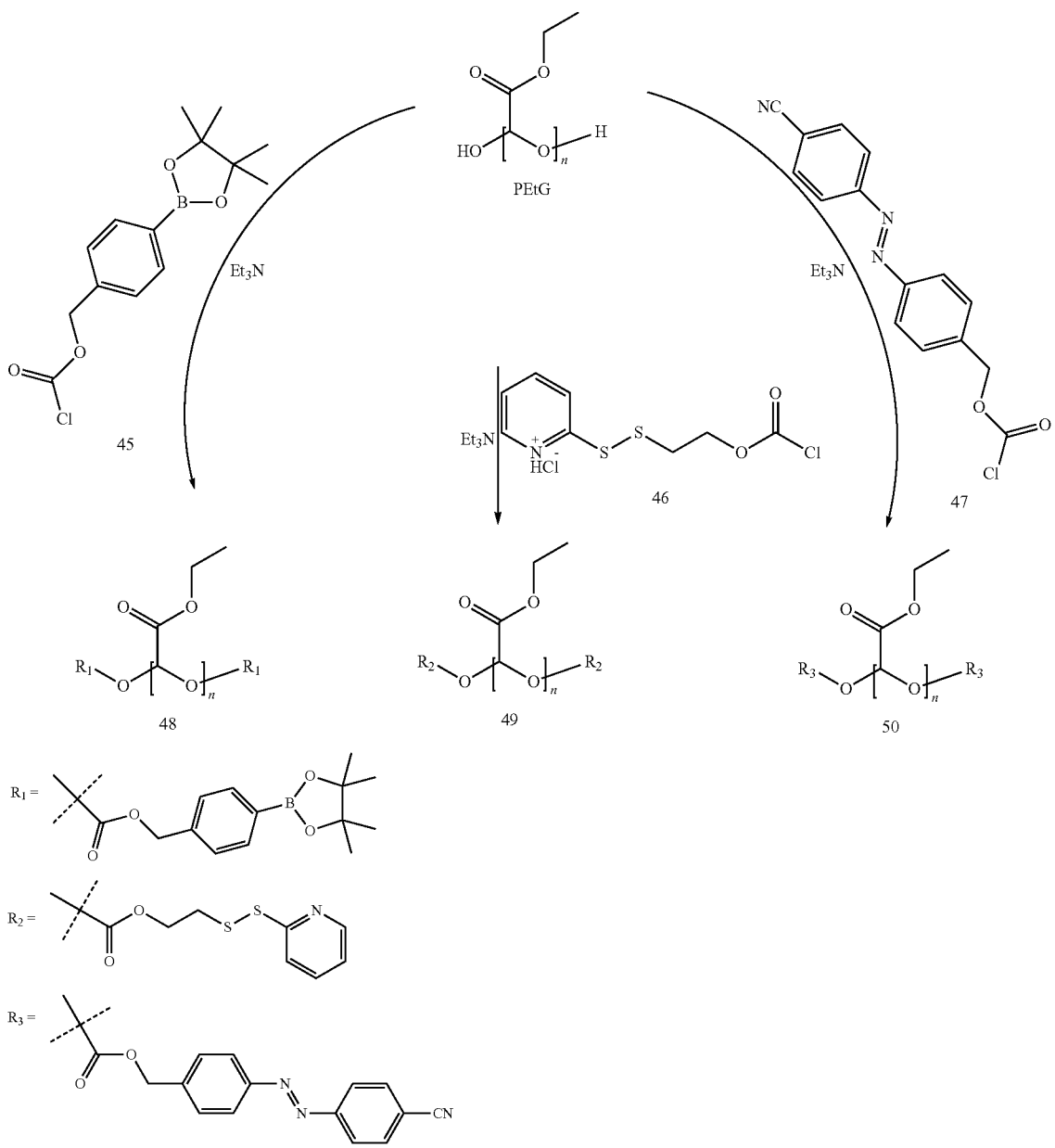

TABLE 3

Molecular weights, measured by SEC in THF, relative to PS standards for the polymers. Thermal properties of polyglyoxylates measured by TGA and DSC. $T_{98}$ = maximum temperature at which 98% of mass is still present, $T_g$ is the glass transition temperature.

| Polymer | $M_n$ (SEC) (kDa) | $M_w$ (SEC) (kDa) | Dispersity (Đ) | $T_{98\%}$ (° C.) | $T_g$ (° C.) |
|---|---|---|---|---|---|
| 48 | 131 | 305 | 2.3 | 193 | −1 |
| 49 | 250 | 425 | 1.7 | 151 | −7 |
| 50 | 246 | 461 | 1.9 | 108 | −7 |

Figure 23:
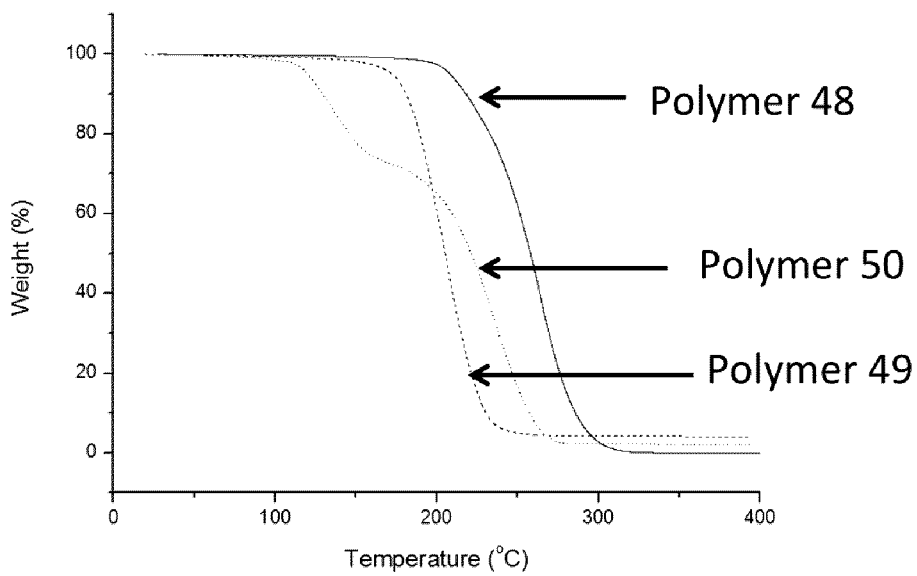
FIG. 23 shows thermal degradation of polymers 48-50.

As shown from the TGA results (Table 3 and FIG. 23), polymer 50 had a much lower $T_{98}$ compared to 48 and 49, and there were two stages on the TGA curve for polymer 50. This suggests that polymer 50 may not have been completely end-capped. One possibility is that polymers 50 had a much longer chain length compared to our previously reported examples. This may make end-capping more difficult. In addition, with higher molecular weight the polymer can precipitate in methanol more rapidly, so there is less chance to selectively remove unend-capped polymers during this purification procedure. However, the TGA results indicate that there was at least 70% of polymer 50 properly end-capped, which was sufficient for depolymerization studies. Although polymer 49 had a relatively lower $T_{98}$ compared to polymer 48 and previous samples, no two-phase degradation was observed, so the polymer was deemed to be well end-capped. The lower $T_{98}$ likely results from the limited thermal stability of the disulfide linkage in the end-cap above 150° C.

Figure 24:
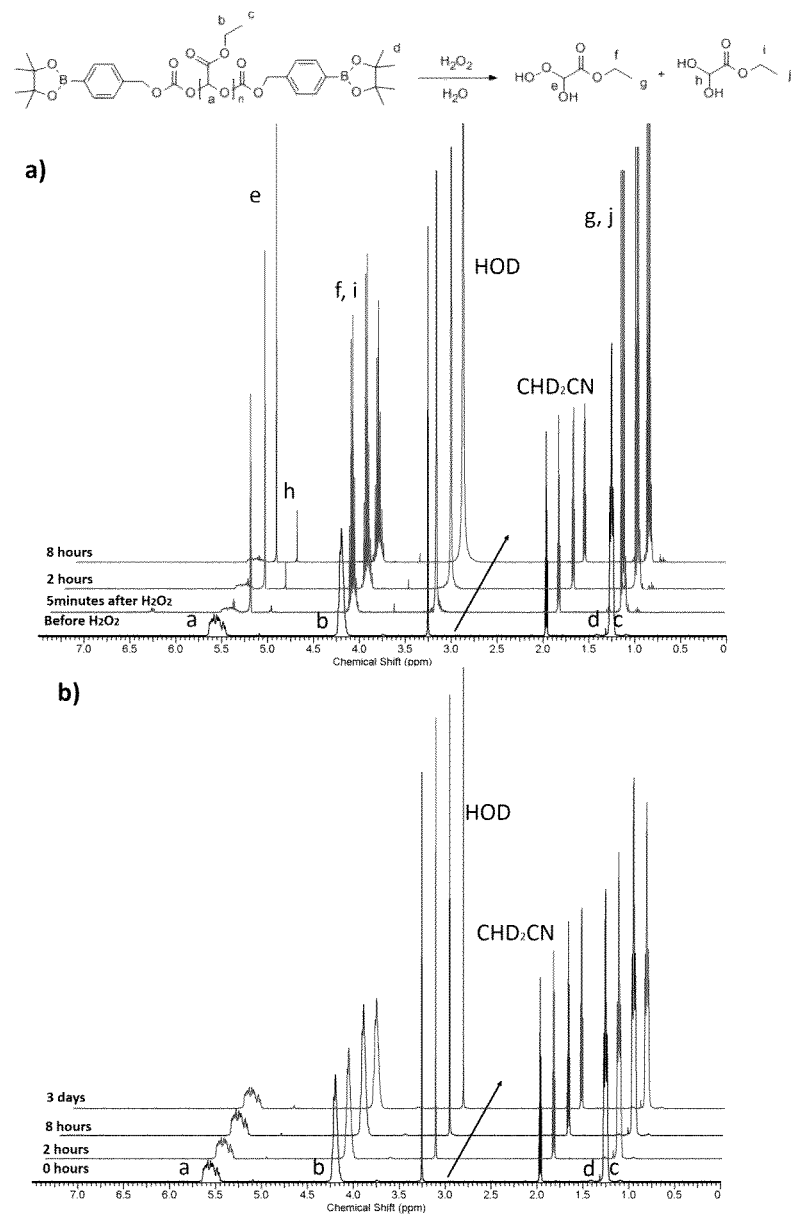
FIG. 24 shows $^1$H NMR spectra of polymer 48 dissolved in 9:1 $CD_3CN:D_2O$ a) with and b) without addition of $H_2O_2$. This shows that the polymer degrades selectively in the presence of $H_2O_2$.
Figure 25:
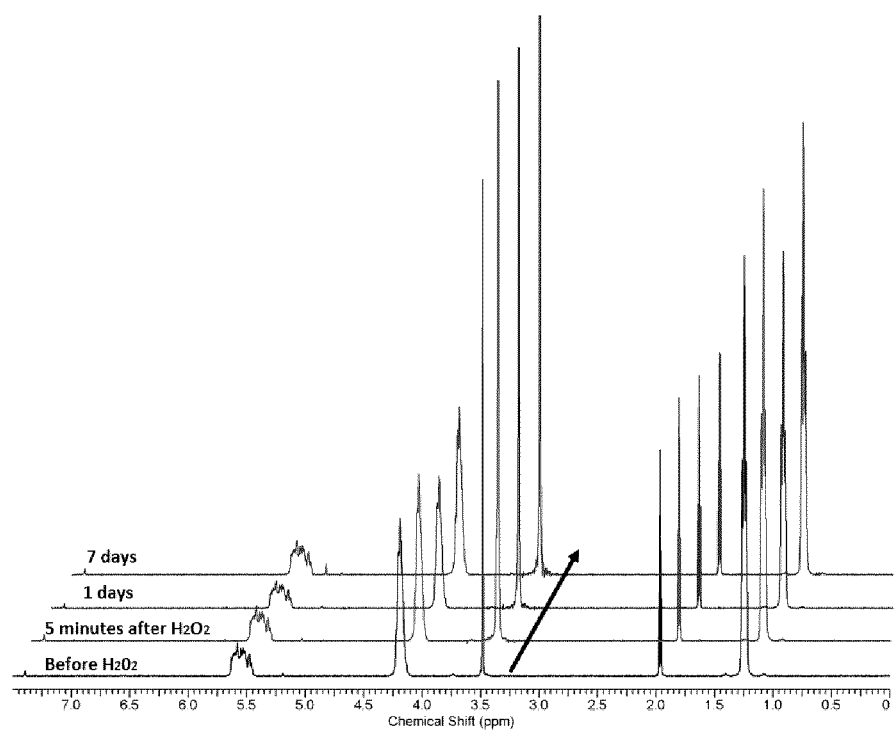
FIG. 25 shows $^1$H NMR spectra of polymer 3 dissolved in 9:1 $CD_3CN:D_2O$ with addition of $H_2O_2$. No changes were observed, indicating that the polymer is stable under these conditions and $H_2O_2$ does not cleave the polymer backbone.

The degradation of these polymers was studied in the presence and absence of the stimuli. The triggered degradation of PEtG 48 in response to $H_2O_2$ was studied in solution first. Polymer 48 was dissolved in 9:1 $CD_3CN:D_2O$ at 15 mg/mL, a concentration sufficient for NMR studies. A comparison of the NMR spectra with and without addition of $H_2O_2$ (132 mM) supports the successful cleavage of the end-cap by $H_2O_2$ (FIG. 24a). Before addition of $H_2O_2$, the spectrum consisted of three broad peaks attributable to the PEtG backbone. Because of the extremely high molecular weight of this batch of polymer, the end-caps could not be detected from the NMR spectroscopy. However, following the addition of $H_2O_2$, the broad peak at 5.5 ppm corresponding to the acetal hydrogens along the polymer backbone decreased in intensity while two new sharp peaks at 5.3 ppm and 5.1 ppm emerged. The sharp peak at 5.1 ppm can be assigned to the degradation product EtGH as observed in previous examples. The new peak at 5.3 ppm can likely be attributed to a reaction product of ethyl glyoxylate with $H_2O_2$ due to the increased nucleophilicity of $H_2O_2$ compared to water. At the same time, sharpening of the peaks corresponding to the ethyl group were also consistent with depolymerization to small molecules. Based on the relative peak integrations, about 70% of the PEtG had depolymerized into small molecules just after the addition of $H_2O_2$. In contrast, as shown in FIG. 24b, PEtG 48 without the addition of $H_2O_2$ only showed less than 3% degradation after 3 days in solution. In addition, PEtG 3 with the benzyl carbonate end-cap remained unchanged with same amount of $H_2O_2$ after 7 days in solution (FIG. 25). Combined, these data confirm that the depolymerization of PEtG 48 indeed resulted from backbone depolymerization induced by end-cap cleavage and not by random backbone cleavage induced by $H_2O_2$ or hydrolytic reactions.

Figure 26:
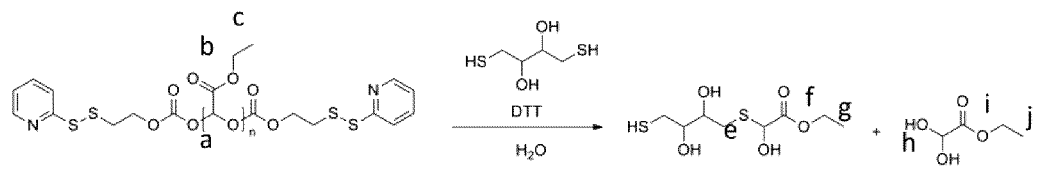
FIG. 26 shows $^1$H NMR spectra of polymer 49 dissolved in 9:1 $CD_3CN:D_2O$ a) with and b) without addition of dithiothreitol (DTT). This shows that the polymer degrades selectively in the presence of DTT.
Figure 26:
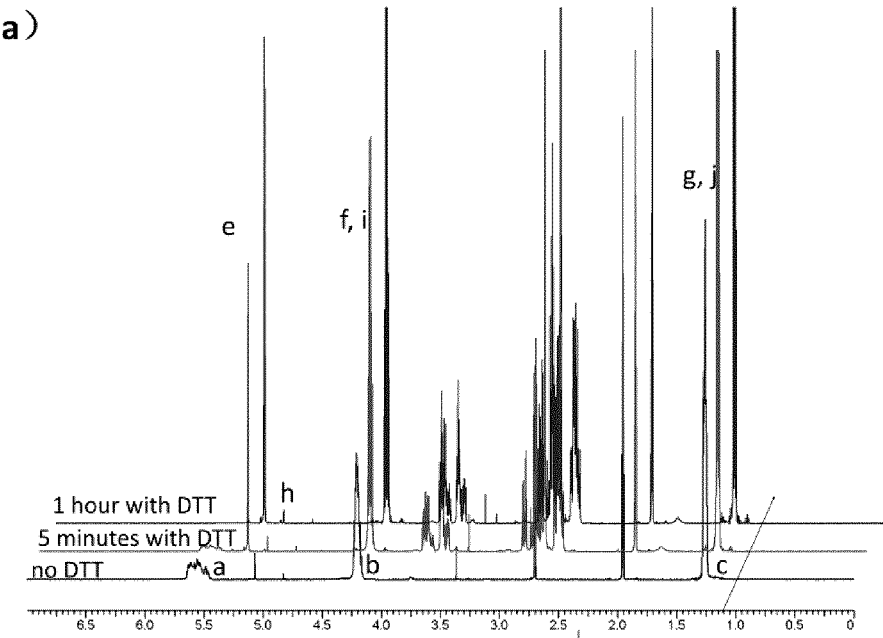
Figure 26:
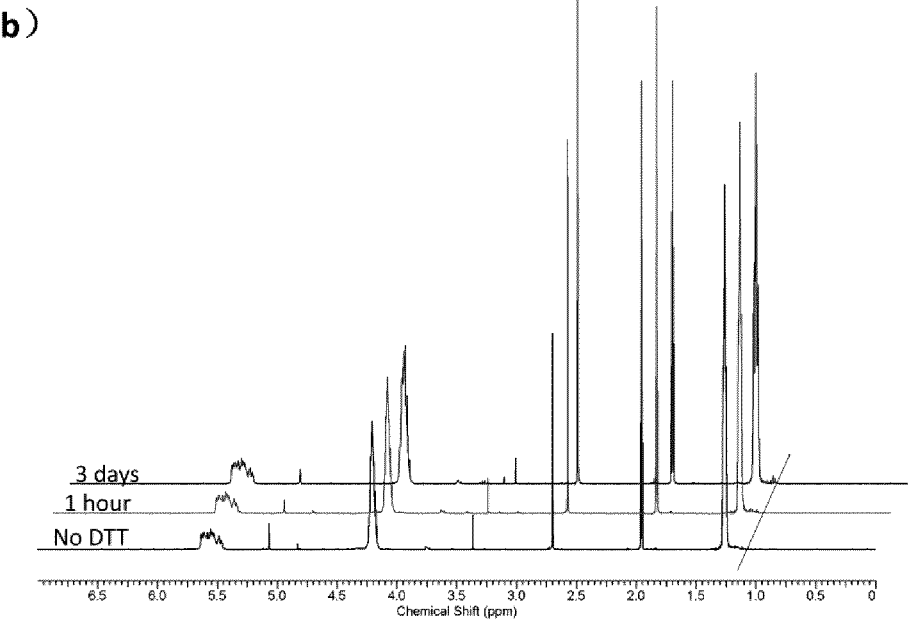
Figure 27:
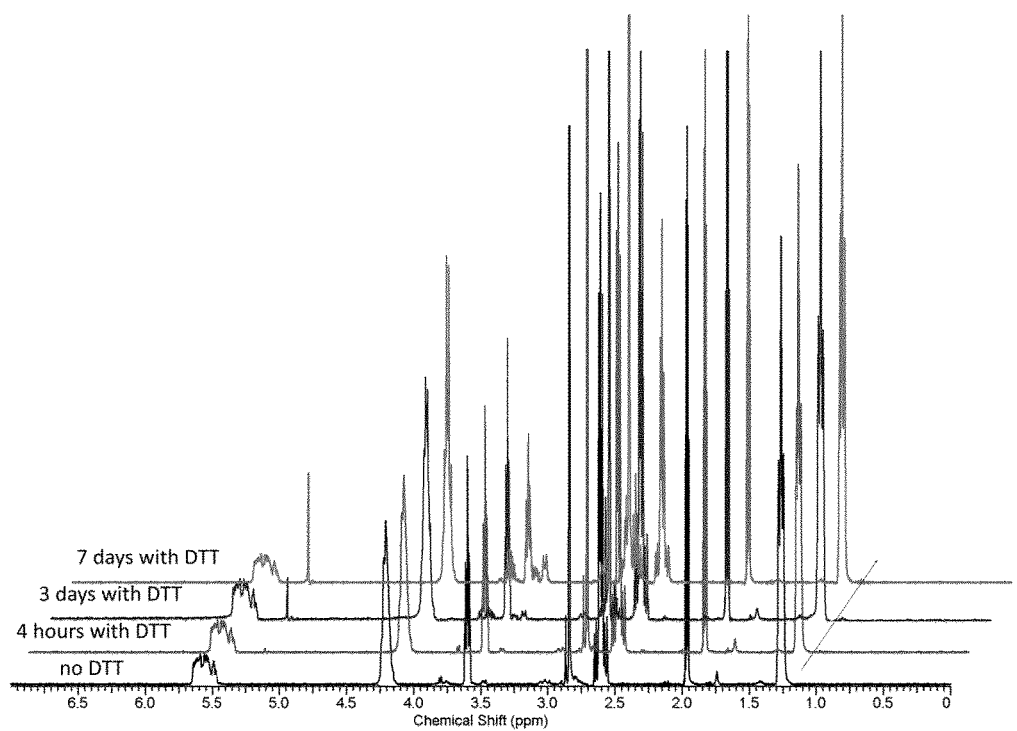
FIG. 27 shows $^1$H NMR spectra of polymer 3 dissolved in 9:1 $CD_3CN:D_2O$ with addition of DTT. Only very gradual changes were observed, indicating that the polymer is quite stable under these conditions and DTT does not significantly cleave the polymer backbone.

An NMR degradation study was also conducted with polymer 49 as well. In this case, because the polymer was functionalized with a reduction-responsive end-cap, dithiothreitol (DTT), which is a common reducing agent to reduce the disulfide bonds of proteins, was chosen as the trigger for depolymerization. However, because DTT is also a very strong nucleophile, it can react very rapidly with depolymerized monomers compared to water molecules. Therefore, in order to ensure that there was enough DTT to break down the end-caps, excess DTT (110 mM) was added into the NMR tube. As shown in FIG. 26a, ~50% of the polymer degraded immediately after addition of DTT, and after 1 hour 97% polymer was degraded. In contrast, the control sample of polymer 49 without DTT underwent only ~5% degradation after 3 days (FIG. 26b). The benzyl chloroformate end-capped control polymer 3, underwent only about 4% and 5% degradation after 4 hours and 1 day, respectively, even with same amount of DTT (FIG. 27). Combined, these data suggest that the polymer was at least 95% end-capped, and that addition of the reducing agent DTT selectively triggered rapid depolymerization.

Figure 28:
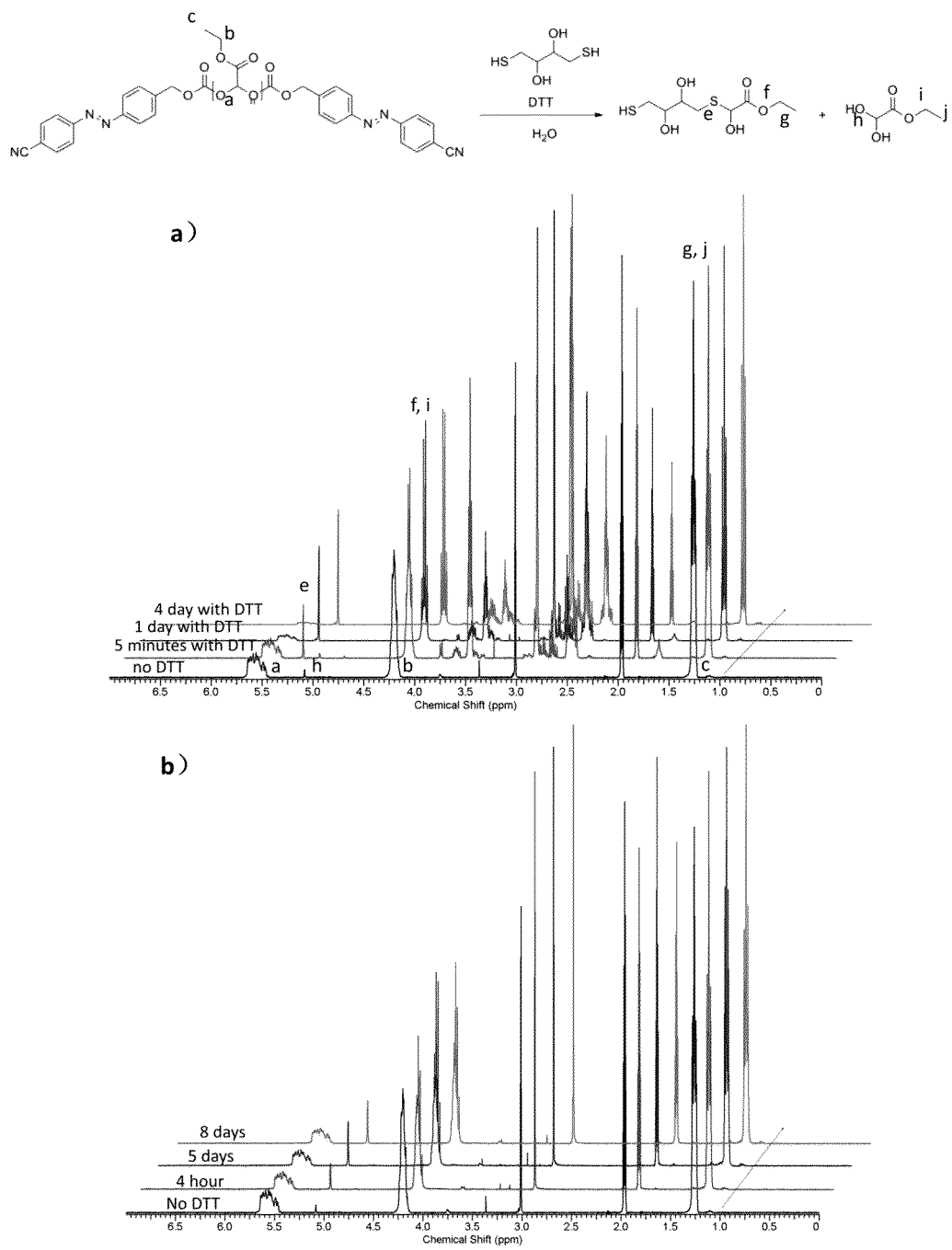
FIG. 28 shows $^1$H NMR spectra of polymer 50 dissolved in 9:1 $CD_3CN:D_2O$ a) with and b) without addition of DTT. This shows that the polymer degrades selectively in the presence of DTT. The small extent (~20%) of depolymerization that occurred in the absence of DTT can be attributed to a fraction of uncapped polymer as revealed by the TGA results in FIG. 23.

Lastly, the degradation profile of polymer 50 was investigated. This end-cap should be easily cleaved by hydrazine, making polymer 50 sensitive to hydrazine. When hydrazine (100 mM) was added into polymer 50 solution, the polymer did degrade immediately. Unfortunately, the control polymer 3 that was end-capped by benzyl chloroformate degraded as well, suggesting that hydrazine can generally cleave carbonates under these conditions and therefore the trigger was not very specific. As demonstrated by our group[42], the azo-compound can also be reduced by DTT, albeit with slower rate. Therefore, polymer 50 was also subjected to DTT as the trigger for depolymerization. As shown from FIG. 28a, approximately 50% of the polymer degraded after 1 day with addition of DTT (110 mM). This rate is much slower compared to polymer 49, which underwent 97% degradation in just 1 hour. The degradation finally plateaued at the fourth day with 75% depolymerization, likely because of the consumption or background oxidation of DTT. As shown from FIG. 28b, approximately 20% of polymer 50 depolymerized in the absence of DTT, consistent with the incomplete end-capping observed by TGA. In addition, at the concentrations of DTT employed in this study, about 14% of control polymer 3 depolymerized over the time period of this experiment. It can still be concluded that polymer 50 undergoes depolymerization in response to reducing agents. The slower response to DTT in the case of this polymer relative to polymer 49 might be useful for some applications.

Responsiveness to stimuli other than light can also be imparted into block copolymers using a new and versatile end-cap design. Compound 51 incorporates an alkyne for conjugation to another polymer block, a benzylic alcohol for activation to a chloroformate, and an aniline in an ortho position to the benzylic alcohol. Scheme 13 shows how this is a general design for incorporating moieties responsive to different stimuli, which allows stimulus-mediated cleavage to be relayed to the polyglyoxylate block. As an example, this was demonstrated for the oxidation-sensitive borate. Firstly, the nitro group in compound 17 was reduced to an amine group, providing 51, which was further reacted with chloroformate 45 to afford compound 52. The hydroxyl group of compound 52 was then converted into chloroformate 53 by reaction with phosgene. Because of the presence of the phenylboronic acid pinacol ester group, which can be easily removed by hydrogen peroxide or other oxidizing agents, once introduced onto the polymer, end-cap 53 will not only be able to couple PEtG with another polymer block such as PEG-N$_3$, but it can also impart cleavage and thus depolymerization via two sequential 1,6-elimination and decarboxylation reactions in the presence of the stimulus such as H$_2$O$_2$. With chloroformate 53 in hand, the polymerization of ethyl glyoxylate was conducted and in situ end-capped by chloroformate 53 to afford polymer 54. Polymer 54 was then coupled with PEG-N$_3$ to provide a triblock copolymer 55 that is responsive to oxidizing conditions (Scheme 14). Using an analogous strategy, it should be possible to use this multifunctional molecule 51 to introduce different stimuli-responsive groups (e.g., chloroformates 56-57), thereby providing a versatile stimuli-responsive linker for polyglyoxylates.

Scheme 13
Synthesis of oxidation-responsive linker 49 and its proposed degradation in response to H$_2$O$_2$ as an oxidizing agent.

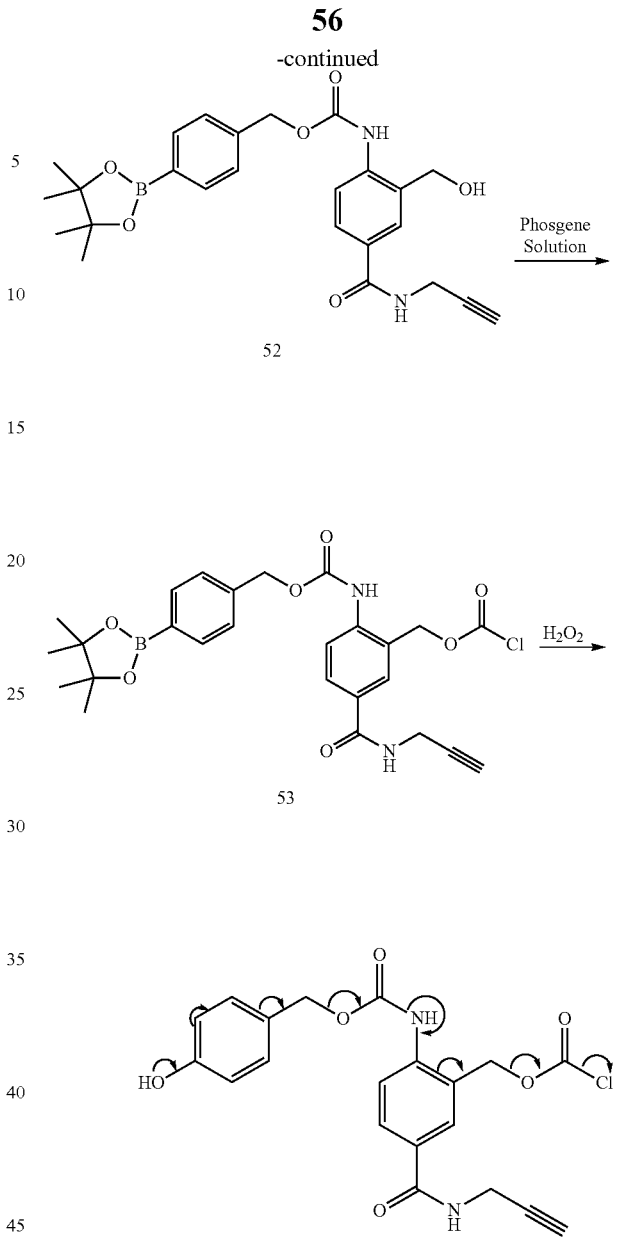

SCHEME 14
Synthesis of an oxidation-responsive block copolymer 55

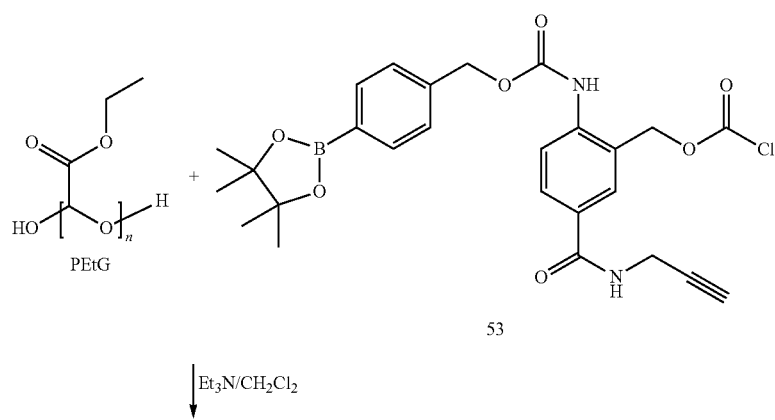

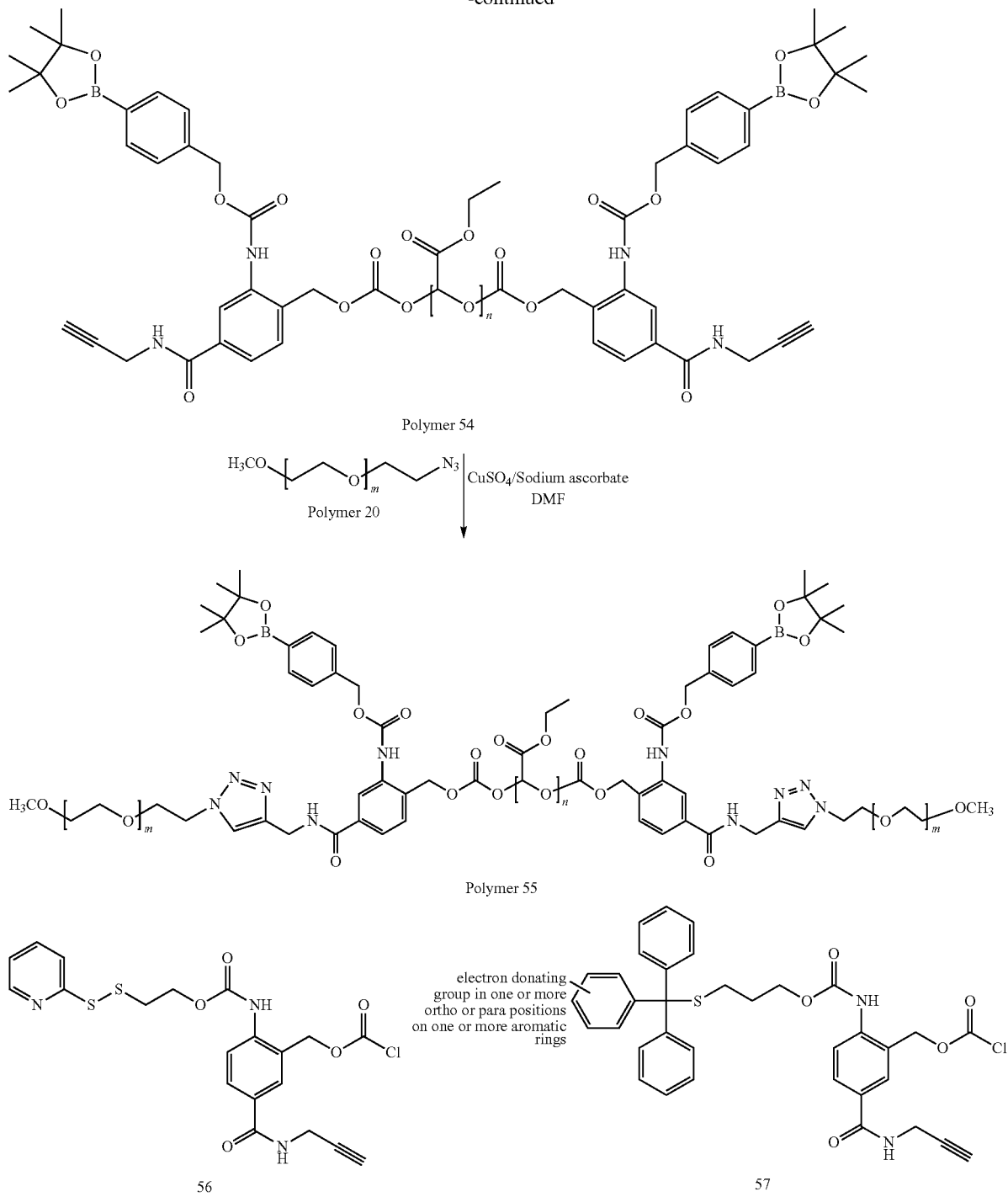

REFERENCES

1. Ulery, B. D.; Nair, L. S.; Laurencin, C. T., Biomedical applications of biodegradable polymers. *Journal of Polymer Science Part B: Polymer Physics* 2011, 49(12), 832-864.
2. Luckachan, G. E.; Pillai, C. K. S. Biodegradable polymers—a review on recent trends and emerging perspectives. *Journal of Polymers and the Environment* 2011, 19(3), 637-676.
3. Tschan, M. J.-L.; Brule, E.; Haquette, P.; Thomas, C. M., Synthesis of biodegradable polymers from renewable resources. *Polymer Chemistry* 2012, 3(4), 836-851.
4. Gandini, A., The irruption of polymers from renewable resources on the scene of macromolecular science and technology. *Green Chemistry* 2011, 13(5), 1061-1083.
5. Kim, J.-K.; Garripelli, V. K.; Jeong, U.-H.; Park, J.-S.; Repka, M. A.; Jo, S., Novel pH-sensitive polyacetal-based block copolymers for controlled drug delivery. *International Journal of Pharmaceutics* 2010, 401 (1), 79-86.

6. Meester, W. J. N.; Maarseveen, J. H. V.; Schoemaker, H. E.; Hiemstra, H.; Rutjes, F. P. J. T., Glyoxylates as Versatile Building Blocks for the Synthesis of α-Amino Acid and α-Alkoxy Acid Derivatives via Cationic Intermediates. *European Journal of Organic Chemistry* 2003, 2003 (14), 2519-2529.
7. McFadden, B. A.; Howes, W. V., The determination of glyoxylic acid in biological systems. *Analytical Biochemistry* 1960, 1 (3), 240-248.
8. Crutchfield M. M.; Papanu V. D.; Warren C. B. U.S. patent application Ser. No. 05/826,425, 1977.
9. Crutchfield M. M.; Papanu V. D.; Warren C. B. U.S. patent application Ser. No. 05/962,512, 1978.
10. Dyroff, D. R.; Lynch, G. J.; Papanu, V. D. U.S. patent application Ser. No. 06/091,656, 1979.
11. Brachais, C. H.; Huguet, J.; Bunel, C., Synthesis, characterization and stabilization of poly(methyl glyoxylate). *Polymer* 1997, 38 (19), 4959-4964.
12. Brachais, L.; Brachais, C.-H.; Huguet, J.; Bunel, C., Identification of small molecules formed from polymethyl glyoxylate degradation in vitro. *Polymer Degradation and Stability* 1999, 64 (2), 6.
13. Brachais; C. H.; Huguet; J.; Bunel; C.; Brachais, L., In vitro degradation of poly(methyl glyoxylate) in water. *Polymer* 1998, 39 (04), 7.
14. Burel, F.; Rossignol, L.; Pontvianne, P.; Hartman, J.; Couesnon, N.; Bunel, C., Synthesis and characterization of poly(ethyl glyoxylate)—a new potentially biodegradable polymer. *e-Polymers*, 2003, 3, 407.
15. Belloncle, B.; Bunel, C.; Menu-Bouaouiche, L.; Lesouhaitier, O.; Burel, F., Study of the Degradation of Poly (ethyl glyoxylate): Biodegradation, Toxicity and Ecotoxicity Assays. *Journal of Polymers and the Environment* 2012, 20 (3), 726-731.
16. Belloncle, B.; Burel, F.; Bunel, C., Synthesis and (bio) degradation of poly (ethyl glyoxylate). *Polymer Preprints* 2007, 48 (1), 633-634.
17. B. Belloncle; F. Burel; H. Oulyadi; Bunel, C., Study of the in vitro degradation of poly(ethyl glyoxylate). *Polymer Degradation and Stability* 2008, 93 (9), 6.
18. Wong, A. D.; DeWit, M. A.; Gillies, E. R., Amplified release through the stimulus triggered degradation of self-immolative oligomers, dendrimers, and linear polymers. *Advanced Drug Delivery Reviews* 2012, 64 (11), 1031-1045.
19. Peterson, G. I.; Larsen, M. B.; Boydston, A. J., Controlled Depolymerization: Stimuli-Responsive Self-Immolative Polymers, *Macromolecules* 2012, 45, 7317-7328.
20. Phillips, S. T.; DiLauro, A. M., Continuous head-to-tail depolymerization: An emerging concept for imparting amplified responses to stimuli-responsive materials. *ACS Macro Letters* 2014, 3, 298-304.
21. Liu, F.; Urban, M. W., Recent advances and challenges in designing stimuli-responsive polymers. *Progress in Polymer Science* 2010, 35, 3.
22. Schattling, P.; Jochum, F. D.; Theato, P., Multi-stimuli responsive polymers—the all-in-one talents. *Polymer Chemistry* 2014, 5, 25.
23. Cohen Stuart, M.; Huck, W. T. S.; Genzer, J.; Muller, M.; Ober, C.; Stamm, M.; Sukhorukov, G. B.; Szieifer, I.; Trukruk, V. V.; Urban, M.; Winnik, F.; Zauscher, S.; Luzinov, I.; Minko, S., Emerging applications of stimuli-responsive polymer materials. *Nature Materials* 2010, 9, 101.
24. H. Kimura, A simple method for the anionic polymerization of α-carbonyl acids in water. *Journal of Polymer Science Part A: Polymer Chemistry* 1998, 36 (1), 189-193
25. Dawar, P.; Bhagavan Raju, M.; Ramakrishna, R. A., One-pot esterification and Ritter reaction: chemo- and regioselectivity from tert-butyl methyl ether. *Tetrahedron Letters* 2011, 52 (33), 4262-4265.
26. Choi, T.-L.; Lee, C. W.; Chatterjee, A. K.; Grubbs, R. H., Olefin Metathesis Involving Ruthenium Enoic Carbene Complexes. *Journal of the American Chemical Society* 2001, 123 (42), 10417-10418.
27. Chan, T. M.; Jianshe, K.; McNamara, P.; Wong, J. K., Syntheses of Potential Degradation Products of Phenylephrine in OTC Products. *Synthetic Communications* 2008, 38 (13), 2252-2260.
28. Donohoe, T. J.; Fishlock, L. P.; Procopiou, P. A., A Metathesis-Based Approach to the Synthesis of 2-Pyridones and Pyridines. *Organic Letters* 2007, 10 (2), 285-288.
29. Bishop, J. E.; OConnell, J. F.; Rapoport, H., The Reaction of Thioimides with Phosphorus Ylides. *Journal of Organic Chemistry* 1991, 56 (17), 5079-5091.
30. Das, S.; Das, U.; Varela-Ramirez, A.; Lema, C.; Aguilera, R. J.; Balzarini, J.; De, C. E.; Dimmock, S. G.; Gorecki, D. K. J.; Dimmock, J. R., bis[3,5-bis(Benzylidene)-4-oxo-1-piperidinyl]amides: A novel class of potent cytotoxins. *Chem Med Chem* 2011, 6, 1892.
31. Shi, G.-Y.; Pan, C.-Y., Synthesis of Well-Defined Figure-of-Eight-Shaped Polymers by a Combination of ATRP and Click Chemistry. *Macromolecular Rapid Communications* 2008, 29, 1672.
32. Eisenfuhr, A.; Arora, P. S.; Sengle, G.; Takaoka, L. R.; Nowick, J. S.; Famulok, M., A Ribozyme with Michaelase Activity: Synthesis of the Substrate Precursors. *Bioorganic & Medicinal Chemistry* 2003, 11 (2), 235-249.
33. Chung, C.; Srikun, D.; Lim, C. S.; Chang, C. J.; Cho, B. R., A two-photon fluorescent probe for ratiometric imaging of hydrogen peroxide in live tissue. *Chemical Communications* 2011, 47, 9618.
34. Jia, L.; Cui, D.; Bignon, J.; Cicco, A. D.; Wdzieczak-Bakala, J.; Liu, J.; Li, M. H., Reduction-Responsive Cholesterol-Based Block Copolymer Vesicles for Drug Delivery. *Biomacromolecules* 2014, 15, 2206.
35. Valley, D. T.; Onstott, M.; Malyk, S.; Benderskii, A. V., Steric Hindrance of Photoswitching in Self-Assembled Monolayers of Azobenzene and Alkane Thiols. *Langmuir* 2013, 29, 11623.
36. (a) Wolf, F. J.; Weijlard, J., n-Butyl glyoxylate. *Organic Syntheses* 1955, 35, 18; (b) Kelly, T. R.; Schmidt, T. E.; Haggerty, J. G., A Convenient Preparation of Methyl and Ethyl Glyoxylate. *Synthesis* 1972, 1972 (10), 544-545; (c) Hook, J. M., A Simple and Efficient Synthesis of Ethyl and Methyl Glyoxylate. *Synthetic Communications* 1984, 14 (1), 83-87
37. Mahou, R.; Wandrey, C., Versatile Route to Synthesize Heterobifunctional Poly(ethylene glycol) of Variable Functionality for Subsequent Pegylation. *Polymer* 2012, 4010 (4), 561-589.
38. Discher, D. E.; Eisenberg, A., Science 2002, 297, 967-973.
39. Krishna, M. M. G. Excited state kinetics of the hydrophobic probe nile red in membranes and micelles. *Journal of Physical Chemistry A,* 1999, 103, 3589-3595.
40. Tian, Z.; Liu, X.; Chen, C.; Allcock, H. R., Synthesis and Micellar Behavior of Novel Amphiphilic Poly [bis (trifluoroethoxy) phosphazene]-co-poly [(dimethylamino) ethyl methacrylate] Block Copolymers. *Macromolecules* 2012, 45 (5), 2502-2508.

41. Chen, E. K. Y.; McBride, R. A.; Gillies, E. R., Self-Immolative Polymers Containing Rapidly Cyclizing Spacers: Toward Rapid Depolymerization Rates. *Macromolecules* 2012, 45, 7364-7374.

42. Wong, A. D.; Güngör, T. M.; Gillies, E. R., Multiresponsive Azobenzene End-cap for Self-immolative Polymers. *ACS Macro Letters* 2014, 3, 1191-1195.

The invention claimed is:

1. A capped polymer comprising a polyglyoxylate polymer having a polyacetal backbone with pendant esters and a terminal hydroxyl, an end capping molecule separate from the polymer that is a protecting group for the polyglyoxylate's terminal hydroxyl or a self-immolative spacer covalently linked to the protecting group, which is linked to an end thereof by a covalent linkage, wherein the end capping molecule is able to undergo selective cleavage from the polyglyoxylate polymer upon exposure to a preselected stimulus, wherein said selective cleavage is cleavage only of said covalent linkage of the end capping molecule to the end of the polymer thus leaving the polyacetal backbone and the pendant esters intact to produce the polyglyoxylate polymer without the end capping molecule.

2. The capped polymer of claim 1, wherein the preselected stimulus is one or more of an aqueous solution, an enzyme, a reducing agent, an oxidizing agent, heat, and light.

3. The capped polymer of claim 2, wherein the aqueous solution has a pH of between about 2 and 9.

4. The capped polymer of claim 2, wherein the enzyme is selected from the group consisting of catalytic antibodies, esterases, and peptidases.

5. The capped polymer of claim 2, wherein the reducing agent is a thiol, particularly glutathione.

6. The capped polymer of claim 2, wherein the oxidizing agent is hydrogen peroxide.

7. The capped polymer of claim 1, wherein the polyglyoxylate polymer has an average molecular weight in the range from 1000 Da to $10^6$ Da based on polystyrene standards.

8. The capped polymer of claim 1, wherein the polyglyoxylate polymer has a polydispersity index in the range from 1.0 to 3.0.

9. The capped polymer of claim 1, wherein the polymer has the structure of formula (A):

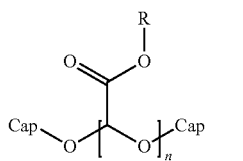

(A)

wherein n is between 10 and 2,000, R is selected from the group consisting of:
(i) H,
(ii) optionally substituted $C_{1-20}$ linear or branched alkyl,
(iii) optionally substituted $C_{3-20}$ cycloalkyl,
(iv) optionally substituted $C_{2-20}$ linear or branched alkenyl,
(v) optionally substituted $C_{5-20}$ cycloalkenyl (vi) optionally substituted $C_{2-20}$ linear or branched alkynyl,
(vii) optionally substituted $C_{6-20}$ aromatic,
(viii) optionally substituted $C_{4-20}$ heteroaryl,
(ix) optionally substituted $C_{7-20}$ arylalkyl,
(x) optionally substituted $C_{2-20}$ cycloheteroalkyl,
(xi) cinnamoyl,
(xii) acrylyl,
(xiii) methacrylyl, and
(xiv) —$CH_2CH_2OSi(R^i)(R^{ii})(R^{iii})$ wherein:
each of $R^i$, $R^{ii}$ and $R^{iii}$ is, independently of the other, selected from foregoing groups (i) to (x) and at least one of $R^i$, $R^{ii}$ and $R^{iii}$ is selected from foregoing groups (ii) to (x), and
salts of any of the foregoing; and
-Cap represents the end capping molecule covalently linked to the polymer having the polyacetal backbone.

10. The capped polymer of claim 9, wherein -Cap represents the end capping molecule having the following formula

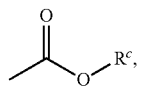

wherein $R^C$ is a group that is cleaved in response to a stimulus such as light, enzymes, heat, change in pH or redox potential.

11. The capped polymer of claim 9, wherein a said optional substituent is 1, 2, 3, 4 or 5 independent substitution(s) of a hydrogen atom(s), substituent(s) being selected independently from the following:

$C_{1-20}$ alkoxy,
$C_{2-20}$ alkenyloxy,
$C_{7-20}$ aryloxy,
$C_{7-20}$ cycloalkyloxy,
halogen (F, Cl, Br, I),
—OH,
—OC(O)CH=$CH_2$ (acrylyl), —OC(O)CCH$_3$=$CH_2$ (methacrylyl),
$NH_2$,
$N_3$ (azido), and
—C(O)$R^1$, —C(O)O$R^1$, —OC(O)$R^1$, NH$R^1$, N$R^1R^2$, wherein each $R^1$ and $R^2$ is independently selected from the group consisting of:
$C_{1-20}$ linear or branched alkyl, $C_{3-20}$ cycloalkyl, $C_{2-20}$ linear alkenyl, $C_{4-20}$ branched alkenyl, $C_{5-20}$ cycloalkenyl, $C_{2-20}$ linear alkynyl, $C_{5-20}$ branched alkynyl, $C_{6-20}$ aromatic, $C_{7-20}$ alkyl-substituted aromatic, $C_{7-20}$ aryl-substituted alkyl, epoxy, mercapto (—SH), NH$R^3$, N$R^3R^4$, wherein each each $R^3$ and $R^4$ is independently selected from the group consisting of $C_{1-20}$ linear alkyl, $C_{1-20}$ branched alkyl, $C_{3-20}$ cyclic alkyl, $C_{2-20}$ linear alkenyl, $C_{4-20}$ branched alkenyl, $C_{5-20}$ cyclic alkenyl, $C_{2-20}$ linear alkynyl, $C_{5-20}$ branched alkynyl, $C_{6-20}$ aromatic, $C_{7-20}$ alkyl-substituted aromatic, and $C_{7-20}$ aryl-substituted alkyl;
—C(O)O$R^5$ wherein each $R^5$ is independently selected from the group consisting of:
$C_{1-20}$ linear alkyl, $C_{1-20}$ branched alkyl, $C_{3-20}$ cycloalkyl, $C_{2-20}$ linear alkenyl, $C_{4-20}$ branched alkenyl, $C_{5-20}$ cycloalkenyl, $C_{2-20}$ linear alkynyl, $C_{5-20}$ branched alkynyl, $C_{6-20}$ aromatic, $C_{7-20}$ alkyl-substituted aromatic, $C_{7-20}$ aryl-substituted alkyl, and epoxy.

12. The capped polymer of claim 9, wherein -Cap represents the end capping molecule selected from the group consisting of:

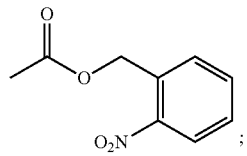

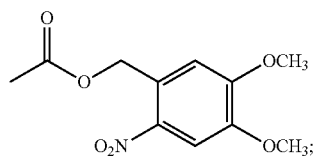

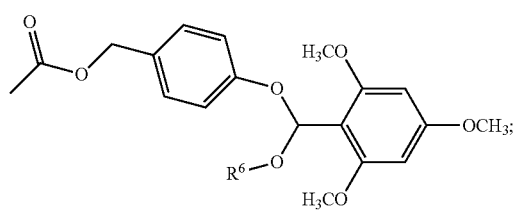

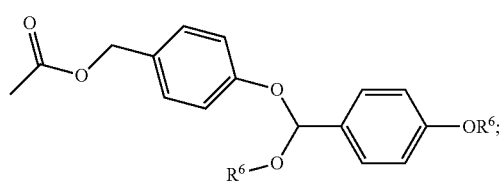

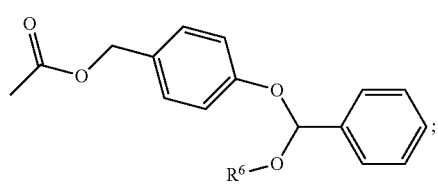

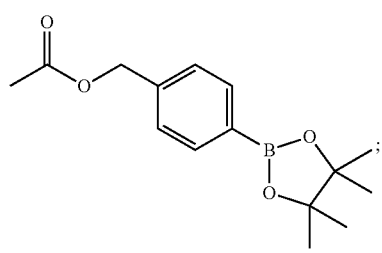

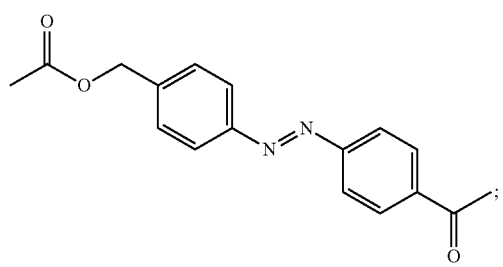

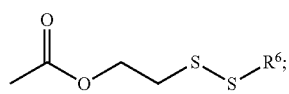

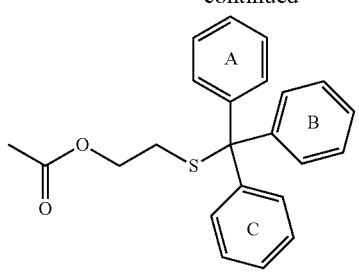

wherein each of rings A, B and C is, independently of the other of the rings, optionally substituted at one or more, including all, para- and ortho-positions with an electron-donating group;

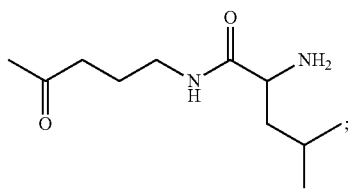

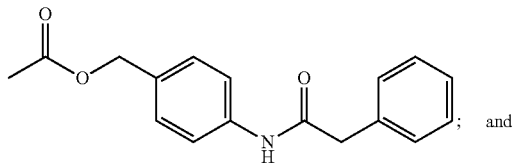

and

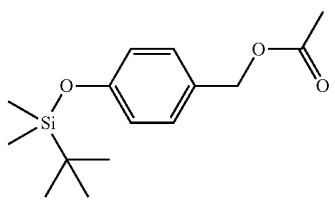

wherein $R^6$ is optionally substituted $C_{1-20}$ linear or branched alkyl, optionally substituted $C_{6-20}$ aryl.

13. A block copolymer comprising first and second blocks, the first block being a polyglyoxylate polymer as defined in claim 1, in which the end capping molecule is a linker that covalently links the first and second blocks.

14. The capped polymer of claim 13, wherein the linker is of the formula:

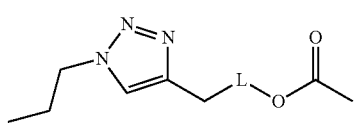

in which L is a group that is cleaved in response to a stimulus such as light, enzymes, heat, change in pH or redox potential.

15. The capped polymer of claim 14, wherein the linker is selected from the group consisting of:

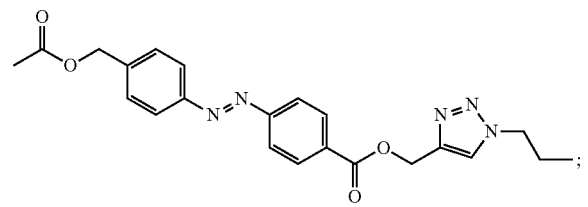

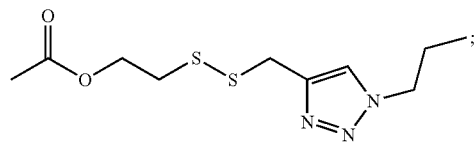

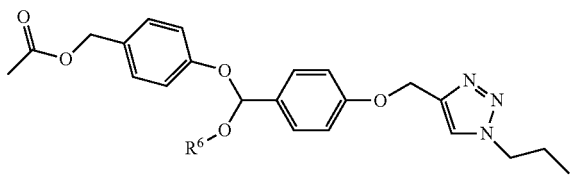

wherein $R^6$ is optionally substituted $C_{1-20}$ linear or branched alkyl, optionally substituted $C_{6-20}$ aryl;

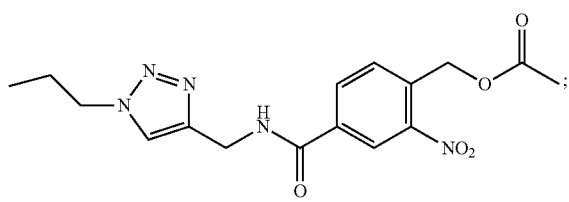

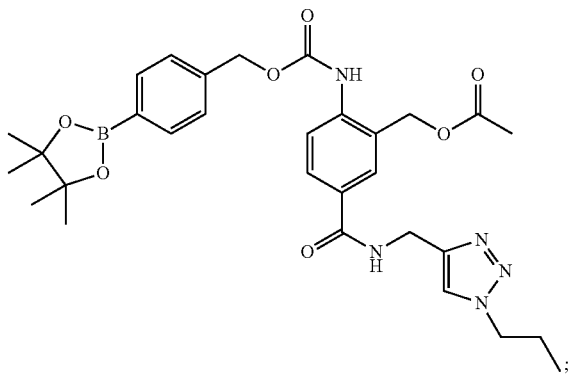

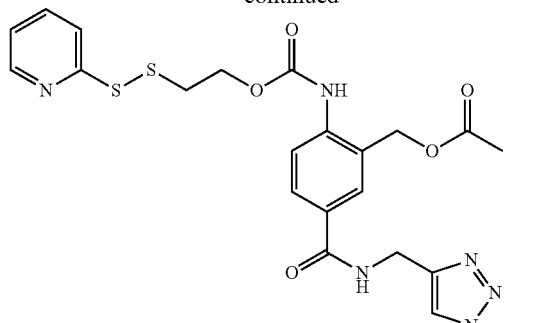

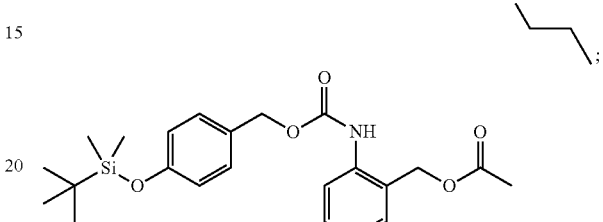

; and

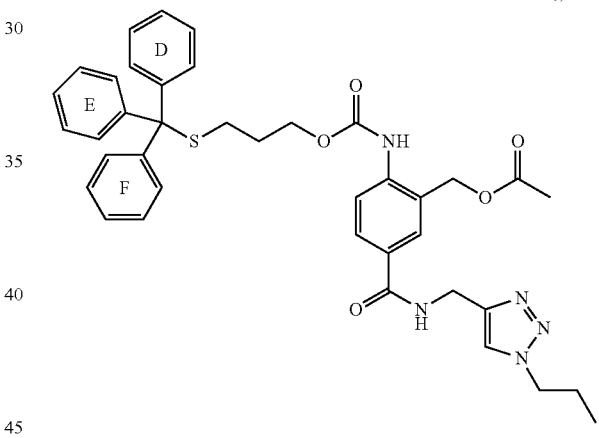

wherein each of rings D, E and F is, independently of the other of the rings, optionally substituted at one or more, including all, para- and ortho-positions with an electron-donating group.

16. The capped polymer of claim 15, wherein each electron-donating group is selected from the group consisting of $C_1$-$C_{20}$ alkoxy, and dialkylamino.

17. The block copolymer as defined in claim 14, wherein said polyglyoxylate polymer is covalently linked to the carbon of the carbonyl group by an oxygen atom.

18. The polymer of claim 13, wherein said second block comprises: a PEG, a PDMAEMA, a poly(lactic acid), a poly(glycolic acid), a poly(lactic acid-co—glycolic acid), polycaprolactone, or a poly(glyoxylic acid).

* * * * *